US006867348B1

(12) United States Patent
Zhang et al.

(10) Patent No.: US 6,867,348 B1
(45) Date of Patent: Mar. 15, 2005

(54) METHODS AND COMPOSITIONS FOR SCREENING FOR ANGIOGENESIS MODULATING COMPOUNDS

(75) Inventors: Ning Zhang, Alameda, CA (US); Anthony F. Purchio, Alameda, CA (US)

(73) Assignee: Xenogen Corporation, Alameda, CA (US)

(*) Notice: Subject to any disclaimer, the term of this patent is extended or adjusted under 35 U.S.C. 154(b) by 0 days.

(21) Appl. No.: 09/465,978

(22) Filed: Dec. 16, 1999

(51) Int. Cl.[7] .................. A01K 67/027; C12N 15/63

(52) U.S. Cl. ........................... 800/18; 435/320.1

(58) Field of Search ........................ 800/18, 3

(56) References Cited

U.S. PATENT DOCUMENTS

| 5,650,135 A | 7/1997 | Contag et al. |
| 6,020,121 A | 2/2000 | Bao et al. |
| 6,217,847 B1 | 4/2001 | Contag et al. |

FOREIGN PATENT DOCUMENTS

| WO | WO 94/11499 | 5/1994 |
| WO | WO 96/40979 A1 | 12/1996 |
| WO | WO 97/00957 | 1/1997 |
| WO | WO 97/11690 A2 A3 | 4/1997 |
| WO | WO 97/18841 | 5/1997 |
| WO | WO 97/40381 A1 | 10/1997 |
| WO | WO 98/28971 | 7/1998 |
| WO | WO 98/30715 | 7/1998 |
| WO | WO 98/55638 | 12/1998 |
| WO | WO 00/08726 | 2/2000 |
| WO | WO 00/36106 | 6/2000 |
| WO | WO 00/54581 A2 A3 | 9/2000 |
| WO | WO 01/18195 A2 | 3/2001 |
| WO | WO 01/18225 A1 | 3/2001 |
| WO | WO 01/37195 A2 | 5/2001 |

OTHER PUBLICATIONS

Wood,"Phenotype Assessment: Are You Missing Something?", Comparative Medicine vol. 50 No. 1 (2000), pp. 12–15.*
Aiello et al., "Suppresion of Retinal Neovascularization lin Vivo by Inhibition of Vascular Endothelial Growth Factor (VEGF) Using Soluble VEGF–Receptor Chimeric Proteins," Proc. Natl. Acad. Sci. U.S.A. 92:10457–10461 (1995).
Asahara et al., "Bone Marrow Origin of Endothelial Progenitor Cells Responsible for Postnatal Vasculogenesis in Physiological and Pathological Neovascularization," Circ. Res. 85:221–228 (1999).
Bais et al., "G–Protein–Coupled Receptor of Kaposi's Sarcoma–Associated Herpes Virus is a Viral Oncogene and Angiogenesis Activator," Nature 391:86–89 (1998).

Benjamin et al., "Conditional Switching of Vascular Endothelial Growth Factor (VEGF) Expression in Tumors: Induction of Endothelial Cell Shedding and Regression of Hemangioblastoma–Like Vessels by VEGF Withdrawal," Proc. Natl. Acad. Sci. U.S.A. 94:8761–8766 (1997).
Berse, B., "Vascular Permeability Factor (Vascular Endothelial Growth Factor) Gene is Expressed Differentially in Normal Tissues, Macrophases, and Tumors," Molecular Biology of the Cell 3:211–220 (1992).
Contag et al., "Visualizing Gene Expressing Living Mammals Using a Bioluminescent Reporter," Photochemistry and Photobiology 66(4):523–531 (1997).
Disalvo et al., "Purification and Characterization of Naturally Occurring Vascular Endothelial Growth Factor–Placenta Growth Factor Heterodimer," The Journal of Biological Chemistry 270(13):7717–7723 (1995).
Dumont, et al., "Dominant–Negative and Targeted Null Mutations in the Endothelial Receptor Tyrosine Kinase, Tek, Reveal a Critical Role in Vasculogenesis of the Embryo," Genes & Development 8:1897–1909 (1994).
Dvorak et al., "Distribution of Vascular Permeability Factor (Vascular Endothelial Growth Factor in Tumors: Concentration in Tumor Blood Vessels," J. Exp. Med. 174:1275–1278 (1991).
Ferrara et al., "The Biology of Vascular Endothelial Growht Factor," Endocr. Rev. 18(1):4–25 (1997).
Ferrara et al., "Heterozygous Embryonic Lethality Inducted by Targeted inactivation of the VEGF Gene," Nature 380:439–442 (1996).
Fong et al., "SU5416 Is a Potent and Selective Inhibitor of the Vascular Endothelial Growth Factor Receptor (Flk–1/KDR) That Inhibits Tyrosine Kinase Catalysis, Tumor Vascularization, and Growth of Multiple Tumor Types," Cancer Research 59:99–106 (1999).
Forsythe et al., "Activation of Vascular Endothelial Growth Factor Gene Transcription by Hypoxia–Inducible Factor 1," Molecular and Cellular Biology 16(9):4604–4613 (1995).
Fukumura et al., "Tumor Induction of VEGF Promoter Activity in Stromal Cells," Cell 94:715–725 (1998).
Hanahan, D., "Signaling Vascular Morphogenesis and Maintenance," Science 277:48–50 (1997).
Ikeda et al., "Hypoxia–induced Transcriptional Activation and Increased mRNA Stability of Vascular Endothelial Growth Factor in C6 Glioma Cells," The Journal of Biological Chemistry 270(34):19761–19765 (1995).

(List continued on next page.)

Primary Examiner—Ram R. Shukla
(74) Attorney, Agent, or Firm—Robins & Pasternak LLP

(57) ABSTRACT

The present invention relates to novel promoters, including transcription regulator regions, for the mouse VEGFR-2 receptor, isolated polynucleotides comprising such promoters, nucleic acid constructs comprising such promoters operatively linked to genes encoding a gene product, such as, a reporter, a protein, polypeptide, hormone, ribozyme, or antisense RNA, recombinant cells comprising such nucleic acid constructs, screening for therapeutic drugs using such cells (e.g., screening for compounds that modulate VEGFR-2-mediated angiogenesis), and endothelial tissue-specific gene expression using these novel promoter sequences.

2 Claims, 60 Drawing Sheets

(7 of 60 Drawing Sheet(s) Filed in Color)

OTHER PUBLICATIONS

Jain, R.K., "Endothelial Cell Death, Augiogenesis, and Microvascular Function After Casteration in an Andgrogen-–Dependent Tumor: Role of Vascular Endothelial Groth Factor," *Proc. Natl. Acad. Sci. U.S.A.* 95:10820–10825 (1998).

Jeltsch et al., "Hyperplasia of Lymphatic Vessels in VEGF–C Transgenic Mice," *Science* 276:1423–1425 (1997).

Kaipainen et al., "Enhanced Expression of the Tie Receptor Tyrosine Kinase Messenger RNA in the Vascular Endothelium of Metastatic Melanomas," *Cancer Research* 54:6571–6577 (1994).

Kappel et al., "Identification of Vascular Endothelial Growth Factor (VEGF) Receptor–2 (Flk–1) Promother/Enhancer Sequences Sufficient for Angioblast and Endothelial Cell–Specific Transcription in Transgenic Mice," *Blood* 83(12):4284–4292 (1999).

Kim et al., "Inhibition of Vascular Endothelial Growth Factor–induced Angiogenesis Suppresses Tumour Growth In Vivo," *Nature* 362:841–844 (1993).

Kitsukawa et al., "Overexpression of Membrane Protein, Neuropilin, in Chimeric Mice Causes Anomalies in the Cardiovascular System, Nervous System and Limbs," *Development* 121:4309–4318 (1995).

Larcher et al., "VEGF/VPF Overexpression in Skin of Transgenic Mice Induces Angiogenesis, Vascular Hyperpermeability and Accelerated Tumor Development," *Oncogene* 17:303–311 (1998).

Millauer, B., "High Affinity VEGF Binding and Developmental Expression Suggest Flk–1 as a Major Regulator of Vasculogenesis and Angiogenes," *Cell* 72:835–846 (1993).

Millauer, B., "Glioblastoma Growth Inhibited In Vivo by a Dominant–Negative Flk–1 Mutant," *Nature* 367:576–579 (1994).

Millauer, B., "Dominant–Negative Inhibition of Flk–1 Suppresses the Growth of Many Tumor Types In Vivo," *Cancer Res.* 56:1615–1620 (1996).

Mukhopadhyay et al., "Wild–Type p53 and v–Src Exert Opposing Influences on Human Vascular Endothelial Growth Factor Gene Expression," *Cancer Res.* 15:6161–6165 (1995).

Mukhopadhyay et al., "Hypoxic Induction of Human Vascular Endothelial Growth Factor Expression Through c–Src Activation," *Nature* 375:577–581 (1995).

Oh et al., "VEGF and VEGF–C: Specific Induction of Angiogenesis and Lyphangiogenesis in the Differentiated Avian Chorioallantoic Membrane," *Developmental Biology* 188:96–109 (1997).

Okamoto et al., "Transgenic Mice With Increased Expression of Vascular Endothelial Growth Factor in the Retinal," *American Journal Pathology* 151:281–291 (1997).

Olofason et al.,"Vascular Endothelial Growth Factor B, a Novel Growth Factor for Endothelial Cells," *Proc. Natl. Acad. Sci. U.S.A.* 93:2576–2581 (1996).

Patterson et al., "Cloning and Functional Analysis of the Promoter for KDR/flk–1, a Receptor for Vascular Endothelial Growth Factor," *The Journal of Biological Chemistry* 270(39):23111–23118 (1995).

Plate et al., "Vascular Endothelial Growth Factor is a Potential Tumour Angiogenesis Factor in Human Gliomas in Vivo," *Nature* 359:845–848 (1992).

Plate et al, "Up–Regulation of Vascular Endothelial Growth Factor and Its Cognate Receptors in a Rat Glioma Model of Tumor Angiogenesis," *Cancer Research* 53:5822–5827 (1993).

Puri et al., "The Receptor Tyrosine Kinase TIE is Required for Integrity and Survival of Vascular Endothelial Cells," *EMBO Journal* 14(23):5884–5891 (1995).

Rönicke et al., "Characterization of the Endothelium–Specific Murine Vascular Endothelial Growth Factor Receptor–2 (Flk–1) Promoter," *Circulation Research* 79(2):277–285 (1996).

Shalaby et al., "Failure of Blood–Island Formation and Vasculogenesis in Flk–1–Deficient Mice," *Nature* 376:62–65 (1995).

Sheweiki et al., "Vascular Endothelial Growth Factor Induced by Hypoxia may Mediate Hypoxia–Initiated Angiogenesis," *Nature* 359:843–845 (1992).

Sheweiki et al., "Induction of Vascular Endothelial Growth Factor Expression by Hypoxia and by Glucose Deficiency in Multicell Spheroids: Implications for Tumor Angiogenesis," *Proc. Natl. Acad. Sci. U.S.A.* 92:768–772 (1995).

Siemeister et al., "An Antagonistic Vascular Endothelial Growth Factor (VEGF) Variant Inhibits VEFG–Stimulated Receptor Autophosphorylation and Proliferation of Human Endothelial Cells," *Proc. Natl. Acac. Sci. U.S.A.* 95:4625–4629 (1998).

Soker et al., "Neuropilin–1 is Expressed by Endothelial and Tumor Cells as an Isoform–Specific Receptor for Vascular Endothelial Growth Factor," *Cell* 92:735–745 (1998).

Soker et al., "Characterization of Novel Vascular Endothelial Growth Factor (VEGF) Receptors on Tumor Cells that Bind VEGF $_{185}$ Via Its Exon 7–Encoded Domain," *Journal of Biological Chemistry* 271:5761–5767 (1996).

Soker et al., "Inhibition of Vascular Endothelial Growth Factor (VEGF)–Induced Endothelial Cell Proliferation by a Peptide Corresponding to the Exon 7–Encoded Domain–of VEGF $_{165}$," *Journal of Biological Chemistry* 272(50):31582–31588 (1997).

Stratman, A.,"Cell Type–Specific Expression of Angiopoietin–1 and Angiopoietin–2 Suggests a Role in Glioblastoma Angiogenesis," *American Journal of Pathology* 153(5):1459–1466 (1998).

Suri et al., "Requisite Role of Angiopoietin–1, a Ligand for the TIE2 Receptor, During Embryonic Angiogenesis," *Cell* 87:1171–1180 (1996).

Takahashi et al., "Markedly Increased Amounts of Messenger RNAs for Vascular Endothelial Growth Factor and Placenta Growth Factor in Renal Cell Carcinoma Associated with Angiogenesis," *Cancer Res.* 54:4233–4237 (1994).

Terman et al., "Identification of a New Endothelial Cell Growth Factor Receptor Tyrosine Kinase," *Oncogene Sept.* 6(9):1677–1683 (1991).

Tischer et al., "The Human Gene for Vascular Endothelial Growth Factor," *Journal of Biological Chemistry:* 266 (18):11947–11954 (1991).

Waltenberger, J., "Different Signal Transduction Properties of KDR and Flt1, Two Receptors for Vascular Endothelial Growth Factor," *Journal of Biological Chemistry* 269:26988–26995 (1995).

Yoshiji et al., "Vascular Endothelial Growth Factor is Essential for Initial but not Continued in Vivo Growth of Human Breast Carcinoma Cells," *Cancer Research* 57:3924–3928 (1997).

Yuan et al., "Time–Dependent Vascular Regression and Permeability Changes in Established Human Tumor Xenografts Induced by an Anti–Vascular Endothelial Growth Factor/Vascular Permeability Factor Antibody," *Proc. Natl. Acad. Sci. U.S.A.* 93:14765–14770 (1996).

\* cited by examiner

```
  1 TCACCCACC TGTTTCTGC GTCCGCGCC TTCTAGTTA ACTTCATGGT TAAAGAACC TGACCCAGGG AGGGTTGCT GCCACAGAAG GAAGGGTCT
    AGTGGGTGG ACAAAGAGTG CAGGGCCCG AAGGATCAAT TGAAGTAACA ATTCCTTCGG AGTGGCCCC TGCCACACCA CGGGTCTTC CTTCCCACGA

101 CCCACAAGCC CCCAGTGTCT CTGAATTGAG GAGCCACTCT GAGCTCCTCA AGAGTCTTCT CTGTCCTCA ATCGGTTCTG AAATTCCCA CTTGCCTTCC
    GGGTTCTTCG GGGTCACAGA GACTAAATCC CTCTGGTCAC CTCGGTCGAGA CAGAGGAGT TAGCCAAGC GAAACGGAGG

201 TTATCCAAGG GACAAGGCTG CCCACCCTAT TGAGGACAGT AGTTCTAAAC TGCTACCCAA CAGACTTTTT ATGGGCTGG GAGAAAGAGA TGAGCTCTT
    AATAGGTCCC CTGTCCCGAC GGGTGGGATA AGTCCTGTCA CAAGATCGTT GTCTGAAAAA TACCCGACC CTCTTTCTCT ACTCCGAGGA

301 GAAGCTCAGC CGAGTGGGCT CTGATTCCTA GTTGGCAAGC CTACCAATA CTGAACCAAG GAGGTGGGT AGGAGGATT CACAGAGTCC
    CTTGAGTG CCTCACCGA GACTAAGGAT GAAGAGTCTC CACGGGTTAT GACTGGTTAC CTGCCACCCA TCCTTCTAA GTGTCTAAGG

401 ACTCGCCCGG GGCTTTTTCT GACTCGGTAG TATTTGTGTC AAAGAAAGAA TGGAAAAAGG GTAAGTCCTG ATTCTGCCTG CTGGAATTCTG CTGGGTCCAA
    TGAGGGCCC AAGATTCCAA CTGAGCCATC ADAAACAGAC TTTCTTTCTT ACTTTTTTCC CAATACACTC TAAGACGGAC TAGGACAGGT GACCAGGTT

501 GAAGGAATAA GGCTTGCAAG AGTAGACACT CACCAAGCAG ATAATGTGTAC CATCAGACC CTCTGAATGG GCTGCAGGA CCAAGACCTG
    CTTCCTTATT CGAAAAGA GTCATCCCTT TCACTGGTAG TATTACAGTG GTAGACCC TGACGCTACT GAGACTTAAC CGGTTCGGAC

601 CAGGCAAGCC CTGAGGCAAA CCAGCTTCAG GAGTAGAAAG GGCCACTCTG GAATGTCCA GGAAAGACCC CTCGAATGG GCGCGTACAG CCAAGACCTG
    GTCGGTTCCG GACTGGTTT GGTCAGATTC TCATCACTTC CCGGAGGTG GAGGTCCTC TTGTTTCTCT GACTTACT CGAGCCTCA CCGTTCGGCTA

701 AGGCAGGTCCA TATCATAATC ATAGTGTG TAGGCCAGGG CTGGCATCGGA AGAGATGACC CTCTGTGTTT TGGCTTGGA CAGAGGGA
    TGGTCAAGGT ATAGTATTAG TATCAACAAC ATCCAAGGAT GGGAAGAC AGGTCATAC GGAGAGTTC AACCGAAGAC CTGGCCTCA

801 TCGACTCTG CTGGGTCTG TGGCACGCC AGGGCTGAGG CTGGGGGTC CTTGGGCTC TAGCTCGAG CTTCGTTGTTT TGTCTACT GTCTCAGGT
    TGGTCAAGGT ACAGCAGAC ACCGCAGACT AACCGGAAG ATCGGAATCT GGGTTGGAG AGCAAGAACG GAACTAGCT CCGTCAAC AGGTTCCGGCTA

901 TAAGGAGCCA GTAAGGGGCC TGGGCACGGC CATAGCAAGG CTGGACACC ATGGCAGTTC TCTGCTCA CAGAGGGA
    ATTCCTGGTT CACTCCATCT AGGGCGGGG GTATGGCTGG GACCGGACTACT TAACCGAAG AGAACGAAGT
```

*FIG. 3C-1*

```
1001 TCTGTAACAG GGAAGGGGTT AATGCACTG GCAGATTCTG GCTTGATTT CTCCAGCAAG GTTGTCTGTC TATCATTTA TCTATGTATC
     AGCATTGTC CCTTCCCCAA TTAGCTGAAC CGTCTAAGAC CGAAACTGTTT CAACAGACAG ATAGAAAT AGATACATAG
1101 TATCTATATA TCTAGTAATCA TCATTAACT ACTTACTTAC ACTAGCTAT TATTACTCA CCTACTACT TACCTACTA
     ATAGATAAT AGATACATAG AGATATGA TGATGAATG GATACATACA TAGATAGAT GGATGGATGA ATGATAGAT
1201 CCTATTTATT TGTTTGTTTG TTTCTTTTGA AACAGGAATCT TAGCACTAC CTATGGCTGG TTTGCAACTC ACTATGAAGC CATAACTGGC CTCTTAACTC
     GGATAAATAA ACAAACAAAC AAAAGAAACT TTGTCCTAGA ATGGATG GATACCGACC AAACGTTGAG TGTACTTCG CTATGACCG GAGAATGAG
1301 ACAAAGATCC ACTGCCTGT GTCTCTGAGT GCTGGAATTA AAAGCATGTG CCACTACACC CAGCTCCAGT AGGACTTTA GAACACATTT CCCATCCGA
     TGTTCTAGG TGACGGACA CAGAGACTCA CGACCCTTAT TTTCGTACAC GGTGATGTGG GTCGAGGTCA TCCTGAAAT CTTGTAAA CGGATACGGA
1401 GCCTAAGACA CACACTCAG TCCCAGCCC CCAGCTCCC CTAGGATTCA AAGCATGTTCA GTATGGGAATC CAAATGAGC GTCTCCAGT CAACAAGAAG
     CGGATTCGT GTGTGACTC AGGGTCCG GTCGGAGG ACAGATTCG GTACAGTT CATACCCTAG GTTATCTCG GCAGATGAGG ACTTAGAGAC
1501 AACCCCTCAG CGCCAGCCC CTCTTCTCT TGTGTTAGC AAAGTCCAAG GTATGGGATC CAAATGAGC GTCTCCAGT CAACAAGAAG GGGATTTC
     TGGGAGTC GGGGTGGG GAGGAAGAG ACACAATCCG TTTCAGTTC CATACCCTAG GTTATCTCG GCAGATGAGG ACTTAGAGAC AGTGTCTC
1601 CAAAGTCTG CAGCTCTTGA TGGAGGTGT CACAGTTCA GGCCCCCTCC CTGAAGCCC ACCACTATCAC AGCCCACTTT COCCAAAAAG TCAAGAGGC
     GTTTCAGATC GTCTCTTT GTTGAAACT ACTACACACA GTGTCAAGT CGGGAAGGG GACTTCGGG GTGTCAAAA GTTCACGAGT
1701 AAGCCAGCCT TGTCTCCT CATACCCAC GGATTCTGG TGGGTTCTG CAGAGAGGA GTTCCCCAG GTTCCCCAGT GAAGCAAGG ACAGACTCA
     TTGGTGGA AGAGAGGA GTATGGTGT CCTAGAGCG GTCTCAAGT CTCTCTCCT CAAGCTCGG GACTTCGG TGGGTCAAA GTCTCTTC
1801 AACACGGCTG ACAGAGACT CCTTCCCAC TCCTTCCCAC TGGGTCCTG CAGACAGA GACTTTAAC TACTCCAAGT CTGGTACACC AAGACTGCC
     TTGTCCGAC TGTCTCTGA CGGAAGCCG GAGGAACCG AGGAGACTCA CGACCGTGAG CTGAAGGTCA TGAGGTGG ACTCTCTCG TTGTGCAGT
1901 ATCAGGAGAG AACGACCAA GCCAGGAGG AATCATGGAA TAGAACAAGG ACTCCACACC CTGCCCCTT CCCTCCACG CTGAGTACC TGAAGAAGT
     TAGTCTCTC TAGACTGGTT CGGTCCGAG CGTCTCTCC TTAGTACCTT ATTTGTCC TGAGGTGTG GACCTCTCT TTAAGAAGT AACTTCTCA
```

FIG. 3C-2

```
2001 AGACCTTTC CGGCCCACTG TAACGTGGG CAGGAAGGGC GAAGCCTGCA TGAACATGT CTGGAAGCCT TGGAGATGT TGGGGGATA
     TCTGGAAAAG GGCGGTGAC ATTGCCACCC GTCCTGAAGT AGTTGAACA GACCATGACG TGACTTCGA AAGCCCTTAT

2101 ACCAGGTCC AGGACCCCAT CCTGAAAGCG CCAGTACTGA ACACGAGAT CAGAAGGGTG AGGAATACC GCTGGGCACA GAAGCAGTCC
     TGGTCCAGG TCTGGGGTA GGACTTCC GTCATGACT TGTGTCTCTA GTCTTCCCAC TCTGTATGG GGACCGGTGT CTTCGTCAGG

2201 TATATCCTAA ACTGCCTC ACTGCTGT AGTAAGTCTT CCCTGCAG CTTCCTTGAA CTTCACGCT ATCAGGCAC CCTTACTTT GCCTAGACT
     ATATAGCATT TGACGACAG TGACGAGGA CTCAGGGAC TGAACAACA GAAGTGTCGA GGGTGGTC GGAAATGGAA GGAGTCTGA

2301 TAGGTCTGT ACTTGAAACA AGTAAGGTCTT CCCTGACAG TTGATCGAG CCCTAGAACA GGGGAACTG ATCGATGGG CCCTGAAATC TTGGATAAGT
     AACCCCATGG GTCAGAAGTG CGGCCTTCC GGACTTCA GGACTGACT TGCTCATGAC GGATTCTTGT CCCCTTTGAC AGTCAGGATC TTCCGTCTAG

2401 TGGGTCTACC CAGGGCCTGC TCCCGTCTCA ACAGGACTG CAAAGAGGG CCATTTCTTG AGATCAGGTC AGATGAGGCCT AAGGCAGATC
     AACCCCATGG GTCAGGAGTG CGGCCTTCC GGACTTCA GGACTGACT TGCTCATGAC GGATTCTTGT CCCCTTTGAC AGTCAGGATC TTCCGTCTAG

2501 CGACCCCAC CAGAGCTGTC TCCCGTCTCA CATAGAGTCA CCTTCGAAGG CAAAGAGGGA ATTCCTCCT GTGCTCCAG TTTGGGGCT CTGCACAGTT
     GCTGGGGTG GTCAGGACA GTATCTCAGT GGAGCCTTCC GTTTCCT GGTAAGAAC TCTAGGCACT TCGGCAGTT GACGCGTCA

2601 CTTCCTCTGA AAACTCAGG GTCCGTGTCG GCTTAGAGT GCCGTCGTC CAGTGGGTGG AGTAAGGA GTAAGGA TTGTCCAC GGGGTTCTC GCTGTTCTC
     GAAGGAGAC TTTGAGTCCC CAGGGACAG CGAAATCTA CGGACCCAG GCTCCTAAAT CCAGTCCCC ACCTTCCAC AAGACCCAA CGTGTGGCCA CAACCAGAG

2701 AGGATCTAGG AAGCTGTCG GCTTAGAGT AGTTAGAGT GCCGTCGTC CAGTGGTGG ATTCCTCCT GTGCTCCAG TTTCCGGGT CAACGGAAC
     TCCTAGATCC TTCGACACC CGAAATCTA CGGACCCAG GCTCCTAAAT CCAGTCCCC ACCTTCCAC AAGACCCAA CGTGTGGCCA CAACCAGAG

2801 TTCTGGGCT CCTCAGTA GTCATAGCTC CAATAAATCAT CTCTGGCAT AGTGAACACG TTACTCCAGG TCCCCGGGGC TACACTCTC CAGAACGGGG AGCAGTAGT
     AAGAACCGA GGAGTGCAT CAGTATGCAG GTTATTAGTA TGACTGGTA CAATGAGTTCC AGGGGGGGC AATGAGTTCC TGTCACTCA

2901 GTCAGGCTGT GGAGGAGCC CCAGCCACAG GGCATAGGGC TCTGAACTCA CCTTGGTCTA CAGAACGGGG TCTGATAAGT
     CAGTGGGACA CCTCCCTTGG GGTCCGGGTG GTTCGGACG AGACTTGAGT GGAACCCGA AGTGAGCGAG GTACATCAGC CGTGTGTGTG AGACTATCAT
```

FIG. 3C-3

```
3001 AGTGCAAACC TGGTGCAACT GACACTTCTT GCTGGCCATG AAACCCTGAG TGCAGCGCCC CTTGCATGAC TCTATGGGAG GGAATATGAG GTTTACAGCC
     TCACGTTTGA AGCAGTGA CTGTGAAGAA CGACGGGTAC TTTGGGACTC ACGTCGCGGG AGATACCCTC CCTTATAGTC CAAATGTCGG
3101 CAATCTAGGG CACTCGCCA ACTGCACTT CCCTGCACAC CTACCAAATCC CTTGGTGCAG CAGAGAAACC CATGCCACA GGGCTAGTAT
     GTTAGATCCC GTGAGACGGT TGACGTGAA GGACATCATG GGATTCCGAC TTCCGATCC GGAGGGTGTG GTCTCTTTG GTACGGTCGT CCCGATCATA
3201 GAAAAGGGC CTCAGGGGTG CCATGGCAGG CTCTAGCCC AGGGCTTGG CAAGCTGGCC GGGGACTTC TGCAGTCTCG CATGCCACA AGTGCAAGCA
     CTTTTTCCCG GAGTCGGCAC GGTACCGTC CCGGAGGCGG TCCCGAACC CGGAGGGGG CCCGGAGGGC AGTCCGGG ACCTTAGAAC GACAGGACGG ACTTTTTCT
3301 AGCAAGACTGA AGAAGAGTTC CTAGTGCCCT GGGTTCGTCG ACCAAAGACG GGAAATAAAC GAGTAGGAGA CGGGTCCGG GTAACGGGAG GAGGTTGTG TGCAGCGTCT
     TGCTGCTGACT TCTTCTCTAAG GATCAAGGGA CCCAAAGACG GGAAATAAAC GAGTAGGAGA CGGGTCCGG GTAACGGGAG GAGGTTGTG TGCAGCGTCT
3401 AGGGTCACA TTCCCAGAAC CCCACCCCA GGAGACTGG GAAACAGAAA ACCTTGGCCA AGACCAAAGT CAGTAGGGTC AGGGGCCAGGA GGGATAACAC
     TTCCAGTGT AAGGGTTTG GGGTGGCGGT CTCTCGACC CTTTGTCTTT TGGAGCGGGT TCTGTTTCA GTCATCCCAG TGCCGTGCT CCCTATGTG
3501 GCTTAGCTTA GCTGACGGAG TGGAAAGAAG CATGTGGTTGT AGAACAGACA CCCAGTCCCG TTAATCCAA AGTTCCAACA TCATCCGTAC TTTTATATAA GTGGGACCAT
     CGAATGCAAT CGACCCTTC ACTTCGTTC GTACACAACA CGGTCAGGGC AATAAGGGG AATTAGAGGG ACTGGAATG AAAAATATT CACCCTGGTA
3601 GTGCCTTTTC GGAGCCTTTC CATGTGAGCT GTTGGAGAGT GTACACAACA CCCAGTCCCG TTAATCCAA AGTTCCAACA TCATCCGTAC TTTTATATAA GTGGGACCAT
     CACGGAACG GAGTGGTCA CAACTCTGA AGGCACTCGA TCTTGTCTGT TTTGCAAAGC ACGGACTTCA TGGAAGTTG AGTAAGGGTA TGGGCAATA
3701 CGATTACTG TTTGATCAGT CTAGTGCTT GTCCCATCCT ACCCCCGCT GCCAGTCCGA AGTTCCAACA ATTTTTGGG CAAGAAGGGA GGTTAGGCGA GAGTCGGA
     CAACGGAAG AAACTAGTCC GATCCAGGA CAGGTAGGA TGGGCCGCA AGTTAGAACC TAAAACCC GTTCTTCCC CCAACCCT CTGACGGTT
3801 GCACTTGGG GGAGTTTC TTTCTCTT ATAAAAGAAC AAAGCTTCAT TTTCTGCCTC TCCTTGTCT CTTCAAGGG GTTGAGGGCA CATGAGGAGT
     CGTGAAACCC CCTCCAAAAG AAAAGAAGAG TATTTCTTG AAGACGGGAG AGAACAAGA GAGATTGAC CCAACATCAG CCACATGTC GTATCCTTCA
3901 AGGGGTCAG AGTCTATTCT TCTTTCTTA TTTATTTTG ATTATTGTTT GTGTATAAGT GTCTCGTCAC AGCGGAAGT CATAGGAACT
     TCACCGAGTC TCAGTCAAGA AGAAGAAAT AAAAAAATC TAAATAAATA AAATACAAAA CACATATTCA CAGACGAGTG TACACGTAGA CACGTGGTGT
```

FIG. 3C-4

```
4001 TCCATGTCTT GTGTCATGTG AGGTCAGAAG AGGGCTTTGA ATACCTGAGT ACTGGAGTTT TGAACAGTTA TGACTGCCCG TGTGGATCCT GAGAATCAAA
     AGTACAGAA CACAGATAAC TCCAGTCTTC TCCGAAACT TATGGGACCT TGACCTCAAA ACTTGTCAAT CTGACGGGC ACACCTACGA CTCTAGTTT
4101 CCCAGGTCCT CTGTAAGAAC AAGTACTCTT AAAGGCTGAG CCATTCTCC AGTCCAGAG CCATTCCTC AGGTCTCAC TAATCATG ATCCTCGGG
     GGTCCAGGA GACACTCTTG TTCATGAGAA TTTCCGACTC GGTAGAAAGG TCAAGTCC GGGTAAGGAC TCCGAAAGTC ATTAGGTAAC TAGGAGCCC
4201 GACCACCCTG GCCACACTTC CAATGACCTC ATTATTTTA AAAAAAAAAT GGACTCATTG GCCATACTT CTAGACTCAC ATACTAAGTC GGATTCTCT
     CTGGTGGGAC CGGTGTGAAG GTTACTGGAG TAAATAAAAT TTTTTTTTTA CCTGAGTAAC CGGTATGAAC GATCGAGTG TATGATCAG CCTAAAGAGA
4301 ATAAAGAAGT GCTCACTGGG GTAGAGTCCC AGTTGGG CCTAATTCCA ACCACTCCGT CACTCTGAA GCCCCTCCGT TTTCTGTCT GTAATCACAG
     TATTTCTTCA CGAGTGAACC CATCAGAC TCAAACCC GGTTAAGGT GTGAGAGCA GCGGAGGCA AAAGACAAGA CATTAGTGTC
4401 GCGAGGTGC CTTTGGTGTC TCTCTCTATC GGACGCACT AGTCACAGGC GCAAAATGAA ACACTAAAT TGACTCCCCA CAGAGCGGTG AAGCCTAAGT
     CGCTCGACG GAAACCACAG AGAGAGATA AGTTACGGCT TAGCCCTCG CGTTTTACTT TGTGATTA AATGAGGAT GTCTCGGAC TTCCGATTCA
4501 GGAAACGGGC ATTAAGGGC TTTAAGAAAT TCAAGCTCGA TTTCTTAACC AACCCCTTCT ACAAGCATCT GCCACCACC AAGGGGGAGAC TGGGAAGGC
     CCTTGGCCG TAATTCCCG AAATTCCTG AGTTACGCT TAGGGGAAGA TGGGGAAAGA CGGTGGTAG TGGTTGGT CCGACGAAG TGTAAAACCC
4601 GAGCGGAGCG AGGGGTAGGA AATGGAAGAC AGCCCTCGCC AGCCCTTTCT ACACCATCTT GCACACCCC AAGGGAGAG TGGGAGACC AGGGCGCC
     CTCGCCTCGC TCCCATCCT TTACCTTCTG TCGGGAAAGA TGGGTAGAA CGGTGGTGG TGGGAAC CCCCTCTG TTCCCTCTG ACCCCTCCG
4701 AGGTGTGGGC GTGGGTAGGA ACCTGGGGTA GCTTGCGCC TCGGGGGG TGAAACTAG AAGGGGAGAG TCAAACCTT GACTCTGCTG
     TCACACCCG CACCGACTC TGGACCCAT CGAACCGG AGCCCCC ACTTGGATC TTCCCGCC AGTTAGGA CTGAGACGAC
4801 CTGAGGAGGG TGGTTGCTGT AGGGGTAGGG ACTGGGCTG TGCTTAGATT GGAGCCCGT GCACCCGGCT CTTACCTTG CCGGTCTGG
     GACTCCTCCC ACCAAGACA ACTGTAGAA TGAGCCCGAC ACGATCTAA CCTGGGCA AAACCACGCA CGTGGGCAG GGCCAGACC
4901 TCCATGCTTC TCTTCTCCTT CATGCCCTC GAGTCCGGA GCTCCCGAGAA GGATTCAGGGA CGACGGAAGG TAGCCCAGCA CCTTACCGG
     AGTACGAAG AGAAGAGGAA GTACGGGAAG GATTCAGCCA CCTAGCGGCCT CGACGGGAAC AGAATGGAAC ATGGGTCGT GGAAATGCCC
```

```
2001 TGCCATGCAT GAAGATCCCT AGCACCAGCAT AGCCAGGAG TGGTTATCCA CCCAGCTCTC AGAAGGTGGA GGGAGGAGGA GCAGGAGTTC
      ACGGAGTA CTGGTAGGA TGTGTCGTA TTCGTCTC ACCAAATAGT GGTGGAGAG TCTCCAACT CGTGCTCCT CGTCCTCAAG
2101 GAGGCAGCC TGTGCTACTT ATGGAGTCA GCCTGCACTG CAAGGATCA TTATTTCA AAGTGGCCT TGGGGGAGG TGGGTGAGG AAGTAAGAGA
      CTCCGGTCCG ACACGATGAA TACCTCAGT CGGAGTGAC GTTCCTAGT AATAAAAGTT TTCAACGGA ACCCCCTCC ACCACTCC TTCATTCT
2201 AAGTGACAGT AATTTGTCA CTGAAGAGTT GGAGGTTCCT GAGGCCTC AAGTGTGAAG GAACTTTACC AATTCTGCCA GTGAGGAGTA GGGGTATTA
      TTCACTGTCA TTAAACAGT GAATATCAA CCTCCAAGGA GACTCCGGAG TTCAGACTTC CTGAAATGG CACTCCGGT CACTCCTCAT CCCCAATAAT
2301 TTTGGGGTTC AGGAGGAAGG AAGTTTTCTT AGGCTGATA GAGGTACCCC CAGAGCTCAT GGTCCTGTG CTTGACTCAG AGAAGAAGA
      AAACCCAAAG TCCTCCTTTC TTCAAAAGAA TCCGACTAT CTCCATGGG GTCTAGAGTA AGACTGAGTC GAATGGGTC TTCTTCTCT
2401 AAAGCGAAGG GTTCGGAACAA GCTGGAGCTCA GCTAAGTTCA GGAGCTGCTC GGGAAGGATCGAC TGTAGGCGGT AAGGGAAGT
      TTTCCTTTC CAAGGTGTC TGGCTTGTT CGACCGAGT CGATTCAGT CCCCTAGTG GTTCACGCCA TTCCTCTCA
2501 CTGGGGTGT CTGAGGCCG TACTGGGAGG ACTTCCCTT GTTCTTCCCC GCTTCTGAAG GCTGGGAGCT CCCTGGGCGG CTTGGGGG
      GACCCCACA GACCCCG AGAGCCTTG CAAGAAGGG GCAAAGAGTC ACAGGACAC CTTGGGCCA AGAATCCTA
2601 CAGGGGTCAG TGAAGTGGCT CCAATGCAT GCTAGAGACC ATGCCCACTC ACTTCGACT GTCCCTGAAT ATGTCCCAC
      GTCCCAGTC ATATCGGACT ACCTCACGA GGTAGACGTA CGAGTCTGGG TACGGGTGAA CAAGGGGTA TACAGGGGTG
2701 ATGTCACCCT CCTGCCTTTC TCTCAGCCTA AGGAGACAAG CTAGAGTCAG CCCTCCTCC ACCTTCTTTT CTTCACTAAA TAATAATCCA TTCCCTTCCTTC
      TACAGTGGGA GGACCCGAAAG AGAGTGCGAT TCCTCCGTGTC GAATCTCC ATTAAGAGAG GAAGTGATTT ATTATTAGGT AAAAGGAAAG
2801 CTGGCCCAT TTTTTTTCC TCAAGTGGGG ATCACCTTGT CTTAGTCCAG AGCCTGAAGT CGAGGTTCA AGTGGGAA CGGACTTAC
      GACGAGGTA AAAAAAAGG ACTTGGGAT TAGATGGGA TCCGGACTTC GCTAACGTC TCGGAGGACC GGTTGAACTA TGCGGACTTG CCGACTGAC
2901 CCATCATCCT GACTGGCTCT GGCGAAAAC TATTTGTGTC TAGTCAATT CCTTGTCTGC TACCCAGCT CTGCCGAACT TGAGCTGGTG
      GGTAGTAGGA CTGACCGAGA CCGACCTTG ATAAAACAAG GGAACAGACG ATGAAGTCA TAGAGTCAR GACCGCTTGA ACTCGACCAC
```

*FIG. 4B-3*

```
3001 GCCCCACCA AGCCCACTTC TTTCTCTCTT GTCAACCCC CCACACACA AACTTCATGC CTGCCCCTTG AAACCAGGGT CCGTCTCTGA
     CGCGGTGGT TGGGTGAAG AAAGAGAGA CAGTTGGGG GGTGTGTGTT TTGAAGTAAG GACGGGGAAC TTTGTCCCA CGCAGGAACT
3101 CTGCCCTGTCG GGAGGCTGAA AACGAACCT CATTAAAAAC AACACATAAG TGACTCAACA AACTGTAGTG TTTGTCTTTT
     GAGGGCAAGC CCTCGACTT CCTCTACCA TGTCTTGGA GTAATTTTG GTAAATGAATC ACTGAGTTGT TTGACATCAC AAAAGAAAA
3201 TTTCCTTCTCA AAAATTATTT CGTTTGTTTA CCTTATGTTT GAGAGTAGTC TGGTGCACCA CAGCACACAT AGAGGTCAG AGGGAATTT
     AAGGAGAGTT TTTAATAAAA GCAAACAAAT AAATAATAAA CGAATACAAA CTCACTCAGG ACCAAGTGGT GTCGGTGTGTA TCCCTTTAAA
3301 TCATAGTTG TTCTCTCTT CCGGTGTGTC GCCTTTCCT GAGATTACAA ATGTTCAACA TCACAAGAAG CTTGGAGTTC TTGCCTATCA GTGAGGTACT
     AGTATCAAAC AAGAGAGGAA GCCACAACGA CCGTTAGAGG AAGTGAGTCA CTCGATGTGT CGGAGAAGA GCGAAATTC CGTCTCATGA
3401 CCTTAGTACA GGGGACCCT TTGGCTCGCC TCTCAAGTGT TAGTCGAAG GCACGAGTA GCATGGCCG CCAGGATTTC CTTGGAGTTC GTGACAGTTCA
     GGAATCAAGT CCCCTGGA AAGGACCCG AGAGTTTCA CCCTTAACGT TACAAGTGCT GTACCACAGAT GTTCTGGAAC AAGGATAGT CACTGGGGA
3501 CTTCCTCCCCA GCTTCTTCC AACCATCTTT TAGTCGATG GGAAACCGA GCATGGCCGT CCCGGATTC CTTGGAGATT GTGACAGGGG
     GAGGACCGAT CCGAAGAAGG TTGGTGAAAA ATCAGACTAC CCCTTAACGT TACAAGTGCT GTACCACAGAT GTTCTGGAAC AAGGATAGT CACTGGGGA
3601 CAGTTGGGAG GGAGCTGTCC AGCCCCCTCCC ATGACCAGCA AGATGTAATG AGTCGGGGT TGGGCGGGTG CGAGGATTTC GGATCCGGCT
     GTCAACCCTC CTCGACAGG TCCGGGAAC TAGTCGTGT TCTTACATC TCACACCCA ACCCCGTAC TTGACTGAGA CACACCACGC ACTGGGGA
3701 TCTCTCCTTC ATGTCTCTGT ACTGGGCTGGA ATGACTCAG CTCAAGTAGG AAAAGCGAGA GCTCAGAGTCG AGATCCCG
     AAGAGGAAAG AGCAGAGGA TACTGGACCA AGTAATCCT TGAACTAGTC GAACTTCAGC CACACCAGG ACTGGGCGC
3801 ACGTTCCAAA AGAAGAAGGGA ATGACTGAGT TTGTCTCTGT TCCATTAGGA AAGCCAAGA CGGAAGGG GCTGAGTGCC GAGACCCGG
     TCGAGTTTT TTCTCTTT GGGAACTCA ACAGGACCA CCCTTGTGT CAACTTCAGC CACACCACG CGGGCGACG CTCAACGGC
3901 CGAGGTTGAGA GATTTCCCAG GGTCAACATC CGGTCAACTT GGAACACGC CCACACGC CCTGCCCCTT CCGAGACCCAG
     GCTTCACTTT CTAAAGGGTC CGAGTTCCTT CTGCCCCGAA CGGGCCACGA GTGGCTCCGGG GGAGCGGGAA GGTCTGGTCG
```

*FIG. 4B-4*

```
4001 CGAGACGCAC CCCCCAACCT CTCTTTACAC ACAGTGAAGT TCAAGTCCTC GGGACCCCT TCCCGTGTGT TAGCCCTTCG
     CCTTCGTG GGGGTGGA CTCCGGAAGA GAGAATGTG TGTCACTTCA AGTTCAGGAG CCGCTGGGA AGGGCAACA ATGGGAAGC ATGTACTTCCT
4101 CGTTTGTCCT CACCTGCCCG GAGTCTCCG CGTTCGCCGG CCTCACCCCA GCGAGCAACC GTCGACCCG CTGAACTGGC CCTCCCTTCT
     GCAAACAGGA GTGGAGGGC CTCAGGGCC GCAACGGGCC GCGGTTCCG TGTCCCCCT CCGGAGTCG CAGGCTGGG GACTGAGCG GGAGGAAGA
4201 TGCTCCTGTA ACTTGACTCT CTGTCTGACC AGGGACATGG AAGGACTCC TTTGTGTTT GTCCTTCGTC TCTGGTTTTC
     CACAACTTGG AAACTAGAGA GACAGACTGG TGGACCGGA AGAGGTACC CTGTACTCCC TTCCTGGAAG AAACACACAA CAGGAGACAG AGACACACA
4301 GTGGTGACCC ACTTGACTCT CTGTCTGACC AGGGACATGG AAGGACTCC TTTGTGTTT GTCCTTCGTC TCTGGTTTTC
     ACGAGACATT TGAAAATCT GTTTGTTTTG AAACAAACCC GCAAGGAACA AGATGAGGAG GAGAGGGGAG GAAGCAGTCC GGGGGTGTGT
4401 TGTCCCCCCG CGGAACCGA GAACTGGTGA CTTGGGGGAC AGGGGTGGG GGGGGATGA ACACCCTCC TGCATATCTT TGTCCTGTTA CTTCAAGCCA
     ACACCGGCC GTCTGGCCT CTGACCACT GAAACCCCTG TCCCACACC CGCCCCACT ACGTATAGAA ACAGGAGACAG AGACACAAAG
4501 ACTTCTCGGG AAGATGGGCT GACTCTGTTT GTACCTTCCA GAGGGAAAT GACACCACCG GTCTTAGCTG AGGCTGGAGG GGAAAGAGTG CTGAGTGTGG
     TGAAGACGGA TATCACGGA CTGACCCACC CATCCACCCC GTGGAAACCG CAGAATGCAC TCCGACCTCC CGTTTCTCAC GACTCACACC
4601 GGTGCAGGGT GGGTTGGGCA GGTTGGGCA ACGAGGAAT GACACCACCG GTCTTAGCTG AGGCTGGAGG GGAAAGAGTG CTGAGTGTGG
     CCAGGTCCCA CCCAGCTCCA GCTGACCGT CTCTCGGGT TGCTCCTTTA CTGTCTGGCC AGGACAGGAA GAAAAGCCGG TGGGTGGGTA
4701 CCAACCTCAA GGGTCCAGGG TGACCAAGAT AGCTCGTTT TGCTCCCCTG GATTACTTA ACATTTCCAA GAGGTTACA CTTCTCCTTG
     CAGTCCCA CCCAGCTCCA ACTGGTTCCT CTGACCGT CTCTCGGGT TGCTCCTTTA CTGTCTGGCC AGGACAGGAA GAAAAGCCGG TGGGTGGGTA
4801 GACGAATGA GCCCCGACT GAGGGAAGTC GATCCCCCTG TGGGAGTCT GCTAACCTTA ACATTTCCAA GAGGTTACA CTTCTCCTTG
     GGTGGGAGTT CCCAGGGGTTGA CGGGGCTTGA CTGGTTCTA ACCAGGGAAC CTAATGAAT TGTAAATGTT CTTCCAATGTT GGAGGAGGAC
4901 TCAGTCTTTC CCTCCTTTCA GGGCCAAGGCT AGTTGGATT TTTTTCCCTG AGCCCCCCTTC ATTCCAAAAT GTGAAACCCT ATCAGACCAT
     AGTCAGAAAG GGAGGACCCT TTTGACGGAG TCCAACCTAA AAAAAGGAGC TCGGGGATGC CAACTCAGGC CGCTCCCAC GGGGAGGGTG GGGACAGTC
```

*FIG. 4B-5*

```
5001 TATTATCTA TGTCCTCTC ACTCTACC CCACCCAAG CCCCTTCTT GGGCCTTACT GGTTTGGGC AGCAGGGGGC GCTGGGACGC
     ATAATAGGAT ACAGGAGAG TGGGACTGGG GGTGGGTTCC GGGGAACCG GGAGGACGAA CCGGAATGA CCTGGGCCTC CGAAGCTGCG
5101 CCACTTGCCT GGAGCGCTTT ATACTGTGAA TGAGTGGTTG GGGGCCCGGAT GGGGCCCCTC CCCAGCCCTC CAAAACTTTT CCTGGGCCTC
     GTAGAACGA CCTGCGGAA TATGACACTT ACTCACCAGC CTAAGGACCC GGGGGGGCCTA GGTCGGGGAG GTTTTGAAAA GGACCGGAG
5201 CCCTTGCTCC ACTGCTTCC TCCCTCCCTT TGACAGGAG TTAGACTGA AAGGATGCAT CCCTGGCCT TCTGTCCTCTCG GCCCCAGACT
     GGGAAGAAGG TGAACGAAGG AGGAAGGGA ACTGTGCCCT AATCTGAGCT TTCCTACTGG TCTGGGTAG AGAAGAGTC CGGGTCTGA
5301 TTTTCTCTTT AAGTGCTGCG CCTTCCCAG CAACTCTCTG CCAACCCGGG AGCCCTCACAG AGTGCGAGGC AATTTTCAGA
     AAAAGAGAAA TTCAAAAGC GGAAGGGGTC GGAACCTGCG GTTGAAAGG GGTGGGCGTA TCCAGCTCCG AGAACGAGTC CGGGTCTGA
5401 GAAGTTTCA GGGCTGAGCG TTTGGCCTCC CTATCCTGA TATTCCTGAA GCATACTTAA GAGGGGGCTG AGTCCCACT
     CTTCAAAGT CCGGACCTCG AAACGAGGG GATAGAGCT GGGTTTATCA CGTATGAATT CTCCCCGAC TCAAGGGTGA
5501 ATCCACTTCC ATCCAATTCC AAGAGAGTT CTGTCCTTC AGAATCCCAC GAGTCAGATT TCTAATTCT
     TAGGTGAAGG TAGGTTAAGG AAGTCAGGGT TTCTCTCAA GGAGGGAAG CTGAGTCTAA AGATAAAGA
5601 AATATGGGG AGATGGCCCC TACCGGGCCC CCCGGGGCCT TCATGGAACA TTGCTTGGGC AAACTAAATC GAGTCGAGAT
     TTATAACCC TCTACCCGG ATGGGGCCA GGGGCACAG CGTACCTTGT AGGTCAGAAG ACAGGACACA CACCGCACAG
5701 CCCCAGCTA TTTATCCCT TCTTGGTTCC CAAAAGCAC GTTCAAAGT TAAAAATATT TAAATATATT GCTTCGTGGG GTCCGTGTCC
     GGGGTCGAT AGAACAAGG GGTTCAAATG AGACAAGCT AACAATATTT ATTATATAA ACAGGACCC TAAACTCAGT CTGAAAGAAC
5801 GTCCGTCGGT GGGTGGCCCG GAGCTTCCTT GTTTCAAAGT AACATATTT ATTATATGAA TACAGGACCC CAAGTTTTAG CACCGCACAG
     CACCCACCCA CCTGGCAAGG CAAAAGTTCA CACGGACCT CAAGTTTTAG CGAAGACCCC TAAACTCAGT CTGAAAGAAC
5901 TGTGCACTTT TTGTTGTTG TCTGGCTCTT GAACTTCCTGTT CGGACACTTC TGTCTCCCTC AGACCACTTC
     ACAGTGAAA AAACAACAAC AGACCGAGG GGGCCGAGAG AAGAGTTCAG ACAGAGCGAG TCTGGTGAAG
```

*FIG. 4B-6*

```
6001 CAACAGTCT CCACTCTCAA TGACTCTGAT CTCGGTCTG CGGGACATG CAATTTACT TCTGTAAGTA AGTGTGACTG
     GTGTGACAGA GGTGAGAGTT ACTGAGACTA GAGCCAGAC AGACAAATGA GCCCTGTAC GTAAAATGA AGACATTCAT TCACACTGAC
6101 GGTGGTAGAT TTTTTACAAT CTAATATGTT GAGAATCTG GGTGGAAATG TCTGATCAGG AGAATGCCT GCCACTCCG ACCACAATTC ATTGACTCA
     CCACACTA AAAAATGTTA GATAAGCCAA CTCTTAAGAC CAACTTTAC AGACTAGTCC TCTTCCCGGA CGGTGACGGC TGGTGTAAG TAACTGAGGT
6201 TAGCCTGAC CCAGGCTGTA TTTGTGATTT TTTTCATTT GTTTTTTGT ATTTTGCACC TGACCCGGG GGTGCTGGG CAGTGTATCA CTGGCCAGCT
     ATCGGGAATG GGTCCGACT AAACACTAAA AAAGTAAAA ACTGGGGCCC CCAACGACCC GTAAGACT GTAATTCAAA GGGACCTGT GACCGTGA
6301 CCCTCCCC CCTTGGTTCT CAGAAAACG GAGTTGGAT TGCTAGGGAA GTCTTGCTGG CACTTAGTGG GACCCTAAC GAATCAGAAC GTGTCTGGACA TCTACTACAT
     GGGGAGGGG GGAACGAAGA CGTGACACG GTTATTTTTC GAAATTTTT TGACATAGGA AGTGCAGTTT CCACCAACA AGGGACCTGT AGATGAGTA
6401 GGCTTCCTT CAGAAGACG GAGTTGGAT TGCTAGGGAA GTCTTGCTGG CACTTAGTGG GACCCTAAC GAATCAGAAC GTGTCTGGACA TCTACTACAT
     CCGAAGGAAA GTCTTTTC AGATACCTA TTTTCTAAA TAAGTGGAAC CCACACCTTA GTGAATCACC GTTAGTCTG GAGGTTCCC TGATTTTCT
6501 AGGGGAGACT TGCTAGTGGG CCAGGTCGG TCCAGTGTTC CCAGGCTGGG CCACCTACTT GAAAAATAA GGGGCGGAAA AGTGTAAGGT CACTTCCAG
     TCACTCTGA AGATCCAAA AGGTACAAG GTCCTAGTT CCACACTCA CTTTTAATT CCCCGCTTT TGTTTAAAC CACTTCCAG
6601 TGGGAGAATT TCATGATCGG AAAAGAATTT ATTCACCTTG CCAGGCTGGG CCACCTACTT GAAAAATAA GGGGCGGAAA AGTGTAAGGT CACTTCCAG
     ACCCTCTTAA AGTACTACG TTTTCTTAAA TAAGTGGAAC CCACACCTTA GTGAATCACC GTTAGTCTG GAGGTTCCC TGATTTTCT
6701 GTAAATCTA GCATTGAGA GTGTAGGCA AGGGATCAA CTGGCCTAGT GTGATCGTA GAGCTTGAGA GAGGTGAGA GTTAGCCTCA GGGAGATTCT ACAGGCAATG
     CATTAGGAT CGTAACTCT CGACCTCCGT GACCACACAT AGTGCAGTA CTTCATCCG CGTTGTGTAC
6801 GAGGCTTGG GACGCAGAAG TTTGTGGGTG GACCCAAGTC TCCCATCACC TCCCCGTTAC CAATGGAGT CGTTCTAGA CGTATCCCT CCCCTAAGA TGTCCGTTAC
     CTCCCGAACC ATGGGTCCC CTGGGTCTTC AAAGCACCAC TCCCATCACC TCCCCGTTAC CAATGGAGT CGTTCTAGA CGTATCCCT CCCCTAAGA TGTCCGTTAC
6901 ATGCAGAGTT CAGGGCTCC CTTGAAAGC ACTAGAGAC CCGAGCAGGT GAAGGTTAGA GTTAGGTGGT CTCTTCTAGC CCATCCCAG
     TAGCTCTCA GTCTCCGAGG GAAACTTCG TGATCTGTCG CTTCCAAATCT CAATCCACCA GAGAGATCG GGTACGGCCC
```

*FIG. 4B-7*

```
7001 CTGAGGAGGA CCCTGAGGGT TTCAGGAAGG ATCGAGAATG GAAAGCAGAG GAGAAGAAGG ATCGAGGAGG GCAGAACACA TTTCTCTTCT
     GACTCCTCCT GGGACTCCCA AAGTCCTTCC TAGCTCTTAC CTTTCGTCTC CTCTTCTTCC GTACTCCTCC CGTCTTGTGT AAAGAGAAGA

7101 TTAATAGCAA GCCTGGAAAG GATAACTTCC TCCAGGAGGA GATGCTCACC AGTGGGGTGG CTTTCGTTGC GAGAAGGGAT TTCTCCAAGC
     AATTATCGTT CGGACCTTTC CTATTGAAGG AGGTCCTCCT CTACGAGTGG TCACCCCACC GAAACCAACG CTCTTCCGTA AAGAGGTTCG

7201 CTGGGTTCC CCAATTCTCC TCTCTGTCA CATTAAGTGT GTGGTCCTTC GGCACCCTCC TGGTGAGCG AGGGCATCC AGGGCTAAAG GTGTCATCAC AACTCTATCC
     GACCCAAGG GGTAAGAGG GTAAGAGT CGAATTCACA CACGAGTTC CGGTGGGAGG AACACTTCC TGGAAGATAC

7301 CTGGAGTTCA AATTGCGTG TTAAGGAC AGGGCATCCGG AGGTGAAGG GAGTCAAGTT GGAAAGAGG TAATTAATGAGG
     GACTCAAGT AATTTTGTG TTAAACGGAC AGGGCATCCG TTAACAGCTG GCGATCTAAG GAAACAAAGT CCAAGACTTC

7401 CCATTACTGC TTCAACGCAG AGAAGGAGCT GACCGGAGT GAACAAATGA CTAAATAATG AAATACATAA AGGACAAGAT
     GGTAATGAAG AGTTGCGTC TACTTCTCT TTATTACTC TGTTTTACTT GATTATATTA CCTATTAATC TTGTAAGGAT

7501 GACTGAATGA GCAAATGCTT AAGGAGAGA CAGCAAGATC CTGAAATTT GGAGACTAAT CTTTGAGATG CATTCGAAGG GAAATCCTG
     CTGACCTTACT CGTTAGACAA ATCCTCTCT GATCTTAGA GAAACTCTAC CTCTGATTA AATTAGGATT TTCTCCTGTA

7601 GGAGGAAAAA AAGTGAAAT ATGAAGAGAG AATAGGGATG GCTTCAGAGA GGGTGCTGG CTTTGAGGT AAATACACTA AAGACAAGAT
     CCTCCTTTTT TTCACATTTA TACTTCTCTC TTATTCCCTAC CGAACCTACC GAAACATGT TTCATAATT TTCTCCTCTA

7701 TTGCAGGATCA CAAAATGGGA TAGATACTC CCCGGAAAG GTGGAAGCA CCACTCTGT GAAGCCTTCA GAGGCTTACCGG CCCGACACCA
     AACGTCCTCT GTTTACCT ACTCGAGAG GGGCCTTTC CACCTTCGT GGATTTGTC GGTCTGAAGT CTTGGAAGT

7801 CTGAGGATCA TCCGGGGGGA AGGACTATT TTCAGTTAGT TATATTAAAG CGAGATACTA CATTATCTT GGTAAGAGT
     GACTCCTAGT AGCCCGCTT TCCTGATAA AAGTCAATCA ATATAATTCC GCTCATGT GTAATAACC CCTATTGTCA

7901 AGATAATTA TTTGAACATT TTGGAACATT TCCTAGTAA AGTTTCGTT CACTTAAAGG CATTATTTGT GAATAATCT ACTAACTAAA
     TCTATTTAAT AAAGTTACCA AACTTGTAA AAAAAGTGA AGGATGACA AGAGTCATT CTTTACTGCGAGA TCATTGAATT
```

FIG. 4B-8

```
8001 AAGTAAGTAG CTTCAATTGC ATAGGCCTT AAGGACGCCC TAAAGTGCCT GTCTCCCTAA CTAAAGCAG ANTITTTGC AAAGTGAAAA
     TTCATTCATC GAAGTAAAACG TATCGGGAA CGTAAAAACCC TTGGTGCGG ATTTCACGA TGAGCCAAT GATTTCGTC TTAAAAACG TTTCACTTTT
8101 GTCAGTTTTA TTTTTGTTTG TTTGTTTCT TGTTTGGGGA ACAAACAA CGGGCCATTC CGGGCCCATT GTAGCAGAAT TGGAGGTTT CTGAAGCGA
     CAGTCAAAAT AAAACAAAAC AAAACAACGA ACAACAAAA ATTACCTTTT TGAAGTGC GCCGGGTAAG CATCGTCTA AGTCTAAAA GACTTCGCT
8201 GAAGCAAAGC TTTGTAGG TCTGACGGCA CGGGCCCA GAGGCACC TGCCGTTCCT TTATAGAACT GCAAGTAGT AGGGAACTCTA CTGAGTCCCT
     CTTCGTTCTG AAACATCCC AGACTGCCGT CTGGCTGTGG ACGGCAACGA AAATATCTTGA CGTTCAATACA TCCCTTAGAT GACTCAGGA
8301 AGGTAGTGGA GTTGACAAC AACTCCCTT GAGTTGAGAC GCTAAAACC ATCCCTTTTT GATTAGCCCA GGGAACTAA GGCTCAGACA
     TCCACTACCT CAACTGTTGG TTGAGGGGA CTCAAATCTG CGATTTTGG TAGGGAAAAA TATAAATACA CTAATCGGGT CCCTTGATT CCGAGTCTGT
8401 TGGAAATAC CACACGCAG GTGTCGGCTC CCAACTCCT AGGGAAATG AAAACTACAC TGTTGTTTT ADATATCTTG TGCTTCAAGTC TGGCCAGTGT
     ACCTATTATG GTGTCGGCTC AAGAACATG GTTGAGGGA TCCCTTTAC AAACAGACTC AGTAGAAC ACGAGTTCAG ACCGGTCACA
8501 TTGGCAGGAG TGGCCTTATT AGCGGAGGTG TACTGTGA TCACTTGGAG CCTCAGCTC GAGGTAGTA TGCTCAAGTC TGGCCAGTGT
     AACCGTCTC ACCGGAATAA TCCGCTCAC ATGGAACAAT CTCTTCACAC AGTGAACTC COGGTCCAAA ACGAGTTCAG ACCGGTCACA
8601 GATCCTTGCT GTCTGCAGAA CCTTGGTCTC TTCTGGCTTC AGGGCTAGAA CTTCTCAGCC ACCATGTCTG TGGCCAGTGT
     CTAGGACCGA CAGAGTCTT GCACGAGAGG AAGACCGACG GAAGCCTAGT TCCACATCT GAAGCGTCGG TGGTAGCGAC GGAAGAATTA
8701 GCTTTGCTTC TTTGCATGAC GATAATGAAC TGTGCCTCTG AAACTGTAAG TCACGCCCC AGTAGCATGT TTCTTTTAT AAGATTTGCA TAATGTAGTG
     CGAAACGAAG AAAGTACTG CTATTACCTTG ACACGGAGAC TTTGACATTC AGTGGGGG TCAATGTACA AAAGAAATA TTCTCAAGT ATACATAC
8801 TANTGATATA TGTATGTATA TGTATGTATA TATATATAA CAGGGTCTCA CTCTTTTAGCT TGAAGCAT GCTTCCT ACCAGTGCG TATGTAGCCC
     ATACATATAT ACATACATAT ACATACATAT ATATATATT GTCCCAGAGT GAGAATCGA GACCGACCG AGTCCGGAT ACCCAGGGG
8901 AGGATTGCCT GAACTTGAA GCAATCTTCC TGCCTTCAGCC TGAGTCACA CAAGCCATT AAACTGTATG TAGTAGCC
     TCCTAACGGA CTTGAAACTT CGTTAGAAGG AGGAGTCGG AGGAGTTACCA TAATGTCCGT ACTCAGTGTT CAAGCCATA TTTAGAATAC
```

FIG. 4B-9

```
9001 AGAAGACAGA AAATAGGAGT TCCTTTACCT AGTTCACAGA TCCCTACAAT CTAACCTCGT TGGCTTCCATA AACAGCCCTA CCCACCCCTC CTGGAACTGC
9101 TCTTCTGTCT TTTAGTCTCA AGGAAATGGA TCAAGTGTCT AGGAGTGTTA GATTGGAAGCA AGGAGGTAT TTGTCGGGAT GGGGTGGGAG GACCTTGACG
9101 TTTGAGGAAT GCTGCAGGCT CTAACGGCA CACTCCTCCT TGGTAAATCT GTTGCCTTCC CCCCACATGT CCCAGTGGCC CAAAGCCTCT
9201 AAACTCCTTA CGAGTCCGA GAGTCCGT GTGGGAAGA ACCAATAGA GAAGTCGGAC CAACGGAAG GGGGGTACA GGTACACCGG GTTTCGGAGA
9301 CATCCTGTTC TCAAATACCA CTAGCTAGTA AGGCTCCCG ACCTGACCCG GTTTAAATAT TAGAAAAGGG TCACTTTCTC CCTTCCACAG ACAAACAAAC
9401 GTAGGACAAG AGTTATTGGT GATCGATCAT TCCGAGGGC TGGACTGGGC CAAATTTATA TGTGAAAAGAG GGACGGGTC TGTGGTTTG
9501 CACCATATGC TTGTCACTTA CTACCTGACT ATGAAGGTTA ATAGATGTCT TCTCAACCTT TCTCTGACCC CACTCCATA ATGCACTGA
9601 GTGGTAACG AACAGTGAAT GATGGACTGA TACTTCCGAGT TCAAACTGGGC AGTGTTGGAA AGAGACTCGG AGTCAAAGGG GGACGGGTAT TAGCTAGACT
9701 GACACAGAAT TCCTAGAGC TGGTGTTCTC CTCATCCTGA GTGCTGGAC GTGCTGGTGA CCCTACCCAC AGGATAAAAT
9801 CTGTGTCTA AGGATCTG ACACCAAGAG GAGTGAAGGAT CACGAACCTG GGAAATGATG CAAACCACT GGTGGCTGG TGGTACTGA
9901 TATTTCATT ACTGTAAAT TTTTTCATTG TAATGTAACC AATTGTGTAAC ATTTGTGTTT CCCAGTGATC TTAGATGACC CTGGAAGA
9701 GACACAGAAT CCCAAAGGG TCCCCAACCAC AAGTAAGAA TTCTGCCAT AGGGAACAT GGATTAACAC GGGTCACTGG AATCTACTGG GACACCTTCT
9601 AGAAAGTGAA CTATGAAGTA TTGACATTAA AAAGATATC ATTACTATC TAAACACAAA GGGCTACTGG AATCTACTGG GACACCTTCT
9801 GGGTTCTGGAG GTAATGACAG GCCTTAGTC CGGAATCAC AAGGACCTG CATACTCAC CAGAACTCTC GTGTGTGT GTGTGTGT GCCCTGAGTC
9901 GGAAGCCCT CCCGGACTC GATACTGTC GAAGTAGT AGACTTAAA AACACACA CACACACA CGGGACTAG
9801 GGTGCTGGAG CTAATCGGAG GCCTTAGTC CGGAATCAC AAGGACCTG CATACTCAC CAGAACTCTC GTGTGTGT GTGTGTGT GCCCTGAGTC
9901 GTGGGGGTGG CAATAGCAGC AACAGTGAAC TAAATTTTA AGTAGAAACT CAGTGGGAGA TACAAAATT GCAGTTTGA AGTGGGGGG GATTGTTAA
```

FIG. 4B-10

```
10001 TAACTTAATA ACATAACCCA GAAGAAGGC CCCTTGGTCT ATATGCCTCA GTACAGGGGA AGCCCAAGGC CAAGAAGTGG
      ATTGAATAAT TGTATTGGGT CTTCTCTCCG GGAACCAAGA ACGTTTGAAA TATACGGAGT CATGCCCCT TCCGGTCCCG GTTCACCCACC
10101 GTAGGGGAGC AGGGTGGGGG GAGGTATAG GGAACTTTCC GGATAGCATT TGAAATGTAA ATGAAGAAAA TATCTAATAA AAATTTGAAA CAATTTTTTG
      CATTCCCCTCG TCCCACCCCC CTCCCATATC CCCTGAAAGG ACTTACATT TACTTCTTTT ATAGATTATT TTTAAACTTT GTTAAAACC
10201 CCCCAGTTTG GCCTGATTC CACTACCTCA ACCAGACTGG CATGTGACTC TGCTGAGATC TGCCTCCTG GTCAGAGAAGA CAATTTTTGG
      GGGGTCAAAC CGGACTAGA GTGATGGAGT TGGTCTGACC ACGACTTCAG ACGATGAAG CAGGTCTTCT GTTAAAAACC
10301 AGTTAGTTTC TCTTCTTCCA TCTTGAGATT GAACTCGGGT CATCACGGCT TGCAGGAAGT GACTACTTA GGGTCTTCCC AGACCCTCTC
      TTCAATCAAG AGAGAAGT AGAACACTA AGTCGCCCA CGTAGCTTCA CCGAACTTCA CCGAATCAAT CCAACAGAGG TCTGGGAGAG
10401 GGTTGATTA GTAGATCCT GCACTCATC CTGACTTTC GATAGACCAA TGTCTAATAC ATGAATGTTA TATCAAGAGC
      CCAAACTAAT CAATCACAA CGTGAAGTAC GGACTCAAG CTGAGTACAT ACAGATATTG TACTATACAT ATAGTTCTCG
10501 CAAGTGATGA GATGGCTCAG CACAGAACTGC TCTTCCAAAG GTCCGAAGTT CAAATCCCAG CAGGGCTCAA GTTAGTGTGT AAGGAGAAAT
      GTTCACTACT CTACGAGTC ACCATTCTC GTGTCACGAC AGAGGTTTC CAGTTTCAAGT TTAAGGGTC GTTAGGGTC CACGAAGGT AAGGAGAAAT
10601 TGGAATGTCT GAAGACTCT ACAGTGTACT AAATAAAATAA ATCTTAAAAA AAAAAACCC AGCCGGTGT GCCTTTAATC
      ACTTACACGA CTTCTGACGA TGTCACATGA ATGTATATTA TTTATTTATT TAGAATTTTT TGGCCCGCA CGAAGCCTG
10701 CCAGCCACTG GGGGCGAGG GCAGAGGGAT TCCTGAGTCC GAGCCCAAGC TGGCTCAAGC AGTAGTTCC AGACAACCAA GAACTACACA GAGGAACCT
      GGTCGTGAAC CCTGGGTCTC CGTCGCCCTA AGGACGCTCA CTCCGGTGG ACCGAGTTCG CAGTCGAGT TCTTGGAAGC CTCGTTGGA
10801 GTCTCGAAAA AAAAAGAGA GAGAGGGAAG TGAGACCCA AAAATCTAA CATTTCCTCT GTGTCTTG TTCTTGATAAG CAATGCTGGC
      CAGAGCTTTT TTTTCTCT CTCTCCCTTG ACTCCGCGT TATAGAGAAT GTAAGACAC CAACGAAAC GACATCAGAT AAGACTAATTC GTAAGACCG
10901 TGGCTCCCAA GGTAGGAAGT AACATTTCTT TATAAAGGT ATTGCCTCTG ATGGCTGTG AGATGGGAAC CCAGGGACCT
      AACGAGGGTT CCATCCTTCA AACATTCCA TTGAAAGAA TAAAGCACGAG CAAATAAAAA GCAATAATAA ATACCAGCG TCTACCTTG GGTCCTGGA
```

*FIG. 4B-11*

11001 TGGCAAGCAA GGCTAGCTGT TTACCACTGA GCCATACTCC AGCCTTCCAC TGGGGATTC TAGGCAAGGG TTCTACCACT GAGCCAACT CCCCACCCCC
ACCGTTCGTT CGGATCGACA AATGGTGACT CGGTATGAGG TGGGAACGTG ACCCCCTAAG ATCCGTTCCC AAGATGGTGA CTCGGTGTGA GGGGTGGGG
11101 ATCCCTCTCT GGAAGTTCCT AGGCAGTTCC ATACCTAGCC TTTGATCTTT TAAGACGGTC TTACTAGAGC TCAGTT
TAGGGAGAGA CCTTCTAAGA TCCGTCAAGG TATGGATCGG AAACTAGAAA ATTCTGCCAG AATGATCTCG AGTCAA

*FIG. 4B-12*

```
  1 AAGCTTGCAGGAGGAGGTAGGAGGCAGCTTGGGCGTTGATTCAATGCAGCTTCGGATGAGATCGGGTCACCAGTCAAAAACTGTGAGCTTGA
 91 TTCGAACGTCCCTCCGTCGGACACCGCAACTAAGTTACGTGGACCCGGAATAGGAGCCTACTCTCAGTGGTCAGTTTTTGACACTCGAACT
181 TCCAGAACCACGAATTGTAGATAAAAATGTTTAGAATAAAATCGTTGAATCTTTATAAACCTTTCGATGAATTTGAAGATTTGAGGGAGAGG
271 AGTTCTTGGGTGCTTAACATCTATTTTACAAATCTTATTTTAGCAACTGTGAAATATTGGAAAGCTACTTAAACCTTCTAAACTCCCTCC
361 ACACTATGAGAATGTTACATTTTCTATTCAGTAATAATTCAATGCTTAGAACAGATGAAAAATAACAAACCAAACAAATAAAATCCGCCATCACAGAGTGCTCCTAAATGGAC
451 TGTGATACTCTTACAATGTAAAGATAAGTCAATAAAAACTCGTCATTTGTCTCACTTAGTGTTCCTTATACGGGTAGTGTTCACGAGGATTTACCTG
541 TTGCTTGTTATTCATTTACAGTGTGGCCCCTTTGACTTTCATCGGACTCCTAGCAGAGAAAACAAAATCCGCCAGATGGAGCTGGAGATGGCTCAGCTGT
631 AACGAACAATAAGTAAATGTCACACCGGGAACTGAAAGTAGCCGTTGAGGATCGTCTTTTTGTTTAGGCGGGTCTACCTCGACCTCTACCGAGTCGACA
721 TAAGAATACTTATCCTACACAGGCCCTGGAGCCACCACACGGTTCCAGCACCATCGTAACTCCAGTTCTAGGAGACCTCC
811 ATTCTTATGAATAGGATGTGTCCGGGACTCGGTCAAGGTGGTGCCACCGAGTGTTGGTAGACATTGAGGTCAAGATCCTCTGGGCTGAGG
```

```
1010        1020        1030        1040        1050        1060        1070        1080        1090        1100
TGGGCTGTGAGACGCCCACTGTGGGTGCTCGGAAACCAAACTCGGGTCCTCTGGAAAGACAGCACCCATAATGCAGAGGTATCTCTCAGAGACTCTACT

ACCCGACACTCTGCCGGGTGACACCAGACCCTTGGTTTGAGCCCAGGACACCTTCTGTCCGCCTCGGGCTATTACGTCTCCATAGAGAGTCTGAGATGA
1110        1120        1130        1140        1150        1160        1170        1180        1190        1200
TTAAAATTTCAATTTATCTTTTTTTTTTTTAAAGTAACTATAGGAAAGTACATGGGTATATAGATCCCAGTACCAAGATTCTTCCTTTGCAG

AATTTTAAAGTTAAATAGAAAAAAAAAATTTCAAGGTTCATTGATATATCCTTTCATGTACCCATATATCTTAGGGGTCATGGTTCTAAGAAGGAAACGTC
1210        1220        1230        1240        1250        1260        1270        1280        1290        1300
GTAGCACAACTTGGTCTGCTTCACATAAAGAATGAAAAGTTCATTCACAGAGTAAGTACTCTGACAATCTTGAACTTGAACCAACGAAGTGA

CATCGTGTTGAACCAGAGAAGTGTATTCTTACCTTTCAGTAATTTTGTGTAGTGTGACATTTCATCTTAACTTGAGACTGTCTTGTTCGCTTCACT
1310        1320        1330        1340        1350        1360        1370        1380        1390        1400
GTCTGACTTCCAGGTAACTGAGCCTTCTTCCTCCTAAAGACACCATAAAATAAACTTGGGCATGGTGAGAAGGAAACAACGCAGG

CAGACTGAAGGTCCATTGACTCGGAAGAATTCTGTGTTCGGTATGTGTCTCATTTTATTTGAACCCGTACCACTCTTCCTTTGTTGGTCC
1410        1420        1430        1440        1450        1460        1470        1480        1490        1500
AGGGCTAGCAAGTCTGAGAGTCGTGAGTGTGCTCGGTTTATAAACGGAGCCCACCTTGCCAGGAGGTAGTCACATGCTCTGCTAAACAGAAAACTTAAG

TCCCGATCGGTTCAGACTCTCAGCACTCACGAGCAGCCAAATATTTGCCTCGGGTGGAACGGTCGCCTCCATCAGTGTACGAGACGATTGTCTTTGAATTC
```

FIG. 5C

```
1510        1520        1530        1540        1550        1560        1570        1580        1590        1600
AAAACACTTACACGAAGCAAACATGGGGAAGTGCCAATGCAAGTGACTGGTGGCAATGACCGAAATGACCACAGCAGCCACTAGAAAAGGAAGGT
TTTTGTGAATGTGCTTCGTTTGTACCCCTTCACGGTACGTTCGTACACTGACCACCGTTACTGGCTTGGGTCGTCGGTGATCTTTTCCTTCCCA 1610        1620        1630        1640        1650        1660        1670        1680        1690        1700
AGTGCGCCACACTGTAGTGTGAAAATGAACTTAATCATTTATTTGAAAAACGTGTAAGCAAAGATGTCTTCTTCCACTTCCTTTGCGCAGG
TCACGCGGTGTGACATCACACTTTTACTTGAATAAGTAAATAAAACTTTTTTGCACATTCTTTCGTTTCTACAGAAGAAAACGCCGTCC 1710        1720        1730        1740        1750        1760        1770        1780        1790        1800
CGAGCACTTCCTGGAATTTATAAAGTGCGATCTTTCTGGGGACTTCTCATAACATTTCCTACTCTATGTCTGTCAAATAGAGAATGCTCTTG
GCTCGTGAAGGACCTTAAATATTTCACGCTAGAAAGACCCCTGAAGAGTATTGTAAAGGATGAGACTACAGTTTATCTCTTACGAAAC 1810        1820        1830        1840        1850        1860        1870        1880        1890        1900
AACAAGTGTGTGTGTGTGTGTGCGCGCACGGCACTCACTCCTGCTCTGTTGAGGTCCAGTTTTGATGGTCCCGCCAGAGGTATATTTGAGTAT
TTGTTCACACACACACACACGCGCGTGCCGTGAGTGAGGACAACTCCAGGTCAAAACTACCAGGGCGCTCTCCATATAAACTCATA 1910        1920        1930        1940        1950        1960        1970        1980        1990        2000
CATTTCTCAAGAGCTTCAGCTGGGAGAGACTGCCTCTTACTGGCCTGATTCATCTCCGTTTGGGCTGGCGGCGCCTTGGGATCCTC
GTAAAGAGTTCTCGAAGTCGACCCTCTGTGACGGAGAATGACCGGACTTCCAGTGATCGACTAAGTAGAGAGGCAAACCGACGCGGAACCCCTAGGAG
```

FIG. 5D

```
2010       2020       2030       2040       2050       2060       2070       2080       2090       2100
CTATCTCTTCCTTCCCCAGTGCTGCTGGGATAACAAGGTTGGCACCACATGAGCCTTTTAAAAATGTGAAGTTTGGAAACGCAGGTTTTCATGCTTGCAC
GATAGAGGAAGGGGTCACGACCCTATTGTTCCAACCGTGGTTGTACTCGGAAAAATTTTACACTCAAACCTTCGAGTTTGCGTCCAAAAGTACGAACGTG 2110       2120       2130       2140       2150       2160       2170       2180       2190       2200
TGAAACTTCACAAGCTGAACCGTCTCCCTCTCCTTCCCTTTCTTCCTTTTTAAAACACATCTGTCTTTAAAAAAAAAAGG
ACTTTGAAGTGTTCGACTTGGCAGAGGGAGGAAGGAGAAAAAGGAAAAGGAAACAGAAATTTTTTTTTTCC 2210       2220       2230       2240       2250       2260       2270       2280       2290       2300
CCCAAAACAAGTGTAAAGTATTTCCTTATGTGTGTGGAGGGAGGAGTAGAGGCTGATTTCACTGAGAGTCCTGTTAAATTTGGGTGCCATAGCCAAT
GGGTTTTGTTCATTTCATAAAGGATACACACACTTCCCCTCCAATGATCTAGGACAATTTTAAACCACGGTTTATCGGTTA 2310       2320       2330       2340       2350       2360       2370       2380       2390       2400
CAAAGACCCATCGTTCCTCTAAGAATTCTAAATGGGGCGATTACCAGGTTCTGGTTTGTTATTAGAGGAGACACTGTCTTCTTAAGTAAA
GTTTCTGCGTAGCAAAGGAGATTCTTAAGATTTACCCGCGACGTCCAAGAACATAATCTCCTCTGTGACAGAGAATTCATTT 2410       2420       2430       2440       2450       2460       2470       2480       2490       2500
ACATAGAAGGGAAGTGTCCAGAAATTGTAAATAAGGCTTCGAGAGAAGCCTTGTCTGCGGCCACGGGGATGGAGAAGACTACCTTCGCCTATCCAGGATCC
TGTATCTTCCCTTCACAGTCTTAAACATTTATTCCGAAGCTCTCTTCGGAACAGACCGGTGCCCTAGCTCTTCTCTGATGGAAGCGGATAGGTCCTAGG
```

FIG. 5E

```
2510       2520       2530       2540       2550       2560       2570       2580       2590       2600
ATCGTCCCTCCTCTACCAGATCTGACAGCCCTCCTGAGGCTCTCTTTGCTGAGGTTTGTTTTTACTCTCTGAGGAAGTTTCCTTAAAC
TAGCAGGAGGAGATGGGGTCTAGACTGTCGGGAGGAACCGAGAAAAACGACTCCAAACAAACTCAAAATGAGACGTTCTCTTCAAAGGAATTTG 2610       2620       2630       2640       2650       2660       2670       2680       2690       2700
ATTCTACCCTGTTCACAAGTAAATACACCTCTTAGCTAAGAGGCCACACCAAGGGAATAAAAGAACAAGCCAGAGAACCTTCAGAAGCTGT
TAAGATGGGACAAAGTGTTCATTATTATGTGGAGAATCGATTCTCCGGTGTGTGGGTCCCCTGTGGCTCTTGGAAGTCTTGCGACA 2710       2720       2730       2740       2750       2760       2770       2780       2790       2800
CGATAGGTACACCAAGCAGCCTTCATACGGAGAGTTTTCATTCGTGAGGAGCTGAATATACAACAAAGCTAAATGTGAGCAGACCAGGCATGCCTCTGCTAA
GCTATCCATGTGGTTCGTCGGAAGTATGCCCTCAAAAGTAAGCACTCCTCGACTTATATATGTTCGATTTACACTCGTCGGTACGGAGACGATT 2810       2820       2830       2840       2850       2860       2870       2880       2890       2900
ATGAGGATGCCACCAAGACATGCCCAAGATCTTCAAGTATAATTTTATTATAGATTCGCTATGTGTTGACATGTTTTATAGTGAACCTGGAATTTT
TACTCCTACGGGTGTGGTTTGTACGGGTTCATTATTAAATATATATCTAAGGATACACAACTGTACAAAAATATCACTTGGACCTAAA 2910       2920       2930       2940       2950       2960       2970       2980       2990       3000
ACAAACCCTCCTGGTTTGCCACCTTGCTTCTGGCACCATACTTGAGGCTAGGCAGCATGCCTGTTCCCCCTTATTTTTTTAAAGA
TGTTTGGGAGGACCAAACGGTTGGACGAAGACGTTGGTATGAACTCCGAATCCGTACGGACTATTTCCTCGTACGAAGGGAATAAAAAATTTCT
```

FIG. 5F

```
3010       3020       3030       3040       3050       3060       3070       3080       3090       3100
AAAGCACCAATGTTACATCATTAATCATGCATATCAGTTAGTTAGATCCGATGTAGACAATAATCTTATCTCTTTGTCTGGCTGAAAGACTGTCCTT
TTTCGTGGTACAATGTAGTAATTAGTACGTATAGTCACATCAATCTAGGCTACATCTCTGTTATTAGAGAATAGACAGACCGACTTTCTGACAGGA 3110       3120       3130       3140       3150       3160       3170       3180       3190       3200
TAAACTATCATTCTAAATGCATTTGGTTTTTTGCCAGGAGTAAAACATGTCACAAGATATTTGTTGTCATTTTCCAGGAAGGAAAGGAATGGAAAG
ATTTGATAGTAAGATTACGTAAAACAAAAACGGTCCTTCATTTTGTACAGTGTTCTATAAACAACAGTAAAGGGTCCGCACTTCCTTCCTTACCTTC 3210       3220       3230       3240       3250       3260       3270       3280       3290       3300
AAAACGAGGGGGTGAAGCTGCTCTGTTCCTCTCTAGTCGGCTACTTGAAGTCTACATAGCCTGGGGGACAGTGTTCACATGGGACCGGGTTTCCTCT
TTTTGCTCTCCCACTTCCGACGACAAGAGATCAGCGATGAACTTCAGATGATGTATCGACCCCCCCCTGACAAGTGTACCCTGGCCAAAGGAGA 3310       3320       3330       3340       3350       3360       3370       3380       3390       3400
TTGTTCCTACACTGGCGCTCTGGCAAGAAACTCTCCCTTCTCTTCCCCAAGCATATCTTGGCTGAAAGGTCAGCTCTGAAAAGGGCCTGGCCAAAG
AACAAGGATGTGACCGCGGAGACCGTTCTTTGAGAGGGGGTTCGTATAGAACCGACTTTCCAGTCGAGACTTTTCCCCGGGACCGGTTTC 3410       3420       3430       3440       3450       3460       3470       3480       3490       3500
TTACTGTAGGGGACCGTGGTCATGGAACTGGGTAGACAAAGCACTCTAGGAGAAGGACCGGAAGCCAGCCACTGGACCTTCTCTGTGCATTTGCCCTTGGAG
AATGACATCCCTGGCACCAGTACCTTGACCATCTGTTTCGTGAGATCGTCGGTGACCTCTTCCTGGCCCCCGAGAAGAGACAGTAAACGGGACCTC
```

FIG. 5G

```
3510      3520      3530      3540      3550      3560      3570      3580      3590      3600
CCCTGACCACGCCAGCTCCCTGCAGCATCTCCTTGCTATGGGTTTTCTTGGACCGAGCCAGGAGAGTTCACAACCGAAAGTCTTCTAGGCTAATCAGGT
GGGACTGGTGGCGGTCGAGGAACGTAGAGAGAACGATACCAAAAAGACCTGGCTCGGTCCTCAAGTGTTGGCTTTACAGAAGATCCCGATTAGTCCA 3610      3620      3630      3640      3650      3660      3670      3680      3690      3700
AACTTCGACGATTTAAAGTTGCCAGATGGACGAGAAAACAGTAGAGGCGTTGGCAACCTGGATAAGCGCCTATCTTCTAATTAAAACATTCAGACGGG
TTGAAGCCTGCTAAATTCAACGGTCTACCTGCTCTTTTTGTCATCTCCGCAACCGTTGGACCTATTCGCGGATAGAAGATTAATTTTGTAAGTCTGCCCC 3710      3720      3730      3740      3750      3760      3770      3780      3790      3800
CGGGGGATG-CGGTGGCCAAAAGCACCATAAAACTTCCAAGTACTGACCAACTCACTGCAAGAGTTTGTGCCCGAGTACATCTAGGTTGTCAGGGTCT
GCCCCCTAC-GCCACCGGTTTCGTGGTATTTTGAAGGTTCATGACTGGTTGAGTGACGTTCAAAACACGGGCTCATGTAGAATCCAAGTGCCCAGA 3810      3820      3830      3840      3850      3860      3870      3880      3890      3900
TGTCTTCATGCTCTCCCAACTGCGGGCCAGTTTTTGGTTCCCTTGGACTTTCAGTGCAGGCGGCGAAGAGTTCTGCCACTTGCAGGCCTCCTAATGAGGGGC
ACAGAAGTACGAGAGGGTTGACGCCCGGCCTAAAAACCAGGAAGCCTGAAAGTCACGTCCGCGCTTCTCAAGACGTTCCGAGGATTACTCCCGCG 3910      3920      3930      3940      3950      3960      3970      3980      3990      4000
AGTGGGCCTCGTGTTTCTTGATGCTTCCCAGTTGCTGGGGCAGCAAGTGTCTCAGAGCCCATTACTGGCTACATTTTACTTCCACCAGAAACCGAG
TCACCCGGAGCACAAAGACCACTACGAAGGGTCAACGACCCCGTTGTTCACAGAGTCTCGGGTAATGACCGATGTAAAATGAAGGTGGTCTTTGGCTC
```

*FIG. 5H*

```
4010       4020       4030       4040       4050       4060       4070       4080       4090       4100
CTGCGTCCAGATTTGCTCTCAGATGCGACTTGCCGCCCGGACACAGTTCCGGGCACGCGGGAGTGGGGCGTGGGGGAAACCCAAAACCTGGTATC
GACGCAGGTCTAAACGAGAGTCTACGCTGAAACGGCGGGCCCCATCACCCCTTTGGCCCCTTTGGGTTTGGACCATAG 4110       4120       4130       4140       4150       4160       4170       4180       4190       4200
CAGTGGGGGCGTGGCCGGACAGGGAGTCCCACCCCGGTAATGACCCCCATTCGCTAGTGTGTTAGCCGGCTCTCTTTCTGCCCTGA
GTCACCCCCGCACCGGCCTGCGTCCCTCAGGGGTGGGGAGGGCCATTACTGGGGGTAAGCGATCACACATCGGCCGCGAGAGAAAGACGGGACT 4210       4220       4230       4240       4250       4260       4270       4280       4290       4300
GTCCTCAGGACCCCAAGAGAGTAAGCTGTGTTTCCTTAGATCGGCGGCTACCCGGCAGGACTGAAAGCCCAGACTGTGTCCGCCAGCCGGGGATAA
CAGGAGTCCTGGGGTTCTCTCATTCGACACAAAGGAATCTAGCCGCGCCTGGGCACTTTCGGGTCTGACACAGGGGTCGCGGCCCTATT 4310       4320       4330       4340       4350       4360       4370       4380       4390       4400
CCTGGCTCAGGACCCGATTCCGGGACACGCTGCAGCCGGGCTTGGAGCCAGGGGCCGCCGGTGCCGGCGCTCCCCGGTCGCTTCCGGGGCGGCATAC
GGACCGACTGGGCTAAGGCGCCTCGTGTGGCGACGTCGGCGACCTCGGTCCCGGCGCCCGAGAGGGCCAGAACGCGAGACGCCCCGCGTAT 4410       4420       4430       4440       4450       4460       4470       4480
CGCCTCTGTGACTTCTTTGCGGGCCAGGGACGGAGAAGGAGTCTGTGCCTGAGAACTGGGCTTCTGTGCCCAGCGCGGAGGTGCAGATG
GCCGAGACACTGAAAGAAACGCCCGGGTCCCTGCCTCTCCTTCCTCAGACACGGACTCTTGACCCGGAGACACGGGTCGCGCTCCACGTCTAC
```

FIG. 5I

| VEGF | VEGFR2 | Tie2 |
|---|---|---|
| Screening primers | Screening primers | Screening primers |
| Primers: VF1-VR1A<br>Product size: 0.69Kb | Primers: KF1-KR1<br>Product size: 0.45Kb | Primers: TF3-TR1<br>Product size: 0.45Kb |
| PCR program | PCR program | PCR program |
| Hot start | Hot start | Hot start |
| 94°C 40 sec<br>65°C 1 min 30 sec<br>72°C 1 min 30 sec | 94°C 40 sec<br>58°C 1 min 30 sec<br>72°C 1 min 30 sec | 94°C 40 sec<br>58°C 1 min 30 sec<br>72°C 1 min 30 sec |
| 40 cycles | 40 cycles | 40 cycles |
| Confirmation primers | Confirmation primers | Confirmation primers |
| Primers: VF2-VR2<br>Product size: 0.98Kb | Primers: KF2-KR2<br>Product size: 0.58Kb | Primers: TF2-TR1<br>Product size: 0.47Kb |
| PCR program | PCR program | PCR program |
| Hot start | Hot start | Hot start |
| 94°C 40 sec<br>65°C 1 min 30 sec<br>72°C 1 min 30 sec | 94°C 40 sec<br>65°C 1 min 30 sec<br>72°C 1 min 30 sec | 94°C 40 sec<br>58°C 1 min 30 sec<br>72°C 1 min 30 sec |
| 40 cycles | 40 cycles | 40 cycles |

FIG. 6

```
  10         20         30         40         50         60         70         80         90        100
AAATGTGCTGTTCTTTAGAAGCCACTTCTGCGCTTCAGATTACAAAAGGAAGTCTGGTACACAGCCATGATAAAAGACAATGGGACGGGGTCAC
TTTACGCGACGAAATCTTCGGTGACGAGTCGAAGACGTCTATGGTTTCCTTCAGACCATGTGTCGCGTACTATTTTCTGTTACCCTGCCCAGTG 110        120        130        140        150        160        170        180        190        200
AGTGGCTCCCGTCCCTTTCAGGGGTATGGAAGACGAGCTGTAGAGAATGTCTCCAGGAGTTTCATTAATCAGCAAATTTAGTCAGATCTGTCATCCTA
TCACCGAGGGCAGGGAAAGTCCCCATACCTCTGCTCGACATCTCCTACAGAGGTCCCTCAAAAGTAATTAGTCGTTAAATCAGTCTAGACACGTAGGAT 210        220        230        240        250        260        270        280        290        300
TGCTTTACAAGAAATGTCAGTGGGCCTGAGATCATCAGATGGAAGGTTCATCGGGTTTCAAGTCCCGTTATCCTTTTTGTAAGACCTTGAAGTTGGCAACGC
ACGAAATGTTCTTTACAGTCACCCGGACTCTACCTCCAAGTAGTAGTCAGCCCAAAGTAATCAGGCATAGGAAAACATTCTGGAACTTCAACCGTTGCG 310        320        330        340        350        360        370        380        390        400
AGGAAAACAGGAACTCCACCCTGGTGCCGTCGTGGAATTGCAGAGACTGTGTTGTTGGGTTGACCAATCTGCCCATTCTTCCTGTTATGACAGAGCTTGTGAAC
TCCTTTTGTCCTTGAGGTGGGACCACGGCACTTAACGTCTCGACAACACACCTGGTAGACGCGTAAGAAGGACAATACTGTCTCGAACACTTG 410        420        430        440        450        460        470        480        490        500
TTTAACTGGACTGGGCAAAGTCAATCCAACCTTTATACAAATGAATTGCTGAAGAGGCCTTTTAAAACTTGGAGTGTGCATTGTTTATTGGAAGGGCTTTT
AAATTGACCCTGACCCGTTTCAGTTAGGGTGGAAATATGTTACTTACTTAAGGACTTCTCCGAAAATTTTGAACCTCACACGTAACAAATACCTTCCCGAAA

510
CCTATTGGATC
GGATAACCTAG
```

FIG. 11

```
  10         20         30         40         50         60         70         80         90        100
GGTACCAAAGCATAGAACTACAGATCCGCTTCTGCCTGTACCACCCTCTGGCATTAATCACACAATGCTTGGTTTTGTTTCTTCAACTTTTCCTGTTAT
CCATGGTTTCGTATCTTGATGTCTAGGCGAGAGACGGACATGGTGGGAGACCGTAAATTAGTAGTGTTACGAACCAAAACAAGAAGTTGAAAAGGACAATA 110        120        130        140        150        160        170        180        190        200
GATGCAGTCCCTGGCTTGTGTAACTATGAGCTTCAAAAGCAATCATTCATCTCTTCTTCCAAGGACTTAGTGTATCACTTACTG
CTACGTCAGGGACCGAACACATTGATACTCGAAGTTTCGTTTCTTGCGTAGTAGATAAAACACAGAGAAGAAGGTTCCTGAATCACATAGTGAATGAC 210        220        230        240        250        260        270        280        290        300
GCTAAATGCTTGAGACAAAAAACAGGATTAATGAAGAAAAGGAAAAGTGCCCACAATTACTGACAGGGTTTCAGTAAAGCAGT
CGATTTACGAACTCTGTTTTTGTCCTAATTACTTCTTCTTTTCCTTCCCCTTCACGGGTGTTAATGACTGTCCCAAAGTCATTTCGTCA 310        320        330        340        350        360        370        380        390        400
CTAGAGGGTCAGTATTTTCCATAGCCATGCCCCAGAGTGGGGTGTTGCCACTTAGCTGCCCTGGTCTGGCTGAAGGCCAGGACTTGATTGGCC
GATCTCCAGTCCATAAAAGGTATCGGGGTCACCCAGATGGGGATCGAAATGACGGGACCAGACCGACTTCCGGTCCTGAACTAAACAACTACCGG 410        420        430        440        450        460        470        480        490        500
CTTCCTTTGCTGCTAGTCACTGTTAAGTACTGCAGAATTTACAGAAAGCTTCATGGAGGTCGTAAGAAGCCACCAAAGATTTAGAGCCA
GAAGGAAACGACGATCAGTGACAATTCATGACAGTCACTCCAGAGACATTCTTCCGGTCTCCACTATTGTGGTTCATAAATCTCGGT
```

FIG. 15-1

```
CTGACCAGAGAATGCAGAATGTCCAGGCTATGATCCAGATCCTGACTACTCAAGACTGGTTGAAGGCAAGGTTCACTTGACT
     510       520       530       540       550       560       570       580       590       600
GACTGGTCGTCTTACGTCTTACAGGTCCGATACTAGGTCCAACATCTAGACTGATGAGTTCTGACCAACTTCCAAGTGAACCTAAGTGA
CTATTTGCCAGCAGATGTTTTAAATCCATCATATATATATATATATCTCCATTACTTTTAGGACAGTGGTTCTCAGCTTCCTAAGCCCTTTAA
     610       620       630       640       650       660       670       680       690       700
GATAAACGGTCGTCTACAAAATTTAGGTAGTATATATATATATAGAGGTAATGAAATCCGTGTCACCAAGAGTCGGAAGGATTACGACATCGGGAAATT
TAGAGTTCCTCATATATTGTGATTGTAAAAATTATTTTGTTGCTACTTCATGACTAATTAATTTTTGTTGAAAGGGGTCATTTTTACCCCAGGCTGTGAGACC
     710       720       730       740       750       760       770       780       790       800
ATCTCAAGGAGTATAACACTAACACATTTTAAAACAACGATGAAGTAAAACGATGACACTTTCCCAGTCAAAATGGGGTCCGACAACTCTG
CACATGTTGGGAACCACTACTTTAGAAGGCCATGGGGTTGGAGAACATGAAAGATAAGAAGTAACAGTGTCAGTTTTTGGTTCATTATACACAGAAAC
     810       820       830       840       850       860       870       880       890       900
GTGTACAACCCTTGGTGATGAAATCTTCCGTAACCCAACCTCTTCTTGTACTTGTCACCAGTCAAAACCAAGTAATAATAGAGTGTCTTTG
ATTCACTTTAAGGTTTCAGCATGTTTGTTGTTGTATATGTGATTGGTTAAAGACTTTCTTTAATCACCATACCTAACATCTTCACCACTC
     910       920       930       940       950       960       970       980       990       1000
TAAGTGAAATTCCAAAGTCGTACAACACATATACACTAACACATTTCTGAAGTGGTCCAGAGAAAGAATTAGTGGTTATGGATTGTAGAAGTGGTGAG
```

FIG. 15-2

```
1010      1020      1030      1040      1050      1060      1070      1080      1090      1100
CATATCCATCAGCTTCACCTTGTACTCTAGCATTGGGCATTCATCCTACCAGGCATCCATTCTTTTGCAACTCACATTGTTTCCTAGTTTG
GTATAGGTAGTCGAACATGAGATCGTAAACCCGTAAGTAGGACATGGTCCGTCCGTAAGAAAACGTTGAGTGTAACAAGGATCAAAAC 1110      1120      1130      1140      1150      1160      1170      1180      1190      1200
ATTATTACCAACAATGCTTCTAGACCATGAATTTTGGTCTTTGACTTTGGTAAACATCATATAAAACAATCCAGTGGTGGGTGCCGCTG
TAATAATGGTTGTTACGAAGATCTGGTACTTAAAACAGAAAACGAACCATTGTAGTATTTTGTTAGGTCACCACCACCACGGCGACGAC 1210      1220      1230      1240      1250      1260      1270      1280      1290      1300
CTGGTGGCTGGTAAAGCAGGAAGCCATAAAGTGCCTTATTCAATCTGTTATTGATACAAAATTGTTATTTCTTCCATGTAAAGATATGGCATCTGA
GACCACCACCATTTCGTCCTTCGGTATTCACGAAATAAGTTAGACATAGTGTTAACAATAAAAGAAGGGTACATTTTCTATACCGTAGACT 1310      1320      1330      1340      1350      1360      1370      1380      1390      1400
AGTGTAGAGGTCTGAATTCAAAACCTCACATCACCAGATAGTATATTACACAAATAATACACGGCTTTGCCTGACTTCAAAGCCCTGTTCTTGA
TCACATCTCCAGACTTAAGTTTGGAGTTGTAGTGGTCTATCATATAATGTCTGAGTTGTTTATTATTGTGCCGAAACCGACTGAAGTTTCGGACAAGAACT 1410      1420      1430      1440      1450      1460      1470      1480      1490      1500
CGTAAGTATATGAGTAACAATGGTAGCACCTTAGTTTTTATCAGTTCACTAAATATTTATATAAGACCTACTATGAAGGGAGATAGAAGGGTATGAGGTG
GCATTCATATACTCATTGTTACCATCGTGGAATCAAAATAGTCAAGTGATTTAATATATTCTGGATGAATACTTCCTCTATCTTCCCATACTCCAC
```

FIG. 15-3

```
1510      1520      1530      1540      1550      1560      1570      1580      1590      1600
GGGTCATGGGAATAGAAAACGGGTGGAAGGGAGAAGGAGAATTAACTAATTTATGTTTGAAAAATGCCACAATGAAAACCTAATTTACAAAAGAACC
CCCAGTACCCTTATCCTTTTGCCACTTCCCTCTTCCTTAATTGTTTCGATTAAATACAAACTTTTACGGTGTTACTTTGGATTAAATGTTTTTCTTGG 1610      1620      1630      1640      1650      1660      1670      1680      1690      1700
ACTATATGACCTTCACAGTGTGTGCTAAGTCTTGGAGATTTAGTTGGTGAAGAAGTCAGGTGTGTTTCCAAATCTCATGGAGGATGTAATCAGTAGAGC
TGATATACTGGAAGTGTCACACGATTCAGAACCTCTAAATCACCACTTCTTCAGTCCACACAAAGGTTAGAGTACCTCCTACATTAGTCAAATCTCG 1710      1720      1730      1740      1750      1760      1770      1780      1790      1800
ACAGGAGCACATAAAAAGATAGGCAAAAATGTATGATTAGTACCATGTAAGATATGAAGGGGAACACAGAAACTAGTGGGAGACCTAATTAGTTTGA
TGTCCTCGTGTATTTTTCTATCCGTTTTTACATACTAATCATGGTACATTCTATACTTCCCTTGTCCTTTGATCACCCCTTGGATTAAATCAAACT 1810      1820      1830      1840      1850      1860      1870      1880      1890      1900
GTGGTCTTCAAAGACCCTTTAGAAGCTGAGAACTAAAGACAAGCAGCATCTCCACCTTTCCAGTGGAATGAGCAACTTAGGGTATA
CACCAGAAGTTTCTGGAAATCTTCGACTCTTGATTCTGTTCGTTCAGCTCGTAGAGGTGGAAAGGTCACCTTACTCGTTGAATCCCATAT 1910      1920      1930      1940      1950      1960      1970      1980      1990      2000
CAGCTGATTCCAACATTGTCAACAAGGCTCTTCAGAGATGACACTAATGACCAGCTTTTAAGGAAGGTTTCTGAGCATGTCCAAG
GTCGACTAAGGGGTGTAACAGTTGTTCCGAGAAGTCTCTGATCTCGTATGGGTCGAAAATTCCTTCCAAAGACTCGTACAGGTC
```

FIG. 15-4

```
2010       2020       2030       2040       2050       2060       2070       2080       2090       2100
CACCCTACACTAGGCATTGGAAATCAACATGTCCAGAGATGGAAGTGACAGTCAGCCAACCCTTTTCAAAACTTCAAAGCTATTACTCGTCAACT
GTGGGATGATCCGTAACCTTTAGTTGTACAGGTCTCTACCTTCACTGTCAGTCATTCGGTTGGGAAAAGTTTTGAAGGTTTCGATAATGAGCAGTTGA 2110       2120       2130       2140       2150       2160       2170       2180       2190       2200
CTCCAGACATATGGGCCCCGAGTGTGTTGGGAAGCTCTCATTATTGTTCTTTGATTGGTTTTCCGAGATCCAAGGAGCAGTTATCTCAGGTAG
GAGGTCTGTATACCCGGGGCTCACACAACCCTTCGAGAGTAATAACAAGAAACTAACCAAGAGATGTAAGGCTCTAGGTTCCTCGTCAAATAGAGTCCATC 2210       2220       2230       2240       2250       2260       2270       2280       2290       2300
AGGATCGTGGAATGTCTGCCCATGATTAACTTCAATTTTATACCTGTAAGTTATACCACATCCTAAACACGCTGATGTCCAGAGAACATTTTGACCAGCT
TCCTAGCACCTTACAGACGGGGTACTAATTGAAGTTAAATATATGGACATTCAATAATGGTTAGGAGGATTGTGCGACTACAGGGTCTCTTGTAAAACTGGTCGA 2310       2320       2330       2340       2350       2360       2370       2380       2390       2400
GCTAACAAACCAGGAGCATTTAGAAAAAACTGAGTCACCGGTTCTGGATAATGATGGAGAGAAACAAATGGGATTATTCTTACAGAGTATGAAA
CGATTGTTTGGGTCCTCGTAAATCTTTTTTTGACTCAGTGGTGGCAAGACCTATTACTACCTCTCTTTGTTTACCCTAATAAGAATGTCTCATACTTT 2410       2420       2430       2440       2450       2460       2470       2480       2490       2500
GTTACATAATTTTCCTGGATAATGGAGAATTAATAAACATCAGCATCTTTTCTGGACTTGCAGAGGTGAAGCCAATCTTTCCGGAAAT
CAATGTATTAAAGGACCTATTACCTCTTAATTAATTTGTAGTCGTAGAAAGAGACCTGACGTTCTCCACTTCGGTTAGAAAAGGCCCTTTA
```

FIG. 15-5

```
2510        2520        2530        2540        2550        2560        2570        2580        2590        2600
GGAGGAGGAAAGAATTTGACTACTATTTGGGGGGTTAACAATACATCTTACTAGCATGGCAAAGGAAACTGGGCTGCTTTTCAGAGTAAGCCACCCAGTA
CCTCCTCCTTTCTTAAACTGATGATAAACCCCAATTGTTAGTAGACATCGTACCGTTTCCTTTGACCCGACGAAAAGTCTCATTCGGTGGGGTCAT 2610        2620        2630        2640        2650        2660        2670        2680        2690        2700
GATGCTGCAAGGCTTGTGCTTTCATCCAGGGAGAAAGTCAACAGGCCATGCCCATAATGTAACCACTTAGGCTGAGGCAGAAAGAT
CTACGACGTTCCGACACGAAAGTAGGGGTCCTCTTTCAGTTGTCCCGGTCTTGTACGGGTATTACATTGGTGAATCCGACTCCGTCGTCTTTCTA 2710        2720        2730        2740        2750        2760        2770        2780        2790        2800
CAAAAATCCCAGGCCAGCTTAGTTTGTGAGCAATGAAGAACTTTGCTCAAACAAAGATTTACAAAACAAAGCAAACAAAAATATAAAAAAGGAGAAGA
GTTTTAGGGGTCCGGTCGAATCAAAACACATTGTTCTGAAACGAGTTTGTTCGTTTGTTGTTATATTTTTTTCCTCTCT 2810        2820        2830        2840        2850        2860        2870        2880        2890        2900
AAATAACTGCCAGGGGAGGCTGTGAGCAATGAAGGACTTGATGAGTGACCATCTCGCACAGTGGACGCCTTGTGTCTAGAAGGTAAGGGCTTGGCAATGTTT
TTTATTGACGGGTCCCCTCCGACACTCGTTACTTCTGAACTACTCACTGGTAGAGCGTGTCACCTGCGAACACAGATCTTCCATTCCCGAACCGTTACAAA 2910        2920        2930        2940        2950        2960        2970        2980        2990        3000
CCCAGGGTTTTCCATTCCTGGTTTATATGGCTTGAGGCCAGTGGACTTCACAATGTCTCAGCTTCCAGGTCTTTTATACAGAGCAATATTAGCCACATGTGGT
GGGTCCAAAAGGTAAGGACCAAAATATACCGAACTCCGGTCACCTGAAGTGTTACAGAGTCGAAGGTCAGAAATATGTCTCGTTATAATCGGTGTACACCA
```

FIG. 15-6

AGCTTGTGCCTGTAAGCTGGCACTTGAGAGACCAAGAGGATTGCCAACAAGTCTCCATCCAGCCTAGGTGTCACTCTGTCTCACCCTGA
TCGAACACGGACATTACGACCGTGAACTCTCTGGTTCCTCCTAACGCTGTTTCAGAGGTCGGATCCACGACACAGTGAGACAGAGTGGGGGACT
3010  3020  3030  3040  3050  3060  3070  3080  3090  3100

CCCAGTCCACCAACATCAGGCTATCACTGTGACACTGGTACTGAGTCAGAATCACCCAGAGATTAAAGATTTCTGGGGATCCAGTCCTGGGGATGCG
GGGTCAGGGTGGGGTTGTAGTTTGTCCGATAGTGACACTGTGACCATGACTCAGTCTTAGTGGGTCTAATTTCTAAGACCCTCAGTCAGGACCCCTACGC
3110  3120  3130  3140  3150  3160  3170  3180  3190  3200

GGAAGTGAGACCAGTTATTAATTCTTATATCATGAGATGATGGATCCAGAGAAAATTGTAAAATTTTATAATTGAAGAAATAGGT
CCTTCACTCTGGTCAATAAATTATTAAGAATATGAGTACTACTACCTAGTCTCTTTAAACATTTTTAAAAATCCAAAAATATTAACTTCTTTATCCA
3210  3220  3230  3240  3250  3260  3270  3280  3290  3300

GGTTTCTTCAGGTTACATCTCTCCACTGTTGGTCATTTCAGCTAAGGTCACTCCCATTGATTCCTGTGAGGCTCTCTCACATCCCAGTTGTCTCTGGGACTTT
CCAAAGAAGTCCAAATGTAGAGGTGACAACCAGTAACTAAGGACACTCCGAGAGTGTAGGGTCAGAGACCCTGAAA
3310  3320  3330  3340  3350  3360  3370  3380  3390  3400

CTAGAGGTTCCCGCTGCTTCCAGCCCTGAAAATGCGTATTTCTATTCATTCCTGGCCTTCTCTCCTGTTCCCCGCCTCACCCAACACCT
GATTCTCAAGGGCGACGAAGGGTCGGGACTTTTACGCATAAAGATAAGTAAGAGGACCGTAAGACCCGAAGAGGAGGAGGGGTTGTGGA
3410  3420  3430  3440  3450  3460  3470  3480  3490  3500

*FIG. 15-7*

3510 GATCCTGCCCCTTTCTCTCCCCCTTCTCTCTAAACCAGGTCCCCTGCCTCCATGATTATTTTGTTCCCTTCTCTAAATGAGTCTGAA
3600 CTAGGACGGGGGAAAGAGAGGGGAAGAGAGATTTGGTCCAGGGAGGAGGGAGGGTACTAATAAAACAAGGAGGAGATTACTCAGCTT

3610 GCATCCTCACTTGGACNTTCCTTCTTGTTAAACTTCATATATGGTCTGTGAGTTGTATCAGGGTATTCTGTACTTTTTTTGGCTAAGTTTCACTTATCAGT
3700 CGTAGGAGTGAACCTGNAAGGAAGAACAATTGAAGTATACCAGACACTCAACATAGTACCCATAGAAAAACCGATTACAAAGTGAATAGTCA

3710 GAGTGCAAACCAGGCATATCCTTTGAGTTGGGTTACCTCACTCAGGATGATATTTTCTAGTTTCTTATCCATTCGCCCTGCAAAATTCATGATGTCCTAAT
3800 CTCACGTTTGGTCCGTATAGGAAAACTCAAATGGAGTGAGTCCTACTACTATAAAGATCAAGATAGGTAAGCGGACGTTTAAGTACTACAGGATTA

3810 GAGTGCAAACCAGGCATATCCTTTGAGTTGTAAATGAACCATATATTTCTGAACATCTGTTCTTCAGCTGAGGAAATCTGGGTTGTTTCCAGCTTCTAGGTAT
3900 AAAATCATCGACTTATCATAAGGTAACACATTTACTTGGTATAAAAGACGTAGACAAGAAGTCGACTCCCCTTTAGACCCAACAAAGGTCGAAGATCCATA

3910 TTTTAGTAGCTGAATAGTAACACATATCCTTGAGGTATGGTAGAGCATCTTTTGGGTATATATCCAGGAGTGGATAGTTGGGTTTTCAG
4000 TATAAATAAGGTTGCTATGAACATAGTGGAACATATCCTTGAGGTATGGTAGAGCATCTTTTGGGTATATATCCAGGAGTGGATAGTTGGGTTTTCAG
ATATTTATTCCAACGATACTTGTATATCACCTTGTGTATAGGAACTCCATACCATCTCGTAGAAAACCCATATATAGGTCCTCACTTATCAACCCAAAAGTC

FIG. 15-8

```
4010        4020       4030       4040       4050       4060       4070       4080       4090       4100
GTAGAACTATTTCCAATTTTCTAAGGAACCACCAGATTGATTTTAGATAGACAGGGAGCCCTAGTGGAGAGGATGGGCAAACACCTACCTTCAAAAATT
CATCTTGATAAAGGTTAAAGATTCCTTGGTGTGTCTAACTAAAAATCTATCTGTCCCGGGATCACCTCTCTACCCCGGGTTTTGTGGATGGAAGTTTTAA 4110        4120       4130       4140       4150       4160       4170       4180       4190       4200
TGGTCCAGAAATTGTTCCTCTCTAAAAGAAAATGCAGGGACACAAAAAATGAAACAGAGACTGACCAACCCATCCTATGGGCAAGCACCAAAC
ACCAGGTCTTAACAAGGAGAGATTTTCTTAAGTCCCCTGTTTTTGTCTCGACTGGTTGGGTTGAATCCTAGGATACCCGGTTCGTGGTTTG 4210        4220       4230       4240       4250       4260       4270       4280       4290       4300
CCAGACTCTATTATTGATGCCATGTTGTGCTTGCAGACAGGAGACTTAGCATGCCTCTCTGAGACACTCTATCAGCAGCTGACTGGGACAGATGCAGA
GGTCTGAGATAATAACTACGGTACAACGAACGGTCTGTCCCTACGACAGGAGACTCTGTGAGATAGTCGTCGACTGACCCGTGCTCTACGTCT 4310        4320       4330       4340       4350       4360       4370       4380       4390       4400
TGCCAACCCTTGAACTGAGGTCAGGAGACCCTATGGAAGAATTAGGGAAGGTTTGAAGGAGCTGAAGGGAAAAACAAGTGTC
ACGGTTGGGAACTTGACTCCAGTCCTCGGGATACCTTCTTAATCCCCTTCCAAACTTCCTCGACTTCCGTTGGGGTATCCTTTTTTGTTCACAG 4410        4420       4430       4440       4450       4460       4470       4480       4490       4500
AACTAACCCTCAGAGCTCCAGAGACTAAGCCACAACTAAAGAGCATACATGGCTGGTTTGTCCTGGCAGAGGACTGGCCTTGTCTGGCCTCAGT
TTGATTGGGAGTCTCGAGGGTCTCTGAATCCGTGTGTTGATTTCTGTATGTACCGACCAAAACACCAGGAACAGACCGGAGTCA
```

FIG. 15-9

```
                                                                                                                                                                                 4510         4520         4530         4540         4550         4560         4570         4580         4590         4600
AGGAGGAATGTGCCTAATCCTTCTAGAGACTTGATGCCCCAGGAAGGGACAAGGTGGGGATTGGGTAGTGGGGTTGGGGG
TCCTTCTCCTACACGGATTAGGAGGATCTCTGAACTACGGGGTCCTTCCCCTGTTCCACCCCATCACCCCCAACCCCC 4610         4620         4630         4640         4650         4660         4670         4680         4690         4700
TGGGGGGTGGGGATTGAATGGGTGAGTGAGTGAGGGAATGAGTGAGTACAAGTGGGGTACAAGCACTCCTCTCAGGCAAAAGCCCTGGATGGAGTGGATAACAAAC
ACCCCCACCCACTACCACTCACTCCCCTTACTCACTCACCACCATGTCGTAGCACATCTCGTTTCCCCTTCCCACCTATTGTTTG 4710         4720         4730         4740         4750         4760         4770         4780         4790         4800
TCTGGGAGCAGGGACGGGGAAGGGCAACATTTGTAATTAAATAAATTAATTAAAATATTTTTTACTTCTTTGTCCTATTGAACCCTTGGGAATGGTTA
AGACCCTCGTCCCTGCCCCTTCCTCGTTGTAAACATTAATTTATTTATAAAATATTAATAAAATGAAGAAACAGGATAACTTGGGAATGGTTACCAAT 4810         4820         4830         4840         4850         4860         4870         4880         4890         4900
CAGCAGGGCTGGGATTAGAACCCAAAAAGTTTATTCTGAGACTCTCTTTTCCAATACCAAGCTTAAGTTTCTTCAGAATTCTATAGAATGCCTTTTGGC
GTCGTCCGACCCTAATCTTGGGTTTTTCAAATAAGACTCTGAGAAGTTATGGTTCGAAATTTCAAAAGAAGTCTTAAGATATCTTACGGAAAAACCG 4910         4920         4930         4940         4950         4960         4970         4980         4990         5000
AGAAGTTTCTTTGGACTTTAATTAAGAACATATTGAAGAGATGAAAAAGAAGCTTACTAAGATCTAATGAAAATCAAGATGCTAGGCACAGTGCCAGATACT
TCTTCAAGAAACCTGAAAATTATTCTGTATAACTCTCTACTTTTCTTCGAATGATTACTTTAGTTCTACGATCCGTGTCACGGTCTATGA
```

FIG. 15-10

```
5010       5020       5030       5040       5050       5060       5070       5080       5090       5100
TTAACATAGTAATAATGACTCTTTAGAGTTTTGAGACAGGGCCTCATATAGTTTATGATGAAATTCACTGTTTTTGTCAAAGATGACCTTGAACTCTTAATCC
AATTGTATCATTATACTGAGAAAATCTCAAAACTCTGTCCCGGAGTATATCAAGTACTAAGTGACAAAAACAGTTTCTACTGGAACTTGAGAATTAGG 5110       5120       5130       5140       5150       5160       5170       5180       5190       5200
ATTCCAAAAGTGTTGTTTGTTCATATATGTTTGCACCACTCCTGGCCTTCATATAGTGTTTTTAAAACACCATGGAAGAGTCGGGTGTGAAGATCCACAGTCTAAC
TAAGGGTTTCACAACAACAGTATACAAACGTGGTGAGGACCGAAGTAGTAACAAAAATTTTGTGGGTACCTCTCAGCCACACACTTCTAGGTGTGCAGATTG 5210       5220       5230       5240       5250       5260       5270       5280       5290       5300
CTCAGCATCTGGTGAATCAAGGCAGGAGGAGGGGGTGGTTGCAGGCTGGCCTATATAATATCTAAGTTCAGTTAGTAAGGGCTGCATAATGAAACACTGTCTT
GAGTCGTAGACCACTTAGTTCCGTCCTCCCGGCCCCAACGTCCGACCGATATTATAGATTCAAGTCAAATCATTCCGACGTATTACTTTGTGACAGAA 5310       5320       5330       5340       5350       5360       5370       5380       5390       5400
AAACACAAAACCAAAACCATGAAGGAGATACTATTGCCATTTAAAAGTCTCTGGAATGAAATAGCTATCATAATCTTACCTCTGAGCCAGTGTCTGCC
TTTGTGTTTTGGTTTTGGGTACTTCCTCTAGATAACGGTAAATTTCAGACCTTACCTTTATCGATAGTATTAGAAATGGAGACTCGGTCACAGACGG 5410       5420       5430       5440       5450       5460       5470       5480       5490       5500
CTCAGGTGTGCCTGAGGACTGAACAGGGCTATGCACTCCTCAGGTTGGAAACATTACTAGTCCTCAGTGTGTTGCTCTTGACCTTGTTAACAGCTGAGTCAG
GAGTCCACACGGACTCCTGACTTGTCCGATACGTGAGGAGTCAAACCTTTGTAATGATCTAGGAGTCACAGACGAGAACTGGACAATTGTCGACTCAGTC
```

*FIG. 15-11*

```
5510      5520      5530      5540      5550      5560      5570      5580      5590      5600
GGTCTGCCCTCAGCTGTGCCTGAGGACAGAGAGCTGAGCTAGTACCCTGCGACAGCATTACAGGCACTCAAGATCAGCCCCTGAAGTGATAAAACC 5610      5620      5630      5640      5650      5660      5670      5680      5690      5700
CCAGACGGGAGTCGACACGGACTCCTGCTCGACTCGATAGATGGGACGTCTAACCTTCGTGAGTTCTAGTCGGGGACTTCACTATTTTGG 5710      5720      5730      5740      5750      5760      5770      5780      5790      5800
TAAGGCAGAAATTCCACCAAGACTAGCAGAGTGCCTCCGTGTCTCTGTGCCTGGTGGGAAAGAGGCAGTCCTTCCTTGATGCAAGGTCGTGTC 5810      5820      5830      5840      5850      5860      5870      5880      5890      5900
ATTCCGTCTTTAGTTGTTGGTTCTGATCGTCACGGAGGCACAGAGGAAGGACACCCTTTCTCTCCCGTCAGGAACTACGTTCCAGCACACAG 5910      5920      5930      5940      5950      5960      5970      5980      5990      6000
ACTCTGCTCCTGTAGACATAATCACTTCTGTTGGTCTCTTTATAGAGATGATTATATAACTTTGTATGTGTTTTTATGAATTCATCACTCATCCATC

TGAGACGAGGACATCTGTATTAGTGAAGACAACCAGAAATATCTCTACTAAATATTGAACAAAATATCAAAAATACTTACACACATAAGTAAATCC

ATCACCGTGCGAAGTAAGGGTCACTCTCGTTCACTAGTGGACCCATTCCTTCCAAGTCCACGGACTCGAGCGACCTCTTAAGTAGTGAGTAGGTAG 5910      5920      5930      5940      5950      5960      5970      5980      5990      6000
TCACATGGAGTACACATTTCAGGTGTGTCTGTCTTTCCATCACGTCTTGCACGGGCTTGAATTAAACTCAGTGTTTTTACCGGCTGAGCCATCTCACCTGCC

AGTGTACCTCCATGTGTGTAAAAGTCCACAGACAGAAAAGGTTAGTAGTGTGCCCGAAAACTTAATTTGAGTCAGAACCAAAAATGGCCGACTCGGTAGAGTGGACGG
```

```
6510       6520       6530       6540       6550       6560       6570       6580       6590       6600
GTGAAAACAAAAACAGGAGAGCAAGTGCTGCTCCCGTGCCCAAAGCCCTTCTGTCAGGATCCCAGAATGCACCCAGAGAACAGCTTAGCCTGCAAG
CACTTTTGTTTTTGTCCTCTCGTTCACGACGACGGGCCACGGGGTTTACGTGGGGTCTCTTGTGAATCGGACGTTC 6610       6620       6630       6640       6650       6660       6670       6680       6690       6700
GGCTGGTCCTCATCGCATACCATACAATAGGTGGAGGGCTTGTTATTCAATTCCTTAGGAGGATACCCCTATTGTTCCTGAAAATGCTGACCAGG
CCGACCAGGAGTAGCGTATGGTATGTATCCACCTCCGAACAATAAGTTAAGGACGGATAACTCTCCTAGGGGATAACAAGGACTTTACGACTGTCC 6710       6720       6730       6740       6750       6760       6770       6780       6790       6800
ACCTTACTTGTAACAAAGATCCCTGCCCCACAATCAGTTAAGGAGAGCAGGAGAAGATAAGCCTTGGATGAAGGGCAAGA
TGGAATGAACATTGTTTCTAGGGACGGGTGTTAGGTCAATTCCGTCCTCGTCCTCGGCCTCTTCTATTCGGAACCTACTTCCCGTTCT 6810       6820       6830       6840       6850       6860       6870       6880       6890       6900
TGGATAGGGCTCGCTGCTCAGAAGCCCTGCTGATACCAAGTGCCTTTAAGATACAGCCTTCCCATCCTAATCTGCAAAGGAAAACAGGAAAAAGGAACT
ACCTATCCCGAGCGACGACGGGGCTTCGGGACGACTATGGTTCACGGACGAAATTCTATGTCGGAAAAGGGTAGGAGGATTAGACGTTCTTGTCCTTTTCCTTGA 6910       6920       6930       6940       6950       6960       6970       6980       6990       7000
TAACCCTCCCTGTGCTCAGACAGAAATGAGACTGTTACGGCCTGCTTCTGTGTGTTTCTCCTTGCCGCCAATCTTGTAAACAAGAGCGAGTGGACCATGC
ATTGGGAGGACGAGTCGTCTTTACTCTGACAGAAGACACCACAAAGAGGAACGCGCGGGTTGAACAGATTGTTCTCGCTCACTGGTACG 7010       7020       7030       7040       7050       7060       7070       7080       7090
GAGCGGAAGTCGCAAAGTTGAGTTGTTGAAAGCTTCCAGGACTCATGCTCATCTGTTGGACGCTGATGGGAGATCTGGGAAGTATG
CTCGCCCTTCAGCGTTTCAACACTCAACTTTCGAAGGGTCCCTGAGTAGACACCTGCGACCTACACCCCTTCATAC
```

FIG. 15-14

```
  10        20        30        40        50        60        70        80        90       100
CTCGAGGTCCAGTATGGCTTCTCAACTTGGCAAGAGGCTGCAGGGACGACCAGGAAGTTTGAAACAGTCTTAGAAGAAAATGCTGGCTTAGAGAC
GAGCTTCAGTCATACCGAAGAGTTGGAAGAACCGTTCTTCCGACGTCCTGCTGGTCCTTCAAACTTTGTCAGAATCTTCTTTTTACGACGAATCTG 110       120       130       140       150       160       170       180       190       200
AGGTGGCAATGGGGATGGGCAGAGCAGTATTCTCGGTTTGCATAGAGGTCCTTCCAAGTGCTGGGAAACAAGGAGGAGGGCAGGGATAGAGCAAAT
TCCACGTTACCCCCTACCCCTCGTCATAAGACCAAACGTATCTCCAGGAAGGTTCAGAAGTCCTCCGGTCCCTATCTCGTTTA 210       220       230       240       250       260       270       280       290       300
GATGGCTCTGTAGTGTCCTGTGTCAGTTTGCATTTAATCTGAGCAAAAATTTGGCTTTTGACATCTCGCAACTCAAAAGAAGGTAATTAGGCAAATGACTG
CTACCGAGACATACACAGGACAAGTCAAATTAGACTCGTTTAAAACCGAAAACTGTAGACGTTGAGTTTTCTTCCATTAATCCGTTTACTGAC 310       320       330       340       350       360       370       380       390       400
TTGTATCTATAGAATTATCAGTTCCTAAAAAAAAAAAACTTCTCAATCGTCAGTCCCCTACCATCTTTGACGTTTGGTTAGGCATAAGAAAG
ACACATAGATATCTTAATAGTCAAGGAATTTTTTTTTTTTGAAGAGTTAGCAGTCAAGGGATGGTAGAAATCGCAAAACCAATCCGTATTCTTTC 410       420       430       440       450       460       470       480       490       500
TTGAGATTTTAGACAGTTGATGCTACTAGCCACAAAAAAGAGTTTAAGTGGAGGAGAGTGCAGGACCAAGGTGACAGGCTCCAGGTCTGTAG
AACTCTAAAAATCTGTCAACTACGATGATCGGTGTTTTTCTCAAAAATTCACCCTCCTCTCACTTCTACGTCCTGGTTCCACTGTCCGAGGTCCAGACATC
```

```
1110      1120      1130      1140      1150      1160      1170      1180      1190      1200
CATGTATGGATCTGTCACAGGAGGCTGGTGAGGCTGATGGGTGTGGCCACTGTTTGCTCTCTGCTTGTCACAGCCTCTTGTTCAGGGCTTGATCA
GTACATACCTAGACAGTGTCCTGACCACTCCGACTACCCACCACACCCACCGGGTGACAAACGAGACGGACGAACAGTGTCGGAGAACAAGTCCGAACTAGT 1210      1220      1230      1240      1250      1260      1270      1280      1290      1300
GGCAGGTGTGTGTGTGTGTGTGTGTGTGTGTGTGGTTCACCCATCTCAGCAGATCTGTCAGCTTTCCCGCTTTTGTTAGAGGGTG
CCGTCCACACACACACACACACACACACACACACACCAGTGTGGGGTAGGACTGCGTCTGAAAGGGCGAAAACAATCTCCCAC 1310      1320      1330      1340      1350      1360      1370      1380      1390      1400
ATATCATGCTTCCTGGGGAGCTCTGGAAGACAATGAGCAGCCACTTTCCTCTAGATACAATAGGCGGAGTCAGGAAGGTAGTATTGACATTGCTGGG
TATAGTACGAAGGACCCCCTCGAGACCTTCGTTACTCGTCGGTGAAAGGAGAATCTATGTTAATCGGCCTCCAGTCCTTCCATCATAACTGTAACGACCCC 1410      1420      1430      1440      1450      1460      1470      1480      1490      1500
CCTAGGAGCTACTCACTGCTCGGTGGCCGTCAGATGATGGTGAACCTTGGGCACACAGCCTGTTGTACAAGGGTCTCGGCTGCAGGGGCCAAA
GGATCCTCGATGAGTGACGAGCCACCGGCAGTCTACTACCTTGGCCGAGTCATGGAACCGTGTTGTCCGGACCCGACACATGTTCCAGAGCCGACGGTCCCGGTTT 1510      1520      1530      1540      1550      1560      1570      1580      1590      1600
GAGGACTCCACCTAGGACAGGAGTACTTCAGACATCTGGGAATGGGTTTTAAAATTCAGATCCAATATAAAAAAAACAACTCCAAACAAA
CTCCTGAGGTGGGATCCCTGTCCTCATGAAGTCTGTAGACCCTTACCCAAAATTTTTAAGTCTAGGGTTATATTTTTTTGTTGAGGGTTTGTTT 1610      1620      1630      1640      1650
CAGCAGCAATTAAAAAAAAAAAAAAACAGCCTCCCAAAGTAAAACAATAATGTACC
GTCGTCGTTAATTTTTTTTTTTTTTGTCGGAGGGTTCATTTTGTTATTACCATGG
```

FIG. 16C

SEQUENCE LISTING

<160> NUMBER OF SEQ ID NOS: 51

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: primer
      PGKF

<400> SEQUENCE: 1
atcgaattct accgggtagg ggaggcgctt t                                  31

```
<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: primer
      PGKR

<400> SEQUENCE: 2
ggctgcaggt cgaaaggccc ggagatgagg                                        30

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: primer NeoF

<400> SEQUENCE: 3
acctgcagcc aatatgggat cggccattga ac                                     32

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: primer NeoR

<400> SEQUENCE: 4
ggatccgcgg ccgcccccag ctggttcttt ccgcctc                                37

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: primer TKF

<400> SEQUENCE: 5
ggatcctcta gagtcgagca gtgtggtttt                                        30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer TKR

<400> SEQUENCE: 6
gagctcccgt agtcaggttt agttcgtccg                                        30

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer
      F5R51

<400> SEQUENCE: 7
gtacatttaa atcctgcagg                                                   20

<210> SEQ ID NO 8
<211> LENGTH: 20
<212> TYPE: DNA
<213> ORGANISM: Artificial Sequence
<220> FEATURE:
```

-continued

```
<223> OTHER INFORMATION: Description of Artificial Sequence: primer
      F5R52

<400> SEQUENCE: 8
agctcctgca ggatttaaat                                              20

<210> SEQ ID NO 9
<211> LENGTH: 77
<212> TYPE: DNA
<213> ORGANISM: Artificial Sequence
<220> FEATURE:
<223> OTHER INFORMATION: Description of Artificial Sequence: primer
      F3R31

<400> SEQUENCE: 9
ggcccgggct taattaatgc atcatatggt accgtttaaa cgcggccgca agcttgtcga   60
cggcgcgccg gccggcc                                                 77

<210> SEQ ID NO 10
<211> LENGTH: 77
<212> TYPE: DNA
<213> ORGANISM: Artificial Sequence
<220> FEATURE:
<223> OTHER INFORMATION: Description of Artificial Sequence: primer
      F3R32

<400> SEQUENCE: 10
gatcggccgg ccggcgcgcc gtcgacaagc ttgcggccgc gtttaaacgg taccatatga   60
tgcattaatt aagcccg                                                 77

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: primer VN1R

<400> SEQUENCE: 11
ctgtatttaa atctgcccac cctattcagg acagtagtc                         39

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer VN1F

<400> SEQUENCE: 12
ccaatgcatc aacccagcca ggaggagtgc g                                 31

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: primer VN2R

<400> SEQUENCE: 13
aacgcgtcga cttcggagat gtttcgggga taaccagg                          38

<210> SEQ ID NO 14
<211> LENGTH: 40
<212> TYPE: DNA
<213> ORGANISM: Artificial Sequence
<220> FEATURE:
```

-continued

<223> OTHER INFORMATION: Description of Artificial Sequence: primer VN2F

<400> SEQUENCE: 14
ttggcgcgcc ccatagagaa gagacaccaa aggcacgctc                40

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: primer
      FosB1F

<400> SEQUENCE: 15
ctgtatttaa atcccgtttc tcactgtgcc tgtgtc                    36

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: primer
      FosB1R

<400> SEQUENCE: 16
gtctcctgca ggcttcctcc tccttgttcc ttgcg                     35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: primer
      FosB2F

<400> SEQUENCE: 17
aacgcgtcga cggatgggat tgaccccag ccctc                      35

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: primer
      FosB2R

<400> SEQUENCE: 18
ttggcgcgcc ccttgcctcc acctctcaaa tgc                       33

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: primer VF1

<400> SEQUENCE: 19
acctcactct cctgtctccc ctgattccca a                         31

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: primer VR1A

<400> SEQUENCE: 20
gctctggcgg tcaccccccaa aagca                                          25

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: primer VF2

<400> SEQUENCE: 21
ccctttccaa gacccgtgcc atttgagc                                        28

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: primer VR2

<400> SEQUENCE: 22
actttgcccc tgtccctctc tctgttcgc                                       29

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: primer KF1

<400> SEQUENCE: 23
gctgcgtcca gatttgctct cagatgcg                                        28

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: primer KR1

<400> SEQUENCE: 24
ttctcaggca cagactcctt ctccgtccct                                      30

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: primer KF2

<400> SEQUENCE: 25
cagatggacg agaaaacagt agaggcgttg gc                                   32

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: primer KR2

<400> SEQUENCE: 26
gaggactcag ggcagaaaga gagcg                                           25

<210> SEQ ID NO 27
<211> LENGTH: 29
<212> TYPE: DNA

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: primer TF3

<400> SEQUENCE: 27
agcttagcct gcaagggtgg tcctcatcg                                29

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: primer TF2

<400> SEQUENCE: 28
caaatgcacc ccagagaaca gcttagcctg c                             31

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: primer TR1

<400> SEQUENCE: 29
gctttcaaca actcacaact ttgcgacttc ccg                           33

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: primer VR2F

<400> SEQUENCE: 30
cgctagtgtg tagccggcgc tctc                                     24

<210> SEQ ID NO 31
<211> LENGTH: 38
<212> TYPE: DNA
<213> ORGANISM: Artificial Sequence
<220> FEATURE:
<223> OTHER INFORMATION: Description of Artificial Sequence: primer VR2R

<400> SEQUENCE: 31
ataagaatgc ggccgcctgc acctcgcgct gggcacag                      38

<210> SEQ ID NO 32
<211> LENGTH: 4486
<212> TYPE: DNA
<213> ORGANISM: Mus sp.

<400> SEQUENCE: 32
aagcttgcag ggaggtagga ggcagcctgt ggcgttgatt caatgcacct ggccttatcc     60
tcggatgaga tcggtcacca gtcaaaaact gtgagcttga aggtcttggg tgcttaacat    120
ctatttttac aaatcttatt tagcaactta gaactgtgaa atattggaaa gctacttaaa    180
ccttctaaac tccctcctcc acactatgag aatgttacat tttctattca gttatttttg    240
agcagtaaaa agatgaatca aggaatatgc ccatcacatc aagagtgctc ctaaatggac    300
ttgcttgtta ttcatttaca gtgtggcccc ttgactttca tcggcactcc tagcagaaaa    360
caaaatccgc cagatggagc tggagagatg gctcagctgt taagaatact tatccctaca    420
caggccctgg agccagttcc cagcacccac acggtggctc acaaccatct gtaactccag    480

-continued

```
ttctaggaga cccgactccc tcttctgtct gaaaacacca ggcacgcgtg cggctacata    540
caaacatgaa agcaaaatac acacattaca taaataaatc ttaaaaaatg attcggggtg    600
ggggaaggaa aaaaaaggat gttagaaaat cgatgtaact gttttttcct tttgcacaga    660
tctaagtagg gaaggagaac attctcttac catcgagaat aattgttttc attgccccca    720
agtctgctaa tagagcttgc taccttcatg gctgtcgtaa ggatgaggca aagatggact    780
tcagctttca gactgtgtct gctcaaatgt tggctactcc tgttttctga ccccttctc    840
tggtgcaatg tggactttca attaatttcc ctgcatcttt tacatatttg atttaaaaaa    900
tattttattt tatgtaattg tatgtatatg catgtcaata agcatatgtg tgtgtgtttc    960
catggaaacc aaggcaacag attctccaga gctgtagaaa tgggctgtga cacgcccact   1020
gtgggtgctc ggaaccaaac tcgggtcctg tggaaagaca gcgagcaccc ataatgcaga   1080
ggtatctctc agactctact ttaaaatttc aatttatctt ttttttttt aaagttccaa    1140
gtaactatag gaaagtacat gggtatatag atccccagta ccaagattct tcctttgcag   1200
gtagcacaac ttggtctgct tcacataaag aatggaaagt cattaaaaca ctcatcacac   1260
tgtaaagtag aattgaactc tgacagaaca agcgaagtga gtctgacttc caggtaactg   1320
agccttcttt tcctcctaaa gacacaagcc atacacagag taaataaac ttgggcatgg    1380
tgagaaggaa acaacgcagg agggctagcc aagtctgaga gtcgtgagtg tgctcggttt   1440
ataaacggag cccaccttgc cagcgaggta gtcacatgct ctgctaaaca gaaacttaag   1500
aaaacactta cacgaagcaa acatggggaa gtgccatgca agcatgtgac tgactggtgg   1560
caatgaccga aaccacagca gcccactagaa aaggaagggt agtgcgccac actgtagttg   1620
tgaaaatgaa cttattcatt tattttgaaa aacgtgtaag aagcaaagat gtcttctttc   1680
ccacctacct ttgcggcagg cgagcacttc ctggaattta taaagtgcga tctttctggg   1740
gacttctcat aacatttcct actgctcatc tatgtctgtg tcaaatagag aatgctcttg   1800
aacaagtgtg tgtgtgtgtg tgtgtgcgcg cgcacgcgca ctcactcctg ctctgttgag   1860
gtccagtttt gatggtcccg ccagaggtat atttgagtat catttctcaa gagcttcagc   1920
tgggagacac tgcctcttac tggcctgaag gtcactagct gattcatctc cgtttgggct   1980
ggcgcgcctt gggatcctc ctatctctcc ttccccagtg ctgggataac aaggttggca    2040
ccacatgagc cttttaaaat gtgagtttgg aagctcaaac gcaggttttc atgcttgcac   2100
tgaaacttca caagctgaac cgtctccctc tccttccctc tcttttttcc ttttcttctt   2160
ccttttaaa acacatcttg tctttaaaaa aaaaaaagg cccaaaacaa gtgtaaagta    2220
tttccctatg tgtgtggagg gagggagtat aggaggctga tttcactgag atcctgttaa   2280
atttgggtgc catagccaat caaagacgca tcgtttcctc taagaattct aaatggggcg   2340
attaccacgg gcctgcaggt tctggttttgt attagaggag acactgtctt cttaagtaaa   2400
acatagaagg ggaagtgtcc agaattgtaa ataaggcttc gagagaagcc ttgtctggcc   2460
accgggatgg agaagaccta ccttcgccta tccaggatcc atcgtccctc cctctaccca   2520
gatctgacag ccctccttgg ctcttttgct gaggtttgtt tgagtttgtt ttactctctg   2580
caagagaagt ttccttaaac attctaccct gttcacaagt aaatacacct cttagctaag   2640
aggccacaca cccaggggaa caccgataaa agaacaagc cagaaccttc agaacgctgt    2700
cgataggtac accaagcagc cttcatacgg agttttcatt cgtgaggagc tgaatataca   2760
acaaagctaa atgtgagcag accaggcatg cctctgctaa atgaggatgc ccacaccaaa   2820
```

-continued

```
catgcccaag atcttcaagt ataattttat tatatagatt cgctatgtgt tgacatgttt    2880
ttatagtgaa cctggatttt acaaaccctc ctggtttgcc acctgcttct ggcaccatac    2940
ttgaggctta ggcacgtgat aaaggagcat gcctgtttcc ccccttattt tttttaaaga    3000
aaagcaccat gttacatcat taatcatgca tatcagtgta gtttagatcc gatgtagaga    3060
caataatctt atctctttgt ctggctgaaa gactgtcctt taaactatca ttctaaatgc    3120
atttggtttt tgccaggagt aaaacatgtc acaagatatt tgttgtcatt tcccaggcgt    3180
ggaaggaaag gaatggaaag aaaacgaggg gtgaaggctg ctgttcctct ctagtcgcta    3240
cttgaagtct acatagctgg ggggggggg gggactgttc acatgggacc ggtttcctct    3300
ttgttcctac actggcgcct ctggcaagaa actctccctt ctcttccccc caagcatatc    3360
ttggctgaaa ggtcagctct gaaaaggggc ctggccaaag ttactgtagg ggaccgtggt    3420
catggaactg ggtagacaaa agcactctag cagccactgg agaaggaccg ggggctcttc    3480
tctgtgcatt tgccctggag ccctgaccac cgccagctcc ctgcatctcc ttgctatggg    3540
ttttctggac cgagccaggc aggagttcac aaccgaaatg tcttctaggg ctaatcaggt    3600
aacttcggac gatttaaagt tgccagatgg acgagaaaac agtagaggcg ttggcaacct    3660
ggataagcgc ctatcttcta attaaaacat tcagacgggg cgggggatgc ggtggccaaa    3720
gcaccataaa acaaaacttc caagtactga ccaactcact gcaagtttgt gccccgagta    3780
catctaggtt caggggtctt gtcttcatgc tcccaactgc gggcggattt ttggtccctt    3840
gggactttca gtgcagcggc gaagagagtt ctgcacttgc aggctcctaa tgagggcgca    3900
gtgggcctcg tgtttctggt gatgcttccc aggttgctgg gggcagcaag tgtctcagag    3960
cccattactg gctacatttt acttccacca gaaaccgagc tgcgtccaga tttgctctca    4020
gatgcgactt gccgcccggc acagttccgg ggtagtgggg gagtgggcgt gggaaaccgg    4080
gaaacccaaa cctggtatcc agtgggggc gtggccggac gcagggagtc cccacccctc    4140
ccggtaatga ccccgccccc attcgctagt gtgtagccgg cgctctcttt ctgccctgag    4200
tcctcaggac cccaagagag taagctgtgt ttccttagat cgcgcggacc gctaccggc    4260 aggactgaaa gcccagactg tgtcccgcag ccgggataac ctggctgacc cgattccgcg    4320
gacaccgctg cagccgcggc tggagccagg gcgccggtgc cccgcgctct ccccggtctt    4380
gcgctgcggg ggcgcatacc gcctctgtga cttctttgcg ggccagggac ggagaaggag    4440
tctgtgcctg agaactgggc tctgtgccca gcgcgaggtg cagatg                  4486
```

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: primer VEF

<400> SEQUENCE: 33

```
acacgcctcg agaaatgtgc tgtctttaga agccactg                            38
```

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: primer VER

<400> SEQUENCE: 34

```
acacgcgtcg acgatccaat aggaaagccc ttccataaac                          40
```

<210> SEQ ID NO 35
<211> LENGTH: 511
<212> TYPE: DNA
<213> ORGANISM: Mus sp.

<400> SEQUENCE: 35

| | |
|---|---|
| aaatgtgctg tctttagaag ccactgcctc agcttctgca gctcagatac caaaggaagt | 60 |
| ctggtacaca gcatgataaa agacaatggg acggggtcac agtggctccc gtccctttca | 120 |
| ggggtatgga gacgagctgt agagagatgt ctccagggag ttttcattaa tcagcaattt | 180 |
| agtcagatct gtgcatccta tgctttacaa gaaatgtcag tgggcctgag atcatcagat | 240 |
| ggaggttcat cgggtttcaa tgtcccgtat ccttttgtaa gaccttgaag ttggcaacgc | 300 |
| aggaaaacag gaactccacc ctggtgccgt gaattgcaga gctgttgtgt tggtttgtga | 360 |
| ccatctgccc attcttcctg ttatgacaga gcttgtgaac tttaactggg actggggcaa | 420 |
| agtcaatccc acctttatac aatgaattgc tgaagaggcc ttttaaaact tggagtgtgc | 480 |
| attgtttatg gaagggcttt cctattggat c | 511 |

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: primer
      GL3B-Forward

<400> SEQUENCE: 36

| | |
|---|---|
| gtacttaatt aagcttggta cccggggcgg ccgc | 34 |

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: primer
      GL3B-Reverse

<400> SEQUENCE: 37

| | |
|---|---|
| agctgcggcc gccccgggta ccaagcttaa ttaa | 34 |

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: primer T2
      Forward

<400> SEQUENCE: 38

| | |
|---|---|
| tatcaacact cgggaggctg agggag | 26 |

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: primer T2
      Reverse

<400> SEQUENCE: 39

| | |
|---|---|
| ataagaatgc ggccgcactt ccccagatct ccccatccag c | 41 |

<210> SEQ ID NO 40
<211> LENGTH: 7093
<212> TYPE: DNA
<213> ORGANISM: Mus sp.
<220> FEATURE:
<221> NAME/KEY: unsure
<222> LOCATION: (3617)
<223> OTHER INFORMATION: undetermined

<400> SEQUENCE: 40

| | | | | | |
|---|---|---|---|---|---|
| ggtaccaaag | catagaacta | cagatccgct | ctctgcctgt | accaccctct | ggcatttaat | 60 |
| cacacaatgc | ttggttttgt | tcttcaactt | ttcctgttat | gatgcagtcc | ctggcttgtg | 120 |
| taactatgag | cttcaaaagc | aaagaacgca | tcatctattt | ttgtgtctct | tcttccaagg | 180 |
| acttagtgta | tcacttactg | gctaaatgct | tgagacaaaa | acagggatta | atgaagaaga | 240 |
| aagagaaaga | aaaggaaggg | aaagtgccca | caattactga | cagggtttca | gtaaagcagt | 300 |
| ctagagggtc | aggtattttc | catagccatg | ccccagagtg | ggtgttgcca | ctttagctgc | 360 |
| cctggtctgg | ctgaaggcca | ggacttgatt | gttgatggcc | cttcctttgc | tgctagtcac | 420 |
| tgttaagtac | tgcagattta | cagaaagctt | catggaggtc | tgtaagaagc | cagaggtgat | 480 |
| aacaccaaga | tttagagcca | ctgaccagca | gaatgcagaa | tgtccaggct | atgatccagg | 540 |
| ttgtagatcc | tgatctgact | actcaagact | ggttgaaggc | aaggttcact | tggattcact | 600 |
| ctatttgcca | gcagatgttt | taaatccatc | atatatatat | atatatctcc | attactttag | 660 |
| gacagtggtt | ctcagccttc | ctaatgctgt | agccctttaa | tagagttcct | catattgtga | 720 |
| ttgtaaaaat | tattttgttg | ctacttcatg | actaattttg | ctactgtgaa | agggtcattt | 780 |
| taccccaggc | tgttgagacc | cacatgttgg | gaaccactac | tttagaaggc | attgggggttg | 840 |
| gagaagaaca | tgaagaatag | agtaacagtg | gtcagttttg | gttcattata | tcacagaaac | 900 |
| attcacttta | aggtttcagc | atgtttgttg | tgtatatgtg | attgtgtaaa | gacttccacca | 960 |
| ggtctttctt | taatcaccat | acctaacatc | ttcaccactc | catatccatc | agcttcacct | 1020 |
| tgtactctag | catttgggca | ttcatcctgt | accagggcag | gcatccattc | ttttgcaact | 1080 |
| cacattgttt | cctagttttg | attattacca | acaatgcttc | tagaccatga | attttggtct | 1140 |
| ttgacttttg | cttggtaaac | atcataaaac | aatccagtgg | tggtggtggt | gccgctgctg | 1200 |
| ctggtggtgg | tggtaaagca | ggaagccata | aagtgccttt | attcaatctg | tatttgatac | 1260 |
| aaattgttat | ttcttcccat | gtaaaagata | tggcatctga | agtgtagagg | tctgaattca | 1320 |
| aacctcacat | caccagatag | tatattacag | actcaacaaa | taatacacgg | ctttgcctga | 1380 |
| cttcaaagcc | ctgttcttga | cgtaagtata | tgagtaacaa | tggtagcacc | ttagtttta | 1440 |
| tcagttcact | aaatatttat | ataagaccta | ctatgaaggg | agatagaagg | gtatgaggtg | 1500 |
| gggtcatggg | aataggaaaa | cggtggaagg | gagaaggaga | attaacaaaa | gctaattatg | 1560 |
| tttgaaaatg | ccacaatgaa | acctaattta | caaaagaacc | actatatgac | cttcacagtg | 1620 |
| tgtgctaagt | cttggagatt | tagtggtgaa | gaagtcaggt | gtgtttccaa | tctcatggag | 1680 |
| gatgtaatca | gttagagagc | acaggagcac | ataaaaagat | aggcaaaaat | gtatgattag | 1740 |
| taccatgtaa | gatatgaagg | ggaacacagg | aaactagtgg | ggagacctaa | tttagtttga | 1800 |
| gtggtcttca | agacccttt | agaagctgag | aactaaagac | agcaagcaag | gtgagggcag | 1860 |
| catctccacc | tttccagtgg | aatgagcaac | ttagggtata | cagctgattc | ccacattgtc | 1920 |
| aacaaggctc | ttcagagact | agagatgcac | taatgatgac | catacccagc | ttttaaggaa | 1980 |
| ggtttctgag | catgtccaag | caccctacac | taggcattgg | aaatcaacat | gtccagagat | 2040 |

-continued

```
ggaagtgaca gtcagtaagc caacccttttt caaaacttcc aaagctatta ctcgtcaact    2100
ctccagacat atgggccccg agtgtgttgg gaagctctca ttattgttct ttgattggtt    2160
ctctacattc cgagatccaa ggagcagtta tctcaggtag aggatcgtgg aatgtctgcc    2220
catgattaac ttcaatttat acctgtaagt tataccacat cctaaacacg ctgatgtccc    2280
agagaacatt ttgaccagct gctaacaaaa cccaggagca tttagaaaaa aactgagtca    2340
cccaccgttc tggataatga tggagagaaa caaatgggat tattcttaca gagtatgaaa    2400
gttacataat tttcctggat aatggagaat taattaaaca tcagcatctt ttctggactg    2460
cagagggaag acagaggtga agccaatctt tccgggaaat ggaggaggaa agaatttgac    2520
tactatttgg gggttaacaa tacatcttac tagcatggca aaggaaactg ggctgctttt    2580
cagagtaagc caccccagta gatgctgcaa ggctgtgctt tcatcccagg agaaagtcaa    2640
cagggccagg catgccagaa catgcccata atgtaaccac ttaggctgag gcagaaagat    2700
caaaaatccc aggccagctt agtttgtgta acaagacctt tgctcaaaca aagatttaca    2760
aaacaaacaa gcaaacaaac aaatataaaa aaggagaaga aaataactgc caggggaggc    2820
tgtgagcaat gaagacttga tgagtgacca tctcgcacag tggacgcttg tgtctagaag    2880
gtaagggctt ggcaatgttt cccaggtttt ccattcctgg tttatatggc ttgaggccag    2940
tggacttcac aatgtctcag cttccaggtc tttatacaga gcatattagc cacatgtggt    3000
agcttgtgcc tgtaatgctg gcacttgaga gaccaagaca ggaggattgc cacaagtctc    3060
catccagcct aggtgctgtg tcactctgtc tcaccctga cccagtccca cccaacatca    3120
aacaggctat cactgtgaca ctggtactga gtcagaatca cccagattaa agattctggg    3180
agatcagtcc tggggatgcg ggaagtgaga ccagttattt aataattctt atactcatga    3240
gatgatggat ccagatgaga aattgtaaaa attttaggtt ttataattga agaaataggt    3300
ggtttcttca ggttacatct ctccactgtt ggtcatttca gctaaggtca ctccccattg    3360
attcctgtga ggctctcaca tcccaggtct ctgggacttt ctagaggttc ccgctgcttc    3420
ccagccctga aaatgcgtat ttctattcat tctcctggca ttctgggctt ctctcctgtc    3480
ccccgcccca cccaacacct gatcctgccc cctttctctc ccccttctct ctctaaacca    3540
ggtccctccc tccctctgct tcccatgatt attttgttcc ctcctctaaa tgagtctgaa    3600
gcatcctcac ttggacnttc cttcttgtta aacttcatat ggtctgtgag ttgtatcatg    3660
ggtattctgt acttttttgg ctaatgtttc acttatcagt gagtgcaaac caggcatatc    3720
cttttgagtt tgggttacct cactcaggat gatatttct agttctatcc attcgcctgc    3780
aaaattcatg atgtcctaat ttttagtagc tgaatagtat tccattgtgt aaatgaacca    3840
tattttctgc atctgttctt cagctgaggg aaatctgggt tgtttccagc ttctaggtat    3900
tataaataag gttgctatga acatagtgga acacatatcc ttgaggtatg gtagagcatc    3960
ttttgggtat atatccagga gtggatagtt gggttttcag gtagaactat ttccaatttt    4020
ctaaggaacc accagattga tttttagata gacagggccc ctagtggaga gatggggcca    4080
aacacctacc ttcaaaaatt tggtccagaa ttgttcctct ctaaaagaaa tgcagggaca    4140
aaaatgaaac agagactgac caacccaact taggatccat cctatgggca agcaccaaac    4200
ccagactcta ttattgatgc catgttgtgc ttgcagacag gagcttagca tggctgtcct    4260
ctgagacact ctatcagcag ctgactggga cagatgcaga tgccaaccct tgaactgagg    4320
tccaggaccc ctatggaaga attaggggaa ggtttgaagg agctgaaggg gatggcaacc    4380
```

```
ccataggaaa aacaagtgtc aactaaccct cagagctccc agagactaag ccaccaacta    4440
aagagcatac atgggctggt tgtggtccc  tggcagagga ctgccttgtc tggcctcagt    4500
aggagaggat gtgcctaatc ctctagagac ttgatgcccc agggaagggg acaaggaggg    4560
gacaaggtgg ggattggtgt ggggtagtgg gggttggggg tgggggtggg gatgtgaatg    4620
ggtgagtgag ggagggaatg agtgagtggg tggtacagca tcctctcaga ggcaaagggg    4680
aaggggagtg gataacaaac tctgggagca gggacgggga aggagggcaa catttgtaat    4740
taaataaata aaataattta ataaaaaaaa tgaagaaaca ggataacttg ggaatggtta    4800
cagcagggct gggattagaa cccaaaaagt ttattctgag actcttttcc aataccaagc    4860
ttaaagtttt cttcagaatt ctatagaatg ccttttggc  agaagttctt tggactttaa    4920
taaagaacat attgaagaga tgaaagaag  cttactaaga tctaatgaaa atcaagatgc    4980
taggcacagt gccagatact ttaacatagt aatatgactc tttagagttt tgagacaggg    5040
cctcatatag tttatgatga attcactgtt ttgtcaaaga tgaccttgaa ctcttaatcc    5100
attcccaaag tgttgttgtc atatgtttgc accactcctg gcttcatagt gttttttaaaa   5160 cacccatgga gagtcgggtg tgaagatcca cacgtctaac ctcagcatct ggtgaatcaa    5220
ggcaggaggg cgggtggttg caggctggct ataatatcta agtttcagtt agtaagggct    5280
gcataatgaa acactgtctt aaacacaaaa ccaaaaccca tgaaggagat actattgcca    5340
tttaaaagtc tctggaatgg aaatagctat cataatctta cctctgagcc agtgtctgcc    5400
ctcaggtgtg cctgaggact gaacagggct atgcactcct caggttggaa acattactag    5460
tcctcagtgt ctgctcttga cctgttaaca gctgagtcag ggtctgccct cagctgtgcc    5520
tgaggacaga gctgagctat ctaccctgc  agattggaag cattacaggc actcaagatc    5580
agccctgaag tgataaaacc taaggcagaa atccaccaag actagcagtg cctccgtgtc    5640
tcttcctgtg gctggtggga aagagagggg cagtccttcc ttgatgcaag gtcgtgtgtc    5700
tagtggcacg cttccttcat tcccagtgag agcaagtgat cacctgggta aggaaggttc    5760
aggtgcctga gctcgctgga gaattcatca ctcatccatc actctgctcc tgtagacata    5820
atcacttctg ttgggtcttt atagagatga tttataactt tgttgtttat agtttttatg    5880
aatgtgtgta ttcatttagg tcacatggga ggtacacatt ttcaggtgtc tgtctttcca    5940
tcacacgggc tttgaattaa actcagtctt ggttttaccg gctgagccat ctcacctgcc    6000
tgattattta aaaatctccg gagtaatcca ggagtgtggt ttatgattgt agtatcaaca    6060
ctcgggaggc tgagggagca tcgttatcat gagctccagg ctagttccag gcttgcctaa    6120
gctgtagagc aagtcactct cttaaaaagt gcctctccca tattttgta  tataatttgc    6180 atctgaaatt ctgtttgcca ataactatga aattattcac attactaaaa tcttcctgtg    6240
ccaagttctc caacgaatta gatcacactc agatgaaatg ctaataaaaa ttaaagctgt    6300
agccagtagc atgcgtatat ttgggctcag ggccaacagg caggcgatct gggtgtaaga    6360
aaataggcta atggctgtgg aatctggtct ctagtggctc cgctgagagc tgacctcaac    6420
cacgctccct caaattgatt gccttccagg ttatgatttc tcatcacagg aaactttgtt    6480
gcccaattca aaccctgtga gtgaaaacaa aacaggaga  gcaagtgctg ctccccgtgc    6540
cccaaagccc cttctgtcag ggatcccaaa tgcaccccag agaacagctt agcctgcaag    6600
ggctggtcct catcgcatac catacatagg tggagggctt gttattcaat tcctggccta    6660
tgagaggata cccctattgt tcctgaaaat gctgaccagg accttacttg taacaaagat    6720
ccctctgccc cacaatccag ttaaggcagg agcaggagcc ggagcaggag cagaagataa    6780
```

-continued

```
gccttggatg aagggcaaga tggatagggc tcgctctgcc ccaagccctg ctgataccaa      6840
gtgcctttaa gatacagcct ttcccatcct aatctgcaaa ggaaacagga aaaggaact       6900 taaccctccc tgtgctcaga cagaaatgag actgttaccg cctgcttctg tggtgtttct      6960
ccttgccgcc aacttgtaaa caagagcgag tggaccatgc gagcgggaag tcgcaaagtt      7020
gtgagttgtt gaaagcttcc cagggactca tgctcatctg tggacgctgg atggggagat     7080
ctggggaagt atg                                                         7093

<210> SEQ ID NO 41
<211> LENGTH: 1659
<212> TYPE: DNA
<213> ORGANISM: Mus sp.

<400> SEQUENCE: 41
ctcgaggtcc agtatggctt ctcaaccttc ttggcaagaa ggctgcaggg acgaccagga        60
agtttgaaac agtcttagaa gaaaatgctg gcttagagac aggtggcaat gggggatggg      120
gagcagtatt ctggttttgca tagaggcaga gtccttccaa gtgctgggaa acaaggcagg     180
agggcaggga tagagcaaat gatggctctg tatgtgtccc tgttcagttt gcatttaatc      240
tgagcaaaat ttggcttttg acatctgcaa ctcaaaagaa ggtaattagg caaatgactg      300
acacatagat atcttaatag tcaaggaatt tttttttttt tttttgaaga gttagcagtc      360 agggatggt agaaactgca aaccaatcc gtattctttc ttgagatttt tagacagttg        420
atgctactag ccacaaaaag agttttaagt gggaggagag taagatgcag gcaccaaggt      480
gacaggctcc aggtctgtag cattagctta cagatgagat tctttacaga gagccaggca      540
gctgcattgg ctaaagcaga tctggagggg ggccaggaga tcagctggcg gcactcccag      600
cctccaggaa aggcaaccct tatttctgga attttaaact gataacccaa ttcccaccag      660
cctggccagg ctcttcctta gctcacatca caaacacaga aggattgttt tagatggagt      720
catgcttgat tctttctata cctacttcca agaccaattt tataaaagtt tatttaccgc      780
ccgtgtgtgt gtgtgtgtgt gtgtgtgtgt gtgtgtgtgt gtgtgtgtgc atggtatata      840
tggatgtcag agtttggttc tctccttctg cagtgtggct cttagagatt gaactcagat      900
catgagcaag caccttgctg cctgctatgt ccctccagca gtctgaccat gttccttccc      960
ccaagattgt ggaagctgga ctgaagatca caatctgcca gatgggcaga atctttactc     1020
tttggcacat ttgttgctga tggggagtga atacccatgg ggacatggct gtcatggtgt     1080
ggaagtgata gaaatgaaaa catgtatgga tctgtcacag gagctggtga ggctgatggg     1140 tgtgtggggtg gccactgttt gctctctgct tgtcacagcc tcttgttcag ggcttgatca    1200
ggcaggtgtg tgtgtgtgtg tgtgtgtgtg tgtgtgtgtg tgtgtgtggt cacacccatc     1260
tcagcagatc tgtcagcttt cccgcttttg ttagagggtg atatcatgct tcctgggggg     1320
agctctggaa gacaatgagc agccactttc ctctagatac aataggcgga gtcaggaagg     1380
tagtattgac attgctgggg cctaggagct actcactgct cggtggccgt cagatggtga     1440
accggcgtaa ccttggcaca caggcctggg ctgtacaagg cgtctggctg cagggccaaa     1500
gaggactcca ccctagggac aggagtactt cagacatctg ggaatctggg atgggttta     1560 aaattcagat cccaatataa aaaacaact cccaaacaaa cagcagcaat taaaaaaaaa      1620
aaaaaaaacc agcctcccaa gtaaaacaat aatggtacc                            1659

<210> SEQ ID NO 42
```

```
<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: primer F51

<400> SEQUENCE: 42
cccagtgtct ctgatttagg gagagcacct gag                              33

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: primer R51

<400> SEQUENCE: 43
ccagactgcc ttgggaaaag cgcctc                                      26

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: primer F52

<400> SEQUENCE: 44
cagtgagagt cttctctgtc cctcaatcgg ttctg                            35

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: primer R52

<400> SEQUENCE: 45
tggatgtgga atgtgtgcga ggccag                                      26

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: primer F31

<400> SEQUENCE: 46
aatcaaagag gcgaactgtg tgtgagaggt cc                               32

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: primer R31

<400> SEQUENCE: 47
cggctcccca aaatgtggaa gcaagc                                      26

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: primer F32

<400> SEQUENCE: 48
```

-continued

```
gaatccatct tgctccaaca ccccaacatc                                30
```

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: primer R32

<400> SEQUENCE: 49

```
cgcctcctct ccccagtctc cccttg                                    26
```

<210> SEQ ID NO 50
<211> LENGTH: 4998
<212> TYPE: DNA
<213> ORGANISM: Mus sp.

<400> SEQUENCE: 50

```
tccacccacc tgtttctcac gtccccggcc ttcctagtta acttcatggt taaagaagcc    60
tcacccgggg agggtgtggt gccacagaag gaagggtgct cccacaagcc ccagtgtct   120
ctgatttagg gagagcacct gagcccagtg agagtcttct ctgtccctca atcggttctg   180
aaattcccca cttgccctcc ttatccaggg acagggctg cccacccat tcaggacagt    240
agtcttaaac tcgtagccaa cagactttt attgggctgg gagaaagaga tgaggctcct    300
gaagctcagc cgagtgggct ctgattccta cttctcagag gtcgggcagc ccagccaata   360
ctgagcaatg gagcgtgggt agggaggatt cacagagtcc actcgccggg ttctaaggtt   420
gactcggtag tatttgtctg aaagaaagaa tggaaaaagg gttatgtgag attctgcctg   480
atcctgtcca ctggtcccaa gaaggataaa ggctttttct cagaagggaa agtgaacatc   540
caccaagcag ataatgtcac catctacagg ctgtgttcag cacccaggga ccaagacctg   600
caggcaaggc ctagccaaaa ccagtctaag gagtagaaaa gggctcccac ctccagagaa   660
gaaatagacg ctctgaatgg gctcgcaggt ggcaggtaca agccagtcca tatcataatc    720
atagttgttg taggttccta gcccactctc ctcgctggag aacaaagaga accagattga   780
acgtgatgaa cgacgggagt tcgagctctg gctgcgtctg tggccacgcc ctcggcgtga   840
acgatagcgc tttcggcttc tacgcttaga ctttctgtttt ttggcttggg cagagtggga   900
taaggagcca gtgacgtaga tgcggccggc catagcagcg tccactttcc ctggcacacc   960
atgccagttc cggctgatga attggggttc tctggctcca tctgtaacag ggaaggggtt  1020
aatgcacttg gcagattctg gctttgattt ctccagcaag gttgtctgtc tatctattta  1080
tctatcttta tctatgtatc tatctatata tctatgtatc tatctatcta tcatctacct  1140
acctacttac ctatctatgt atctatctat ctatcatcta cctacctact tacctatcta  1200
cctatttatt tgtttgtttg ttttctttga acaggatct tagcacctac ctatggctgg   1260
tttgcaactc actatgaagc cataactggc ctcttaactc acaaagatcc acttgcctgt  1320
gtctctgagt gctgggatta aaagcatgtg ccactacacc cagctccagt aggaccttta  1380
gaacacattt gctatgcctt gcctaagaca cacaactcag tccccaggcc ccagcctccc  1440
tgtctagagc tttttcccat cctctctcca ctgtatccct tgaatctctg ccccatccga  1500
aacccctcag cgcgcagccc ctccttctgc tgtgttaggc aaagtccaag gtatgggatc  1560
caaatagagc caagcctcat cccccaaaag tcaacagaag caaagtctag ccagagcaaa  1620
cagctcttga tcgatggtgt cacagttcca ggcccctccc ctggaagccc ccactatcac  1680
```

```
agcccagttt ccagagaaag aagccagcct tgctctccct ccataccaga ggatctgccc    1740
cagaagagga gttcgaaaat gttctcccag ctgtcccgct gaagcaaggc aaagtgctca    1800
aacacggctg acagagagct gccttcgcac tcctcctggc tgggttgctg ctgaaattcg    1860
tactcccagt actgcttccc tgaggagcag aacagctggc atcaggagag atctgaccaa    1920
ggcagagagg aatcatggaa tagaacaggg actccaccac ctgccccctt ctcctccacc    1980
ctgagtaccc ttgaagaagt agacccttc ccggccactg taacggtggg caggaagggc    2040
gaacgctgca tcaacattgt ctggtatgcc actgaagcct tcggagatgt ttcggggata    2100
accagggtcc aggaccccat cctcaaagcg ccagtactga ctaccctgaa agacagagat    2160
cagaagggtg aggacatacc gctggccaca gaagcagtcc tatatcctaa actggctgtc    2220
acctgctcct ggagtccctg actgctttgt cttcacagct ccccagcacg tccatggcac    2280
cctttacctt gcctcagact taggtctggt accttgaaca gtaggtcttc cccctgacag    2340
ttgatgcgag tgaaggcagc atcgatgggg ccctcaatgc cccagacatc ttggataagt    2400
ttggggtacc caggcctcac tgccgtctca tctagctcat agcagtactg ccctagaaca    2460
ggggaaactg tgtgagaagc agatgagcct aaggcagatc cgaccgccac cagacctgtc    2520
catagagtca cctcggaagg caaagaggga cccattcttg agatccgtga aggcgtcaaa    2580
gggctttcca ctgcacagtt cttcctctgg aaactcaggg gtcccttgat cagtggtgtc    2640
gggccttagg atctcctcct gttgctccac tttaggcgct ggggtgcttg gctgttcctc    2700
aggatctagg aaggctgtcg gctttagagt gccgtccgtc cgaggattta ggtcaccggg    2760
tggagaggtg ttctcggggtt gcacaccggt gttggtattg ttcttgggct cctccacgta    2820
gtcatagctc caataatcat cctctggcat agtgaacacg tccccccgcg ttactgcagg    2880
cagaacgggg agcagtgagt gtcaggctgt ggagggagcc ccaggcccac ccaccagggc    2940
tctgaactca ccttggggct tgcactgctc catgtagtcg gcacagcagc tctgatagta    3000
agtgcaaagc tcgtcacact gacacttctt gctggccatg aaaccctgag tgcagcggcc    3060
cttgcatgac tctatgggag ggaatatcag gtttacagcc caatctaggg cacctgccca    3120
acctgcactt ccctaggtac ccaccaatcc cctcccacac cttggtcagc cagagaaacc    3180
catgccacca gggctagtat gaaaaagggc ctcaggggtg ccatggcagg cctctagccc    3240
agggccttgg caagctgggc gcggagcttc tggaatctcg ctgtcctgcc tgaaaaaaga    3300
agcagactga agaagagttc ctagttccct gggtttctgc cctttatttg ctcatcctct    3360
ggcccagccc cattgccctc ctccaaacac agctgcagca aagggtcaca ttcccagaac    3420
cccagcccca ggagagctgg gaaacagaaa accctcgcca agaccaaagt cagtagggtc    3480
acgggcagga gggataacac gcttagctta gctggggagg tggaaagaag catgtgttgt    3540
caccctctga gccagtcccg ttaatctccc tgagccttac ttttttataaa gtgggaccat    3600 ggtgccttgc ctcatcaggt gttgagagat tccgtgagct agaacagaca aaacgtttcg    3660
tgcctggagt agcttccaac tcattcccat aagccgttat cgatttactg tttgatcagg    3720
ctaggtgctt gtcccatcct accccccgct tcgaatctgg attttggggg caagaagggg    3780
ggttggggga gagctggcaa gcactttggg ggaggttttc ttttcttctc ataaaagaac    3840
aaagcttcat ttctggcctc tccttgttct ctctaagctg ggtgttacag cataggaagt    3900
agtgggtcag agtctattct tctttctttta ttttttttag atttatttat tttatgtttt    3960
gtgtataagt gtctgctcac atgtgcatct gtgcaccaca tgcatgtctt gtgtctatgg    4020
aggtcagaag agggctttga ataccctgga actggagttt tgaacagtta tgagctgccg    4080
```

-continued

```
tgtggatgct gagaatcaaa cccaggtcct ctgtaagaac aagtactctt aaaggctgag    4140
ccatctttcc agtcccagag cccattcctg aggctttcac taatccattg atcctcgggg    4200
gaccaccctg gccacacctt caatgacctc atttattta  aaaaaaaaat ggactcattg    4260
ggcatacttt ctagactcac atactaagtg ggatttctct ataaagaagt gctcactggg    4320
gtagagtgcc aggttttggg ccaaattcca agcactggca cacttctgaa gcccctccgt    4380
tttctgttct gtaatcacag gcgagcgtgc ctttggtgtc tcttctctat ggaccgcagt    4440
agtctcagcg gcaaaatgaa acactaaatt ttactcccta cagacgcgtg aagcctaagt    4500
ggaaaccggc attaaagggc tttaagaatc tcaactgcga ttctttaacc atccggaggg    4560
gacgtggata catgtagcca gcttgcttcc acattttggg gagccgagcg agcggtagga    4620
aatggaagac agctctttac agccctttct acagcatctt gcacaccacc aagggagac    4680 tggggagagg aggcggagcc aggtgtgggc gtggctggag acctggggta ggcttgcgcc    4740
tgcgtcgggg gcggagcccg tgaaacctag aggcggggcg tcaaatcctt gactctgctg    4800
ctcagaggcg tggttgctgt tgagcatctt agctccgctg tgcttagatt ggagcagcgc    4860
tttgttccgg gcaccggcgt ctctaccctc ccgcgtctgg tccatgcttc tctctccctt    4920
catgcccttc ctaagtcgct gagtcccgga gctgccctcc tccttctgct tctacacttg    4980
tagcccagca cctttacc                                                  4998

<210> SEQ ID NO 51
<211> LENGTH: 11176
<212> TYPE: DNA
<213> ORGANISM: Mus sp.

<400> SEQUENCE: 51
gcagctgggc aaacgttggc gatgccggtg caaagtatat acccggtggt tagcagaagc      60
tgagaacttt tagccgaaag ccggctccct aagccgaagc taggcaagta ggggaagaaa     120
aagaaaaaaa aaattccaga gaagcttcca gagcctcctc ctcttccctc ttccttcaaa     180
aggactgcaa gtccgcagtc accctccacc agcaagagt  tagggcctcg aaccccggtc     240
acgctgcctc cgcctcctgc cgaacgtaac gggggacccg tgcgtaaagc gtgacgcgct     300
ggaatcctcc gtctgacgcg gggcacgcac aggccgcagc ccctccgccc gccccgcccc     360
tgacgtccgg gcacgttcta ttttggaacg ccgaggccac gttgctaagg gagggggcag     420
cgtggctttg tgattggctg tcgcgcgcag ctttagccaa tcagcgttcc cttcctattt     480
gtagagcgta gctcccttcc ttgcttttg  tggttcttcc cgtgctgggg gtctccaaga     540
ggagagctag gattcttgtc gcgatcggga ctcgttgtca ccccatggtc tgcgaggact     600
tgtgtggacc tggtctgttg tcataagcta gaggcttttg gctgagtgtt agcgcctcta     660
agggggaact gaaggcctca tccttctcag gcacacatat acgtgctcct gagctctaga     720
cactcagtcc ttccgaggtg ttcaaacact agatgagcta gcctacggag aggcagccag     780
gtggtctcta aaaggtctgc cttcccttag ttcccaggct ctgattggcc agggattcag     840
cccttccctc gccacgcccc ctagagtagt taagcctcta ggattccact tgcgggaagg     900
gggggggggg gggcgtgatg gacgcttctt ggggacgcag atcctatgtc accccatccc     960
ctgcaagaca gtctgagaga ttctcgctgt cacttttctc tgcctatcag ttcactgaaa    1020
cctgtcagtc tcactgggaa gagacagaca ctcggaaggg atgctctcaa ctcttaggcc    1080
ggtcccccaa caccgttgga actgggatct ccgcctgcgg gagccctcat gcagtggggg    1140
```

-continued

```
gtgtgtttgt gtgtgagtgg agaggaaggc ttggctaagg cctctccctc tccctccctc    1200
tgtggtgggg gttgggggt tttggctgta tgtgtgtgtg aatgtctgtg gctccatccc     1260
gggagtttgt caccaggttc tgtccagcct cctctcccac ccaccccccc acacctaaga    1320
gtcaccaacc cggggtgtga ttcaccaccc gctggaaccg tgcaacctt ccccgaggaa     1380 gaaggaggag gtagaaggca gttgaacaga atctctcatt aaccactgcg tcacggtgta    1440
gtggaagggt gggtgttgtg gcttttttgcc tgtgacacac acatccacac ccgctcaccc   1500
tgtgctcact cacagggtcg gtctctctta tctctcttgg gcgtgtgtgt gtcggtggct    1560
ttgtttgtgt gtctacgcct gtgtgtgtat gtctcacccc gtaggagtgc gccggtctcg    1620
gggaaatgcc cggctccttc gtgccaacgg tcaccgcaat cacaaccagc caggatcttc    1680
agtggctcgt gcaacccacc ctcatctctt ccatggccca gtcccagggg cagccactgg    1740
cctcccagcc tccagctgtt gacccttatg acatgccagg aaccagctac tcaaccccag    1800
gcctgagtgc ctacagcact ggcggggcaa gcggaagtgg tgggccttca accagcacaa    1860
ccaccagtgg acctgtgtct gcccgtccag ccagagccag gcctagaaga ccccgagaag    1920
agacagtaag tatgaggcct caggagttgg gatggaggag cctagctagg gatgtgggct    1980
cagtttgtac agtgccttgc tgccatgcat gaagatccct agcacagcat aagccaggag    2040
tggttatgca gacctgtaac cccagctctc agaaggtgga ggcaggagga gcaggagttc    2100
gaggccagcc tgtgctactt atggagtcca gcctgcactg caagagatca ttattttcaa    2160
aagttggcct tgggggagg tgggtgaggg aagtaagaga aagtgacagt aattttgtca     2220
cttaatagtt ggaggttcct ctgaggcctc aagtctgaag gaactttacc attctggcca    2280
gtgaggagta ggggttatta tttgggttc aggaggaagg aagttttctt agggctgata     2340
gaggtacccc cagatctcat ggtccttatc tctgactcag cttaccccag aagaagaaga    2400
aaagcgaagg gttcgcagag agcggaacaa gctggctgca gctaagtgca ggaaccgtcg    2460
gagggagctg acagatcgac ttcaggcggt aaggaggagt ctgggggtgt cttgaggccg    2520
tgctgggagc actctgcctt gttcttcccc cgtttctcac tgtgcctgtg tcctaaacga    2580
ggaaaccccc tcttagggaa cagggtcag tataggctga tggagtggct ccatatgcat     2640
gctcagaccc atgcccactt actttcgact gttccccact ttccctgaat atgtccccac    2700
atgtcaccct cctggctttc tctcagccta aggagacaag ctagaggagg taattctctc    2760
accttctttt cttcactaaa taataatcca ttttgccttc ctgcctccat ttttttttcc    2820
tgagctgggg atctacctgt cgtagttcag ccctcctccc ccaacttgat agcctcaagt    2880
ttcagcccct ggctgagatg ccatcatcct gactggctct ggctggaaac tattttgtgc    2940
taagtcaatt ccttgtctgc tacttcagct atctacagty ctgccgaact tgagctggtg    3000
gcgcccacca agcccacttc tttctctctt ttttacctca gtgcaacccc ccacacacaa    3060
aacttcatgc ctgcccttg aaaccagggt gcgtctctga ctccccgtcg ggaggctgaa     3120
ggagatgggt aacagaacct cattaaaaac aacacataag cattacctac tgactcaaca    3180
aactgtagtg ttttttcttt ttcctctcaa aaaattattt cgtttgttta tttattattt    3240
gcttatgttt gagtgagtgc tggtgcacca cagcacacat acgaggtcag agggaaattt    3300
tcatagtttg ttctctcctt ccgtgttgtg ggtgcttgct ggcaatctcc ttcactcagt    3360
gagctacaat gccccttct gcccttaag gcagagtact ccttagtaca gggggaccct      3420
ttcctcggcc tctcaaagtt gagattacaa atgttcacca tcacaccagg cttggagttc    3480
ttgcctatca gtgacgtcca ctcctgccta gcttcttccc aaccatcttt tagtctgatg    3540
```

```
gggaaaccga ggcacgagta gcatggtcta ccaggatttc ctcttagggg acggtcccct    3600
cagttgggag ggagctgtcc agcccctgg atcagcagca agaatgtatg agtgtggggt    3660
tgggcgggtg aagctactct gtgtggtcgc tgaccagcaa ttctcctttc tctgtctcct    3720
atgacctggc cctgctggga tccattagga aactgatcag cttgaagagg aaaaggcaga    3780
gctggagtcg gagatcgccg agctgcaaaa agagaaggaa cgcctggagt ttgtcctggt    3840
ggcccacaaa ccgggctgca agatccccta cgaagagggg ccggggccag gcccgctggc    3900
cgaggtgaga gatttgccag gtcaacatc cgctaaggaa gacggcttcg gctggctgct    3960
gccgccccct ccaccaccgc ccctgccctt ccagagcagc cgagacgcac cccccaacct    4020
gacggcttct ctctttacac acagtgaagt tcaagtcctc ggcgacccct tccccgttgt    4080
tagcccttcg tacacttcct cgtttgtcct cacctgcccg gaggtctccg cgttcgccgg    4140
cgcccaacgc accagcggca gcgagcagcc gtccgacccg ctgaactcgc cctcccttct    4200
tgctctgtaa actctttaga caaacaaaac aaacaaaccc gcaaggaaca aggaggagga    4260
agatgaggag gagaggggag gaagcagtcc gggggtgtgt gtgtggaccc tttgactctt    4320
ctgtctgacc acctgccgcc tctgccatcg gacatgacga aggacctcc tttgtgtttt     4380 gtgctctgtc tctggttttc tgtgcccccgg cgagaccgga gagctggtga cttttgggggac   4440 agggggtggg gcgggatga acaccctcc tgcatatctt tgtcctgtta cttcaaccca    4500
acttctgggg atagatggct gactgggtgg gtaggtggg gtgcaacgcc caccttttggc   4560 gtcttacgtg aggctggagg ggaaagagtg ctgagtgtgg ggtgcagggt gggttgaggt    4620
cgagctggca tgcacctcca gagacccca acgaggaaat gacagcaccg tcctgtcctt    4680 ctttccccc acccacccat ccaccctcaa gggtgcaggg tgaccaagat agctctgttt    4740
tgctccctcg ggccttagct gattaactta acatttccaa gaggttacaa cctcctcctg    4800
gacgaattga gcccccgact gagggaagtc gatgccccct ttgggagtct gctaaccccca   4860 cttcccgctg attccaaaat gtgaaccccct atctgactgc tcagtctttc cctcctggga    4920
aaactggctc aggttggatt ttttttcctcg tctgctacag agccccctcc caactcaggc    4980
ccgctcccac ccctgtgcag tattatgcta tgtccctctc accctcaccc ccaccccagg    5040
cgcccttggc cgtcctcgtt gggccttact ggttttgggc agcaggggc gctgcgacgc    5100 ccatcttgct ggagcgcttt atactgtgaa tgagtggtcg gattgctggg cgcgccggat    5160
gggattgacc cccagccctc caaaacttttt cctgggcctc cccttcttcc acttgcttcc    5220 tcccctcccct tgacagggag ttagactcga aaggatgacc acgacgcatc ccggtggcct    5280
tcttgctcag gcccccagact tttctctttt aagtccttcg ccttccccag cctaggacgc    5340
caacttctcc ccaccctggg agcccgcat cctctcacag aggtcgaggc aattttcaga    5400
gaagttttca gggctgaggc tttggctccc ctatcctcga tatttgaatc cccaaatagt    5460
ttttggacta gcatacttaa gaggggggctg agttcccact atcccactcc atccaattcc    5520
ttcagtccca aagacgagtt ctgtcccttc cctccagctt tcacctcgtg agaatcccac    5580
gagtcagatt tctatttctct aatattgggg agatgggccc taccgcccgt ccccgtgct    5640 gcatggaaca ttccataccc tgtcctgggc cctaggttcc aaacctaatc ccaaaccccca    5700 cccccagcta tttatccctt tcctggttcc caaaaagcac ttatatctat tatgtataaa    5760
taaatatatt atatatgagt gtgcgtgtgt gtgcgtgtgc gtgcgtgcgt gcgtgcgtgc    5820
gagcttcctt gttttcaagt gtgctgtgga gttcaaaatc gcttctgggg atttgagtca    5880
```

```
gactttctgg ctgtcccttt ttgtcacttt tttgttgttg tctcggctcc tctggctgtt    5940
ggagacagtc ccggcctctc cctttatcct ttctcaagtc tgtctcgctc agaccacttc    6000
caacatgtct ccactctcaa tgactctgat ctccggtctg tctgttaatt ctggatttgt    6060
cggggacatg caattttact tctgtaagta agtgtgactg ggtggtagat ttttacaat     6120 ctatatcgtt gagaattctg ggtggaaatg tctgatcagg agaagggcct gccactgccg    6180
accacaattc attgactcca tagccctcac ccaggctgta tttgtgattt ttttcatttt    6240 gttttttgt attttgcacc tgaccccggg ggtgctgggg cagtctatca ctgggcagct     6300
cccctccccc ccttggttct gcactgtcgc caataaaaag cttttaaaaa actgtatcct    6360
tcaggtcaaa gtgtctgttt tccctggaca tctactacat ggcttccttt cagaaaaacg    6420
gagtttggat tgctagggaa gtcttgctgg cacttagtgg gacgcctaac gaatcagaac    6480
ctacaacggg actaaaagga agtggagact tgctaggttt tcccatgttc ccaggctggg    6540
ccacctactt gaaaaaataa ggggcggaaa agtgtaaggt accaaatttg gtgaagggtc    6600
tgggagaatt tcatgatcgg aaaagaattt attcaccttg ggtgtgcaat gaactttcag    6660
caacagttaa gggcaagggt gtaaaagctg gcacaacttg taaatccta gcatttgaga    6720 ggtggaggca aggggatcaa ctggtggagt tcagtgtcat gtggatcgta gataccaagc    6780
gcaaagatct gctatgggga gagggcttgg tacaccaggg gagccagaag tttcgtggtg    6840
agggtagtgg agggcaagtg gagagtgaga gttagcctca gggagattct acaggcaatg    6900
atgcagagtt cagacgctcc ctttgaaagc actagagagc cgcagcaggt tttgagcaga    6960
gaaggttaga gttaggtggt ctcttctagc ccatcccagg ctgaggagga cgctgagggt    7020
ttcaagaagg atcgagaatg gaaagcagag gagaagaagg atccaagagg catggaggag    7080
gcagaacaca tttctcttct ttaatagcaa gcctggaaag gataacttgc tgcaggagga    7140
gatgctcacc agtcgggtgg tctaggggt tcttggaaaa gagaaggcat ttgctcaagc     7200
ctcggttccc ccattctcgc tcttctgtca gcttgtcttc cattaagtgt gtgtctcaag    7260
gccaccctgc tcaggactcc ttgtgagacg accttctatg ctcgagttca ttaaaaacac    7320
aattgcctgg tgccgtgctc tctccactgg ctcagttacc tcaaaagacc agggctaaag    7380
gtgtgatcac aactctatcc ccattactgc tccaacgcag agacaggact gagccggagt    7440
gaacaaatga acaaaaatga ctaataatgc atgcgtgatt aaatacataa aagagcagat    7500
gactggatga gcaaatcgtt taaggagaga cagcaagatc ctagaatttt ggagactaat    7560
ttaaatccat ctttgagatg catttggtcg gaaattcctg ggaggaaaaa aagtgtaaat    7620
atgaagagag aataaatgag aatagggtg gcttcagaga ggttaactgc gcgctggtcg      7680
cttttgtaca agaatgtgaa ttgcaggag caaaatggga tagatactcc cgcccgaaag      7740
gtggaattga accactctgt cgctaaacag ctacaggttt gaagcctgca ccccagacca    7800
ctgaggatca tccgggcgaa aggagctatt ttcagttagt tatataaagg cgagatacta    7860
ctacttttta cacttatggt cattatttgt ggtatacagt agataattaa tttcaatggt    7920
ttcgaacatt tttttcact ttttcttgtg aacatgtgtt tcctcagtaa agtgttccgt      7980
gaatgactct actaactaaa agtaagtag cttcatttgc atagcgcctt gcattttggg      8040
aagcagcgcc taaagtgcct gtctcccctaa ctaaaagcag aattttttgc aaagtgaaaa    8100
gtcagtttta ttttgtttg tttgtttgct tgtttgtttt taatggaaaa acttctcacg      8160
cggcccattc gtagcagaat tcgagatttt ctgcaagcga gaagcaagac tttcgtaggg    8220
tctgacggca cgcggccgca gagcgacacc tgccgttgct ttatagaact gcaagtatgt    8280
```

-continued

| | |
|---|---|
| agggaatcta ctgagtccct aggtgatgga gttgacaacc aactcccctt gagtttagac | 8340 |
| gctaaaaacc atccctttt atatttatgt gattagccca gggaaactaa ggctcagaca | 8400 |
| tggataatac cacagccgag ttcttgtagc ccaactccct aggggaaatg aaacctacag | 8460 |
| ttgtggtttt aatatgcttg gcccaggggc agtggccta ttggcaggag tggccttatt | 8520 |
| agcggaggtg taccttgtta gagaagtgtg tcacttggag gcgaggtttt gaggtacgta | 8580 |
| tgctcaagtc tggccagtgt gatcctggct gtctgcagaa cgtggtctcc ttctggctgc | 8640 |
| cttcggatca aggtgtagaa ctctcagctc cttctccagc accatgtctg cctgcttaat | 8700 |
| gctttgcttc tttccatgac gataatgaac tgtgcctctg aaactgtaag tcagcccccc | 8760 |
| agttacatgt tttctttat aagagttgca tatatatg tatgtatata tgtatgtata | 8820 |
| tatgtatgta tatatata tatataaaa cagggtctca ctctttagct ctggctggcc | 8880 |
| tgaaattcac tatgtagccc aggattgcct gaactttgaa gcaatcttcc tgcctcagcc | 8940 |
| tcccaatggt attacaggca tgagtcacaa caagccattt aaatcttatg atgacttata | 9000 |
| agaagacaga aaatcagagt tcctttacct agttcacaga tccctacaat ctaacctcgt | 9060 |
| tcgctccata aacagcccta ccccaccctc ctggaactgc tttgaggaat gctgcaggct | 9120 |
| ctcacaggca cactcctcct tggttaatct cttcagcctg gttgccttcc cccccatgt | 9180 |
| ccatgtggcc caaagcctct catcctgttc tcaaatacca ctagctagta aggctccccg | 9240 |
| acctgacccg gtttaaatat tagaaaaggg tcactttctc cctgccacag acaaccaaac | 9300 |
| caccatatgc ttgtcactta ctacctgact atgaaggtta atagatgtct tcacaacctt | 9360 |
| tctctgagcc tcagtttccc cacctgcata atgcatctga gacacagaat ccctagagc | 9420 |
| tgtggttctc ctcattccta gtgctgggac ccttaatac atttcctcat gttgtggtga | 9480 |
| ccccaccacc accataaaat tatttccatt gatacttcat aactgtaatt ttttctattg | 9540 |
| ttatgaatag taatgtaagc atttgtgttt cccagtgatc ttagatgacc ctgtggaaga | 9600 |
| gtcattccac cccaaagggg tccccaccac aagttaagaa ttcctgccat agaggaatca | 9660 |
| cagggaccat ggattaacac ttgggtcgac ttttgggctg ccttctggga ggcgctagag | 9720 |
| ctaatgacag ctacatcaat ttctgaaatt ttgtgtgtgt gtgtgtgtgt gtgtgtgtgt | 9780 |
| gtgtgtgtgt gccctgagtc gggtgctgag ataggccagt ggctttagtg ttcctggacc | 9840 |
| cattactcac cagaactctc ccctcacctg attctttgat gtgaacacta tgtcttcata | 9900 |
| gtggcggtgg caatagcagc aacagtgaac taaattttaa aagtagaact cagctggaga | 9960 |
| tacaaatatt gcagttttga agttggggtg gattgtctaa taacttaata acataaccca | 10020 |
| gaagagaggc cccttggtct tgcaaacttt atatgcctca gtacagggga acgccagggc | 10080 |
| caagaagtgg gagtgggtgg gtaggggagc agggtgggg gagggtatag gggactttcc | 10140 |
| ggatagcatt tgaaatgtaa atgaagaaaa tatctaataa aaatttgaaa aaaaatgtta | 10200 |
| ccccagtttg gcctggatct cactacctca accagactgg catgtgactc tgctgagatc | 10260 |
| tgcctacttc tgcctcctgg gtgcagaaga caatttttgg aagttagttc tcttcttcca | 10320 |
| tcttgtggat tccagggatt gaactcgggt catcaggctt ggctgcaagt gacttactta | 10380 |
| ggtgtctccc agaccctctc ggtttgatta gttagatgct gcacttcatg cctgactttc | 10440 |
| gcactatgta gatagagcaa tgtctataac atctcctaca atgatatgta tatcaagagc | 10500 |
| caagtgatga gatggctcag tgggtaagag cacagactgc tcttccaaag gtcccgagtt | 10560 |
| caaatcccag caatcacata gtggcttcca ttccctctta tggaatgtct gaagactgct | 10620 |

```
acagtgtact tacatataat aaataaataa atcttaaaaa aaaaaaaccc agccgggcgt   10680
ggtggcgcac gcctttaatc ccagcacttg ggaggcagag gcaggcggat tcctgagttc   10740
gacgccagcc tggtctacag agtgagttcc acgacagcca gaactacaca gagaaaccct   10800
gtctcgaaaa aaaaaagaga gagagggaag tgagagcgca ataatcttaa catttctgtg   10860
gttgtctttg ctgtagtcta ttctgataag caatgctggc ttgctcccaa ggtaggaagt   10920
aacatttctt tataaaaggt atttgctctg ctttattttt ctgttttatt tatggtgctg   10980
aggatggaac ccaggaccct tggcaagcaa ggctagctgt ttaccactga gccatactcc   11040
agccttgcac tgggggattc taggcaaggg ttctaccact gagccacact ccccaccccc   11100
atccctctct ggaagattct aggcagttcc atacctagcc tttgatcttt taagacggtc   11160
ttactagagc tcagtt                                                  11176
```

METHODS AND COMPOSITIONS FOR SCREENING FOR ANGIOGENESIS MODULATING COMPOUNDS

TECHNICAL FIELD

This invention is in the field of molecular biology and medicine. More specifically, it relates to novel vector constructs, compositions, and methods of use thereof for screening compounds in host cells or transgenic animals. Further, the invention relates to vector constructs and methods of use thereof to generate transgenic organisms, particularly transgenic mice.

BACKGROUND

A requirement for cellular inflow of nutrients, outflow of waste products, and gas exchange in most tissues and organs is the establishment of a vascular supply. Several processes for blood vessel development and differentiation have been identified. One such process is termed "vasculogenesis" and takes place in the embryo. This process consists of the in situ differentiation of mesenchymal cells into hemoangioblasts, which are the precursors of both endothelial cells and blood cells. "Angiogenesis" is a second such process and involves the formation of new blood vessels from a preexisting endothelium. This process is required for (i) the development of embryonic vasculature, and (ii) a variety of postnatal processes, including, but not limited to, wound healing, tissue regeneration, and organ regeneration. Further, angiogenesis has been identified as a requirement for solid tumor growth and uncontrolled blood cell proliferation.

Vascular Endothelial Growth Factor (VEGF; also designated as vascular permeability factor (VPF) has been identified as a regulator of normal and pathological angiogenesis. VEGF is a secreted growth factor having the following properties (i) an endothelial cell specific mitogen; (ii) angiogenic in vivo and induces vascular permeability; (iii) VEGF expression (and expression of its receptors) has been correlated with vasculogenesis and angiogenesis during embryonic development; and (iv) VEGF is expressed in tumor cells. The VEGF receptor appears to be expressed exclusively in adjacent small blood vessels. VEGF appears to play a crucial role in the vascularization of a wide range of tumors including, but not limited to, breast cancers, ovarian tumors, brain tumors, kidney and bladder carcinomas, adenocarcinomas and malignant gliomas. Tumors have been shown to produce ample amounts of VEGF which stimulates the proliferation and migration of endothelial cells (ECs). This is thought to induce tumor vascularization by a paracrine mechanism.

The angiogenic effect of VEGF appears to be mediated by its binding to high affinity cell surface VEGF receptors (VEGFR).

SUMMARY OF THE INVENTION

The invention provides methods and compositions relating to the VEGFR-2 gene transcriptional promoter. The compositions include recombinant regulators of gene expression comprising the VEGFR-2 promoter of SEQ ID NO:32, further sequences isolated based on the teachings disclosed herein, or deletion mutants thereof, typically at least 10, 20, 25, 50, or 100 bp in length, where the sequences maintain cis transcriptional regulatory activity.

The invention also provides hybridization probes and replication/amplification primers having a hitherto novel VEGFR-2 specific sequence contained in SEQ ID NO:32 (including its complement and analogs and complements thereof having the corresponding sequence, e.g., in RNA) and sufficient to effect specific hybridization thereto (i.e., specifically hybridize with SEQ ID NO:32 in the presence of genomic DNA).

The invention also provides cells and vectors comprising the disclosed VEGFR-2 regulators, including cells comprising such regulators operably linked to non-VEGFR-2 coding sequences (i.e., a heterologous coding sequence). Such cells find use in the disclosed methods for identifying agents or compounds that regulate the activity of a VEGFR-2 promoter. In an exemplary method, the cells are contacted with a candidate agent, under conditions wherein, but for the presence of said agent, the VEGFR-2 promoter exhibits a first expression of a reporter; detecting the presence of a second expression of the reporter, wherein a difference between said first and said second expression of the reporter indicates that the agent affects the expression mediated by the VEGFR-2 promoter.

In another aspect, this invention relates to a substantially purified nucleic acid molecule comprising a VEGFR-2 promoter region (i.e., an isolated polynucleotide). In one embodiment the isolated polynucleotide comprises the sequence presented as SEQ ED NO:32, and fragments thereof which maintain cis-acting transcriptional activity, in particular, a regulator of gene expression derived from SEQ ID NO:32 wherein said polynucleotide sequence has cis transcriptional regulatory activity. A further embodiment includes, an isolated polynucleotide comprising, a cis-acting transcription regulator having X contiguous nucleotides, wherein (i) the X contiguous nucleotides have at least about 90% identity to Y contiguous nucleotides derived from SEQ ID NO:32, (ii) X equals Y, and (iii) X is greater than or equal to 50. Exemplary values of X include, but are not limited to, X is greater than or equal to 500, X is greater than or equal to 3563, X is in the range of 50–3570 including all integer values in that range.

The invention also includes an expression cassette comprising the above-described polynucleotides. The invention also relates to expression vectors comprising the aforementioned polynucleotide sequences and host cells transformed with these expression vectors.

In another aspect, the invention also relates to methods for detecting test agents which modulate transcription of the VEGFR-2 promoters described above. Such methods include contacting a host cell transformed with an expression vector comprising the VEGFR-2 promoter DNA sequence operably linked to a reporter sequence with the test agent and comparing the level of transcription produced by the test agent to the level of transcription produced in its absence. The invention also relates to transgenic or chimeric animals whose cells express a heterologous gene under the transcriptional control of a VEGFR-2 promoter, and methods of using such animals as described herein.

In another aspect, the invention relates to the above embodiments wherein the promoter sequence is derived from Tie2.

These and other embodiments of the present invention will be apparent to those of skill in the art in view of the teachings herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3C includes five pages labeled 3C-1 through 3C-5 and shows the nucleotide sequence of vitronectin.

FIG. 4B includes twelve pages labeled 4B-1 through 4B-12 and shows the nucleotide sequence of FosB.

FIGS. 5A through 5I depict the nucleotide sequence of the entire promoter region of the VEGFR2 mouse gene (SEQ ID NO:32).

FIG. 6 depicts PCR conditions for genomic screening for promoters useful in exemplary targeting constructs of the present invention.

FIG. 11 depicts the nucleotide sequence of a 511 bp enhancer region of VEGFR2 (SEQ ID NO:35).

FIG. 15 includes fourteen pages labeled 15-1 through 15-14 and depicts the nucleotide sequence of the entire promoter region of the Tie2 mouse gene (SEQ ID NO:40).

FIGS. 16A, 16B and 16C depict the nucleotide sequence of a 1.7 kb enhancer region of Tie2 (SEQ ID NO:41).

MODES FOR CARRYING OUT THE INVENTION

Figure 1:
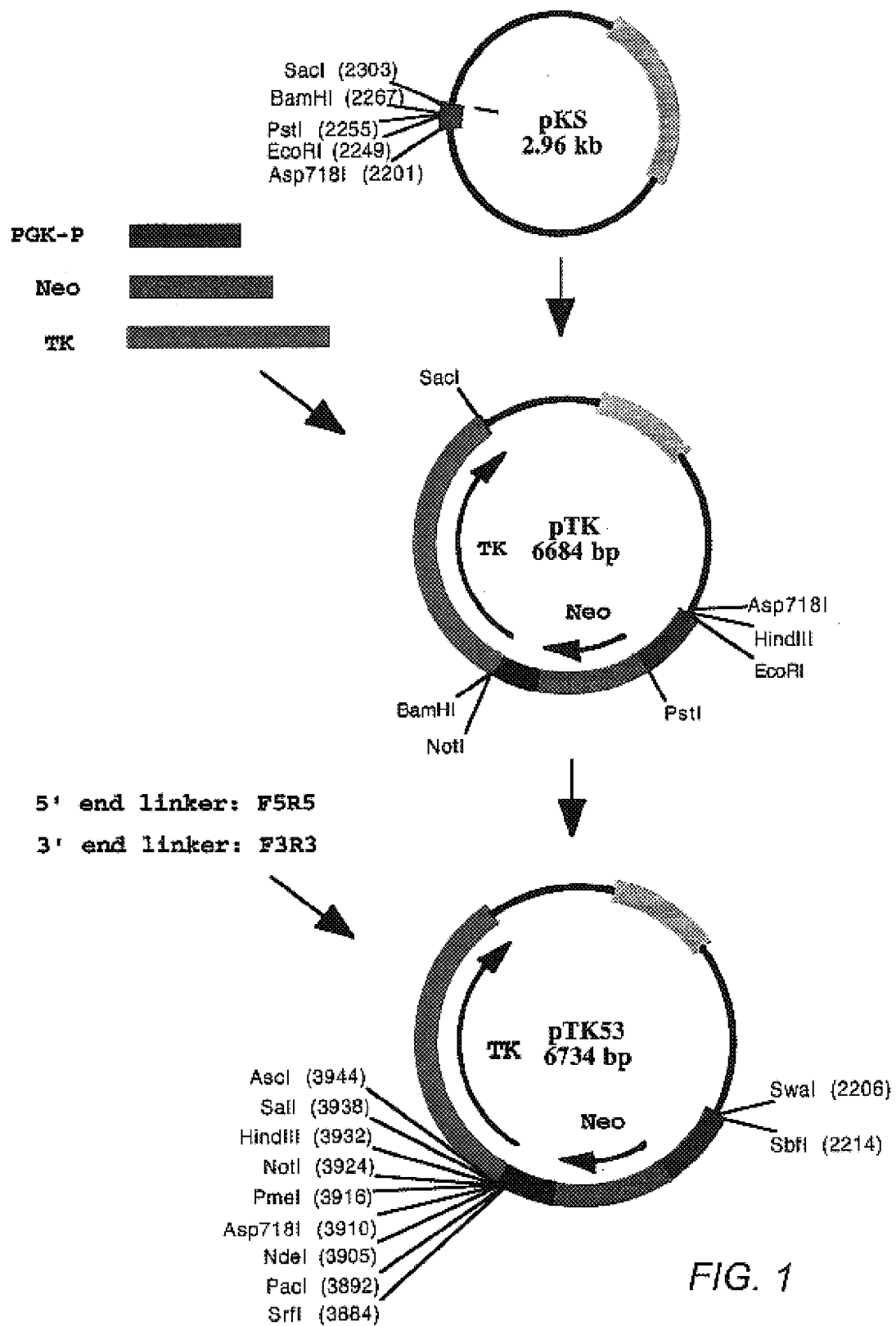
FIG. 1 is a schematic depicting construction of the pTK53 vector. Polynucleotides encoding PGK-P, Neo and TK and 5' and 3' linkers are introduced into a pKS backbone to produce the vector designated pTK53.

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

The practice of the present invention will employ, unless otherwise indicated, conventional techniques of molecular biology, microbiology, cell biology and recombinant DNA, which are within the skill of the art. See, e.g., Sambrook, Fritsch, and Maniatis, MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2. A PRACTICAL APPROACH (M. J. McPherson, B. D. Hames and G. R. Taylor eds., 1995) and ANIMAL CELL CULTURE (R. I. Freshney. Ed., 1987).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to "an antigen" includes a mixture of two or more such agents.

Definitions

As used herein, certain terms will have specific meanings.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

A "transcription factor" as used herein typically refers to a protein (or polypeptide) which affects the transcription, and accordingly the expression, of a specified gene. A transcription factor may refer to a single polypeptide transcription factor, one or more polypeptides acting sequentially or in concert, or a complex of polypeptides.

Typical "control elements", include, but are not limited to, transcription promoters, transcription enhancer elements, transcription regulating elements (transcription regulators), transcription termination signals, polyadenylation sequences (located 3' to the translation stop codon), sequences for optimization of initiation of translation (located 5' to the coding sequence), translation enhancing sequences, and translation termination sequences. Transcription promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters. A transcription regulator is a cis-acting element that affects the transcription of a gene, for example, a region of a promoter with which a transcription factor interacts to induce expression of a gene.

"expression enhancing sequences" typically refer to control elements that improve transcription or translation of a polynucleotide relative to the expression level in the absence of such control elements (for example, promoters, promoter enhancers, enhancer elements, and translational enhancers (e.g., Shine and Delagarno sequences)).

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "heterologous sequence" as used herein is typically refers to either (i) a nucleic acid sequence that is not normally found in the cell or organism of interest, or (ii) a nucleic acid sequence introduced at a genomic site wherein the nucleic acid sequence does not normally occur in nature at that site. For example, a DNA sequence encoding a polypetide can be obtained from yeast and introduced into a bacterial cell. In this case the yeast DNA sequence is "heterologous" to the native DNA of the bacterial cell. Alternatively, a promoter sequence from a Tie2 gene can be introduced into the genomic location of a fosB gene. In this case the Tie2 promoter sequence is "heterologous" to the native fosB genomic sequence.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter= none; strand=both; cutoff=60, expect=10; Matrix= BLOSUM62; Descriptions=50 sequences; sort by=HIGH SCORE, Databases=non-redundant, GenBank+EMBL+ DDBJ+PDB+GenBank CDS translations+Swiss protein+ Spupdate+PIR. Details of these programs can be found at the following internet address: http://www.ncbi.nlm.gov/cgi-bin/BLAST. When claiming sequences relative to sequences of the present invention, the range of desired degrees of sequence identity is approximately 80% to 100% and integer values therebetween. Typically the percent identities between the disclosed sequences and the claimed sequences are at least 80–82%, 85–90%, preferably 92%, more preferably 95%, and even more preferably 98% sequence identity to the reference sequence (i.e., the sequences of the present invention).

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 85%–90%, more preferably at least about 90%–95%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

"Nucleic acid expression vector" or "expression cassette" refers to an assembly which is capable of directing the expression of a sequence or gene of interest. The nucleic acid expression vector includes a promoter which is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

"Luciferase," unless stated otherwise, includes prokaryotic and eukaryotic luciferases, as well as variants possessing varied or altered optical properties, such as luciferases that produce different colors of light (e.g., Kajiyama, N., and Nakano, E., *Protein Engineering* 4(6):691–693 (1991)).

"Light-generating" is defined as capable of generating light through a chemical reaction or through the absorption of radiation.

A "light generating protein" or "light-emitting protein" is a protein capable of generating light in the visible spectrum (between approximately 350 nm and 800 nm). Examples include bioluminescent proteins such as luciferases, e.g., bacterial and firefly luciferases, as well as fluorescent proteins such as green fluorescent protein (GFP).

"Light" is defined herein, unless stated otherwise, as electromagnetic radiation having a wavelength of between about 300 nm and about 1100 nm.

"Animal" as used herein typically refers to a non-human mammal, including, without limitation, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

A "transgenic animal" refers to a genetically engineered animal or offspring of genetically engineered animals. A transgenic animal usually contains material from at least one unrelated organism, such as from a virus, plant, or other animal. The "non-human animals" of the invention include vertebrates such as rodents, non-human primates, sheep, dogs, cows, amphibians, birds, fish, insects, reptiles, etc. The term "chimeric animal" is used to refer to animals in which the heterologous gene is found, or in which the heterologous gene is expressed in some but not all cells of the animal.

"Analyte" as used herein refers to any compound or substance whose effects (e.g., induction or repression of a specific promoter) can be evaluated using the test animals and methods of the present invention. Such analytes include, but are not limited to, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds/analytes can be employed in the practice of the present invention.

As used herein, the term "positive selection marker" refers to a gene encoding a product that enables only the cells that carry the gene to survive and/or grow under certain conditions. For example, plant and animal cells that express the introduced neomycin resistance (Neo$^r$) gene are resistant to the compound G418. Cells that do not carry the Neo$^r$ gene marker are killed by G418. Other positive selection markers will be known to those of skill in the art. Typically, positive selection markers encode products that can be readily asssayed. Thus, positive selection markers can be used to determine whether a particular DNA construct has been introduced into a cell, organ or tissue.

"Negative selection marker" refers to gene encoding a product which can be used to selectively kill and/or inhibit growth of cells under certain conditions. Non-limiting examples of negative selection inserts include a herpes simplex virus (HSV)-thymidine kinase (TK) gene. Cells containing an active HSV-TK gene are incapable of growing in the presence of gangcylovir or similar agents. Thus, depending on the substrate, some gene products can act as either positive or negative selection markers.

The term "homologous recombination" refers to the exchange of DNA fragments between two DNA molecules or chromatids at the site of essentially identical nucleotide sequences. It is understood that substantially homologous sequences can accommodate insertions, deletions, and substitutions in the nucleotide sequence. Thus, linear sequences of nucleotides can be essentially identical even if some of the nucleotide residues do not precisely correspond or align (see, above).

A "knock-out" mutation refers to partial or complete loss of expression of at least a portion the target gene. Examples of knock-out mutations include, but are not limited to, gene-replacement by heterologous sequences, gene disruption by heterologous sequences, and deletion of essential elements of the gene (e.g., promoter region, portions of a coding sequence). A "knock-out" mutation is typically identified by the phenotype generated by the mutation.

A "single-copy gene" as used herein refers to a gene represented in an organism's genome only by a single copy at a particular chromosomal locus. Accordingly, a diploid organism has two copies of the gene and both copies occur at the same chromosomal location.

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence (e.g., a DNA sequence for mammals) that occupies a specific physical location (a "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids (e.g., phage attachment sites), wherein the gene does not encode an expressed product. Typically, a gene includes coding sequences, such as, polypeptide encoding sequences, and non-coding sequences, such as, promoter sequences, poly-adenlyation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

"Isogenic" means two or more organisms or cells that are considered to be genetically identical. "Substantially isogenic" means two or more organisms or cells wherein, at the majority of genetic loci (e.g., greater than 99.000%, preferably more than 99.900%, more preferably greater than 99.990%, even more preferably greater than 99.999%), there exists genetic identity between the organisms or cells being compared. In the context of the present invention, two organisms (for example, mice) are considered to be "substantially isogenic" if, for example, inserted transgenes are the primary differences between the genetic make-up of the mice being compared. Further, if, for example, the genetic backgrounds of the mice being compared are the same with the exception that one of the mice has one or several defined mutation(s) (for example, affecting coat color), then these mice are considered to be substantially isogenic. An example of two strains of substantially isogenic mice are C57BL/6 and C57BL/6Tyr C2j/+.

A "pseudogene" as used herein, refers to a type of gene sequence found in the genomes, typically, of eucaryotes, where the sequence closely resembles a known functional gene, but differs in that the pseudogene is non-functional. For example, the pseudogene sequence may contain several stop codons in what would correspond to an open reading frame in the functional gene. Pseudogenes can also have deletions or insertions relative to their corresponding functional gene. If, for example, in a genome there is a functional gene and a related pseudogene, the functional gene is considered to be a single-copy gene (accordingly, the pseudogene is considered to be single-copy as well).

A "non-essential gene" refers to a gene whose deletion, disruption, elimination, reduction of gene function, or mutation is non-lethal, and does not obviously adversely affect the organisms' ability to mature and reproduce. A "non-essential gene with no phenotype" refers to a non-essential gene whose deletion, disruption, elimination, reduction of gene function or mutation has no deleterious effect on the organism. Typically there are no phenotypically reflected gene dosage effects associated with modification of a non-essential gene with no phenotype—for example, deletion, disruption or mutation of both copies of a non-essential gene with no phenotype in a diploid organism has essentially the same effect as deletion, disruption, or mutation of one of the two copies present in the diploid organism. In the context of the present invention, a non-essential gene is typically one whose function has been eliminated (e.g., by a deletion mutation) and such elimination of function was non-lethal and the organism developed, matured, and was able to reproduce.

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations."

By "replacement sequence" is meant a polynucleotide sequence that is substituted for at least a portion of the native or wild-type sequence of a gene.

"Linear vector" or "linearized vector," as used herein, is a vector having two ends. For example, circular vectors, such as plasmids, can be linearized by digestion with a restriction endonuclease that cuts at a single site in the plasmid. Preferably, the targeting vectors described herein are linearized such that the ends are not within the targeting sequences.

General Overview

In one aspect, the present invention relates to vector constructs, cells containing the constructs, methods of screening compounds, and methods of creating transgenic animals to be used, for example, as screening or test systems. Methods of using the constructs, cells, and transgenic animals of the present invention include, but are not limited to, studies involving tumor growth and other disease conditions. Exemplary promoters useful in the practice of the present invention include mouse VEGFR-2 and mouse Tie2.

In one embodiment, the present invention relates to novel promoters for the mouse VEGFR-2 receptor gene, nucleic acid constructs comprising such promoters operatively linked to genes encoding a gene product, such as, a reporter, a protein, polypeptide, hormone, ribozyme, or antisense RNA, recombinant cells comprising such nucleic acid constructs, screening for therapeutic drugs using such cells (e.g., screening for compounds that modulate VEGFR-2-mediated angiogenesis), and endothelial tissue-specific gene expression using these novel promoter sequences.

In yet another aspect of the present invention, transgenic, non-human mammals are constructed where a single-copy, non-essential gene is replaced by a reporter expression cassette, preferably a gene encoding a light-generating protein, such as a luciferase-encoding gene, operably linked to a promoter. A variety of promoters are useful in the practice of the present invention, for example, promoters derived from genes associated with tumorigenesis or angiogenesis. Thus, an exemplary promoter can be one that is associated with proteins induced during tumorigenesis, for instance in the presence of tumor generating compounds or of tumors themselves. In this way, expression of the reporter cassette is induced in the animal when, for example, tumors are present, and progression of the tumor can be evaluated by non-invasive imaging methods using the whole animal. Another exemplary promoter is one that is derived from a gene associated with angiogenesis. Because the promoter is linked to a reporter such as luciferase, non-invasive monitoring of the progression of angiogenesis is possible. Various forms of the different embodiments of the invention, described herein, may be combined.

Non-invasive imaging and/or detecting of light-emitting conjugates in mammalian subjects was described in U.S. Pat. No. 5,650,135, by Contag, et al., issued 22 Jul. 1997, and herein incorporated by reference. This imaging technology can be used in the practice of the present invention in view of the teachings of the present specification. In the imaging method, the conjugates contain a biocompatible entity and a light-generating moiety. Biocompatible entities include, but are not limited to, small molecules such as cyclic organic molecules; macromolecules such as proteins; microorganisms such as viruses, bacteria, yeast and fungi; eukaryotic cells; all types of pathogens and pathogenic substances; and particles such as beads and liposomes. In another aspect, biocompatible entities may be all or some of the cells that constitute the mammalian subject being imaged, for example, cells carrying the vector constructs of the present invention expressing a reporter expression cassette.

Light-emitting capability is conferred on the biocompatible entities by the conjugation of a light-generating moiety. Such moieties include fluorescent molecules, fluorescent proteins, enzymatic reactions giving off photons and luminescent substances, such as bioluminescent proteins. In the context of the present invention, light emitting capability is typically confered on target cells by having at least one copy of a light-generating protein, e.g., a luciferase, present. In preferred embodiments, luciferase is operably linked to appropriate control elements which can facilitate expression of a polypeptide having luciferase activity. Substrates of luciferase can be endogenous to the cell or applied to the cell or system (e.g., injection into a transgenic mouse, having cells carrying a luciferase construct, of a suitable substrate for the luciferase, for example, luciferin). The conjugation may involve a chemical coupling step, genetic engineering of a fusion protein, or the transformation of a cell, microorganism or animal to express a light-generating protein.

Targeting Constructs

Figure 3A:
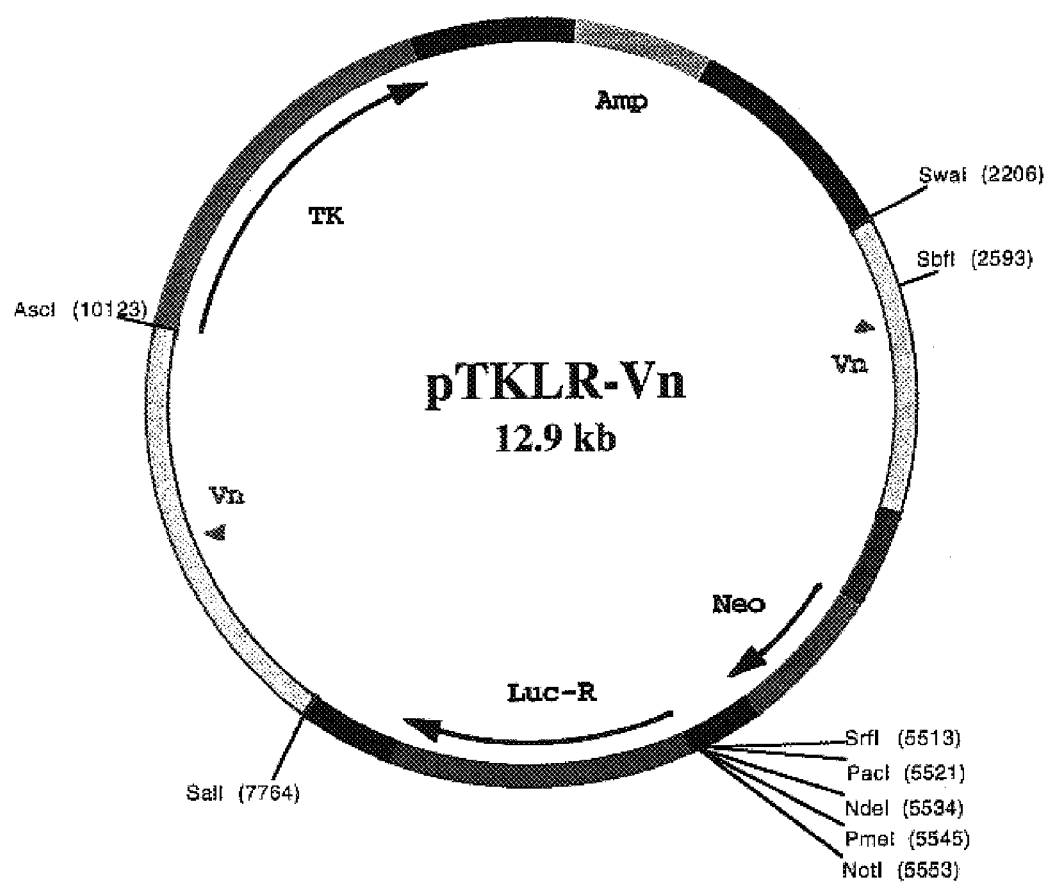
FIG. 3A is a schematic depicting the vector pTKLR-Vn. Sequences homologous to the vitronectin gene are inserted in to pTK-LucR such that they flank the Neo$^r$ gene and the Luc-R coding sequence.
Figure 3B:
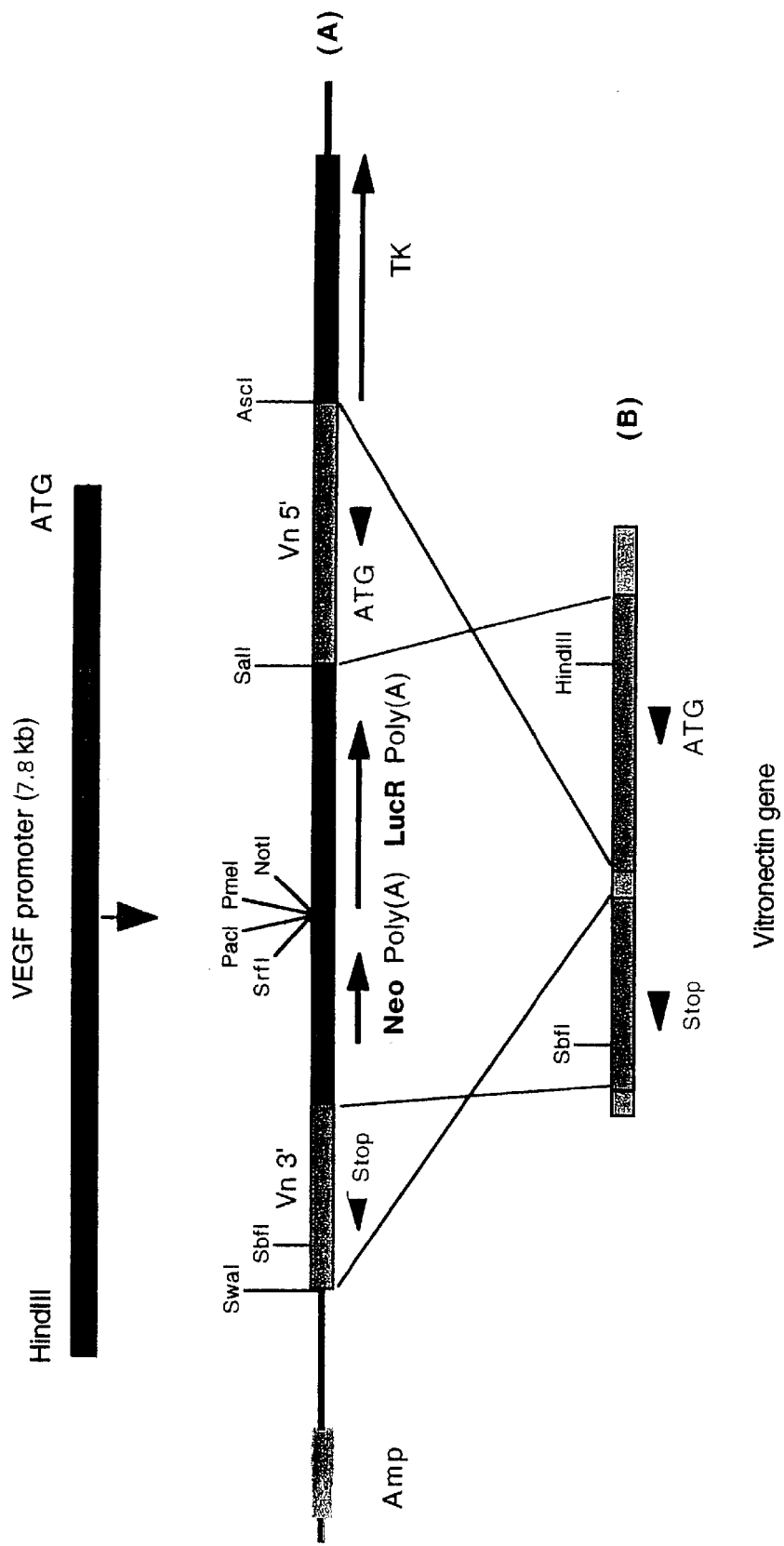
FIG. 3B is a schematic depicting targeting of the linearized pTKLR-Vn vector to the vitronectin chromosomal locus. The VEGF promoter is cloned into the polylinkers between Neo and Luc-R. Upon homologous recombination, the Neo-VEGF-LucR transgene is inserted into the Vn gene. In the figure, (A) shows the targeting vector pTKLR-Vn and (B) shows the mouse vitronectin gene. In the figure, Neo—neomycin resistance encoding sequences; TK—thymidine kinase encoding sequences; LucR—red luciferase from pGL3Red (Dr. Christopher Contag, Stanford University, Stanford, Calif.). Regions bearing Vn gene translational start and stop codons are indicated with arrows. Poly(A) sequences are place upstream of the polylinker to prevent or minimize read-through translation.
Figure 13:
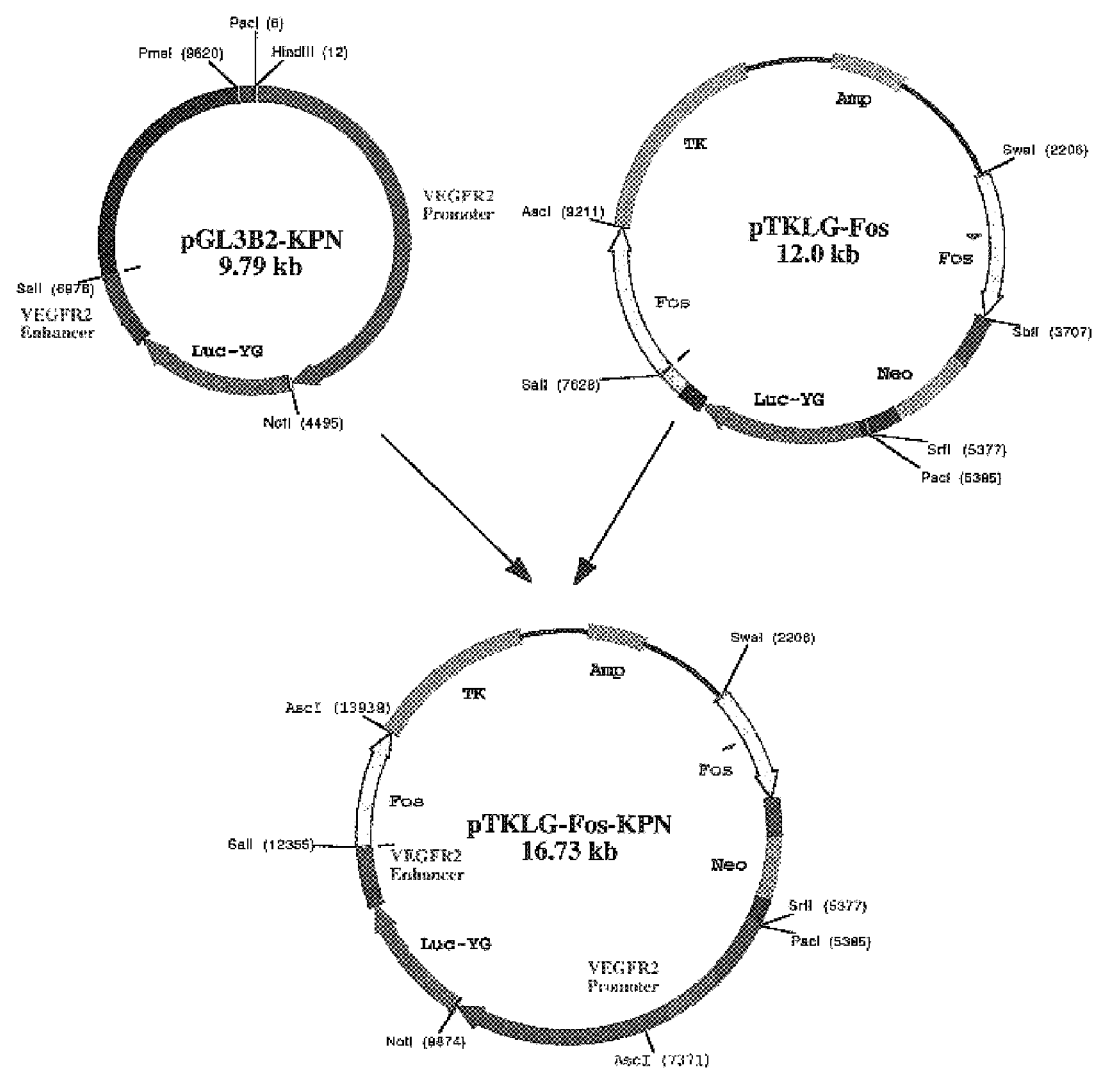
FIG. 13 is a schematic depicting engineering of the pTKLG-Fos-KPN construct made using pGL3B2-KPN (FIG. 12) and pTKLG-Fos.
Figure 18:
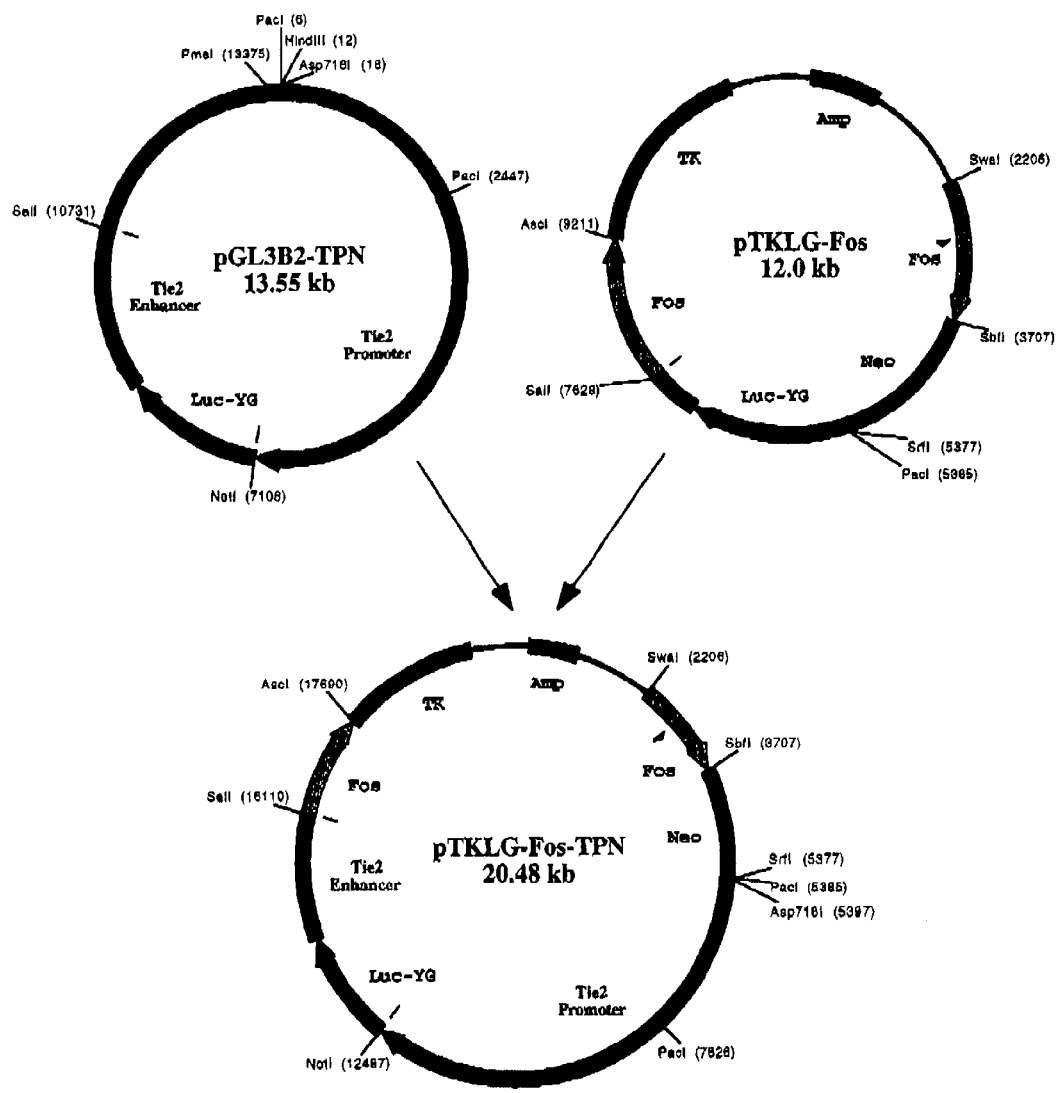
FIG. 18 is a schematic depicting engineering of the pTKLG-Fos-KPN construct made using pGL3B2-KPN (FIG. 17) and pTKLG-Fos.

The targeting cassettes described herein typically include the following components: (1) a suitable vector backbone; (2) a polynucleotide encoding a light generating protein, (3) a promoter operably linked to the luciferase-encoding gene, wherein the promoter is heterologous to the coding sequences of the light generating protein; (4) a sequence encoding a positive selection marker; (5) insertion sites flanking the sequence encoding the positive selection marker and the polynucleotide encoding a light generating protein gene, for insertion of sequences which target a single-copy, non-essential chromosomal gene; and, optionally, (6) a sequence encoding a negative selection marker. Exemplary targeting constructs are shown in FIGS. 3B, 13 and 18 and described in Examples 1–3.

Suitable vector backbones generally include an F1 origin of replication; a colE1 plasmid-derived origin of replication; polyadenylation sequence(s); sequences encoding antibiotic resistance (e.g., ampicillin resistance) and other regulatory or control elements. Non-limiting examples of appropriate backbones include: pBluescriptSK (Stratagene, La Jolla, Calif.); pBluescriptKS (Stratagene, La Jolla, Calif.) and other commercially available vectors.

In one aspect of the invention, the light generating protein is luciferase. Luciferase coding sequences useful in the practice of the present invention include sequences obtained from lux genes (procaryotic genes encoding a luciferase activity) and luc genes (eucaryotic genes encoding a luciferase activity). A variety of luciferase encoding genes have been identified including, but not limited to, the following: B. A. Sherf and K. V. Wood, U.S. Pat. No. 5,670,356, issued 23 Sep. 1997; Kazami, J., et al., U.S. Pat. No. 5,604,123, issued 18 Feb. 1997; S. Zenno, et al, U.S. Pat. No. 5,618,722; K. V. Wood, U.S. Pat. No. 5,650,289, issued 22 Jul. 1997; K. V. Wood, U.S. Pat. No. 5,641,641, issued 24 Jun. 1997; N. Kajiyama and E. Nakano, U.S. Pat. No. 5,229,285, issued 20 Jul. 1993; M. J. Cormier and W. W. Lorenz, U.S. Pat. No. 5,292,658, issued 8 Mar. 1994; M. J. Cormier and W. W. Lorenz, U.S. Pat. No. 5,418,155, issued 23 May 1995; de Wet, J. R., et al, *Molec. Cell. Biol.* 7:725–737, 1987; Tatsumi, H. N., et al, *Biochim. Biophys. Acta* 1131:161–165, 1992; and Wood, K. V., et al, *Science* 244:700–702, 1989; all herein incorporated by reference. Eukaryotic luciferase catalyzes a reaction using luciferin as a luminescent substrate to produce light, whereas prokaryotic luciferase catalyzes a reaction using an aldehyde as a luminescent substrate to produce light.

Wild-type firefly luciferases typically have an emission maxima at about 550 nm. Numerous variants with differing emission maxima have also been studied. For example, Kajiyama and Nakano (*Protein Eng.* 4(6):691–693, 1991; U.S. Pat. No. 5,330,906, issued 19 Jul. 1994, herein incorporated by reference) teach five variant firefly luciferases generated by single amino acid changes to the *Luciola cruciata* luciferase coding sequence. The variants have emission peaks of 558 nm, 595 nm, 607 nm, 609 nm and 612 nm. A yellow-green luciferase with an emission peak of about 540 nm is commercially available from Promega, Madison, Wis. under the name pGL3. A red luciferase with an emission peak of about 610 nm is described, for example, in Contag et al. (1998) *Nat. Med.* 4:245–247 and Kajiyama et al. (1991) *Prot. Eng.* 4:691–693.

Positive selection markers include any gene which a product that can be readily asssayed. Examples include, but are not limited to, a hprt gene (Littlefield, J. W., Science 145:709–710 (1964), herein incorporated by reference), a xanthine-guanine phosphoribosyltransferase (gpt) gene, or an adenosine phosphoribosyltransferase (aprt) gene (Sambrook et al., supra), a thymidine kinase gene (i.e "TK") and especially the TK gene of herpes simplex virus (Giphart-Gassler, M. et al., Mutat. Res. 214:223–232 (1989) herein incorporated by reference), a nptII gene (Thomas, K. R. et al., Cell 51:503–512 (1987); Mansour, S. L. et al., Nature 336:348–352 (1988), both references herein incorporated by reference), or other genes which confer resistance to amino acid or nucleoside analogues, or antibiotics, etc, for example, gene sequences which encode enzymes such as dihydrofolate cc reductase (DHFR) enzyme, adenosine deaminase (ADA), asparagine synthetase (AS), hygromycin B phosphotransferase, or a CAD enzyme (carbamyl phosphate synthetase, aspartate transcarbamylase, and dihydroorotase). Addition of the appropriate substrate of the positive selection marker can be used to determine if the product of the positive selection marker is expressed, for example cells which do not express the positive selection marker nptII, are killed when exposed to the substrate G418 (Gibco BRL Life Technology, Gaithersburg, Md.).

The targeting vector typically contains insertion sites for inserting targeting sequences (e.g., sequences that are substantially homologous to the target sequences in the host genome where integration of the targeting vector/expression cassette is desired). These insertion sites are preferably included such that there are two sites, one site on either side of the sequences encoding the positive selection marker, luciferase and the promoter. Insertion sites are, for example, restriction endonuclease recognition sites, and can, for example, represent unique restriction sites. In this way, the vector can be digested with the appropriate enzymes and the targeting sequences ligated into the vector.

Optionally, the targeting construct can contain a polynucleotide encoding a negative selection marker. Suitable negative selection markers include, but are not limited to, HSV-tk (see, e.g., Majzoub et al. (1996) *New Engl. J. Med.* 334:904–907 and U.S. Pat. No. 5,464,764), as well as genes encoding various toxins including the diphtheria toxin, the tetanus toxin, the cholera toxin and the pertussis toxin. A further negative selection marker gene is the hypoxanthine-guanine phosphoribosyl transferase (HPRT) gene for negative selection in 6-thioguanine.

Exemplary promoters and single-copy, non-essential genes for use in the vector constructs and methods of the present invention are described below.

Promoters

The targeting constructs and transgenic animals described herein contain a sequence encoding a luciferase gene operably linked to a promoter. The promoter may be from the same species as the transgenic animal (e.g., mouse promoter used in construct to make transgenic mouse) or from a different species (e.g., human promoter used in construct to make transgenic mouse). The promoter can be derived from any gene of interest. In one embodiment of the present invention, the promoter is derived from a gene whose expression is induced during angiogenesis, for example pathogenic angiogenesis like tumor development. Thus, when a tumor begins to develop in a transgenic animal carrying a vector construct of the present invention, the promoter is induced and the animal expresses luciferase, which can then be monitored in vivo.

Exemplary promoters for use in the present invention are selected such that they are functional in a cell type and/or animal into which they are being introduced. Exemplary promoters include, but are not limited to, promoters obtained from the following mouse genes: vascular endothelial growth factor (VEGF) (VEGF promoter described in U.S. Pat. No. 5,916,763; Shima et al. (1996) *J. Bio. Chem.* 271:3877–3883; sequence available on NCBI under accession number U41383); VEGFR2, also known as Flk-1, (VEGFR-2 promoter described, for example, in Ronicke et al. (1996) *Circ. Res.* 79:277–285; Patterson et al. (1995) *J. Bio. Chem.* 270:23111–23118; Kappel et al. (1999) *Blood* 93:4282–4292; sequence available as accession number X89777 of NCBI database); Tie2, also known as Tek (Tie2 promoter described, for example, in Fadel et al. (1998) *Biochem J.* 338:335–343; Schlaeger et al. (1995) *Develop.* 121:1089–1098; Schlager et al. (1997) *PNAS USA* 94:3058–3063). VEGF is a specific mitogen for EC in vitro and a potent angiogenic factor in vivo. In a tumorigenesis study, it was shown that VEGF was critical for the initial subcutaneous growth of T-47D breast carcinoma cells transplanted into nude mice, whereas other angiogenic factors, such as, bFGF can compensate for the loss of VEGF after the tumors have reached a certain size (Yoshiji, H., et al., 1997 Cancer Research 57: 3924–28). VEGF is a major mediator of aberrant EC proliferation and vascular permeability in a variety of human pathologic situation, such as, tumor angiogenesis, diabetic retinopathy and rheumatoid arthritis (Benjamin L E, et al., 1997 PNAS 94: 8761–66; Soker, S., et al., 1998 Cell 92: 735–745). VEGF is synthesized by tumor cells in vivo and accumulates in nearby blood vessels. Because leaky tumor vessels initiate a cascade of events, which include plasma extravasation and which lead ultimately to angiogenesis and tumor stroma formation, VEGF plays a pivotal role in promoting tumor growth (Dvorak, H. F., et al., 1991 J Exp Med 174:1275–8). VEGF expression was upregulated by hypoxia (Shweiki, D., et al., 1992 Nature 359: 843–5). VEGF is also upregulated by overexpression of v-Src oncogene (Mukhopadhyay, D., et al., 1995 Cancer Res. 15: 6161–5), c-SRC (Mukhopadhyay, D., et al., 1995 Nature 375: 577–81), and mutant ras oncogene (Plate, K. H., et al., 1992 Nature 359: 845–8). The tumor suppressor p53 downregulates VEGF expression (Mukhopadhyay, D., et al., 1995 Cancer Res. 15: 6161–5).

A number of cytokines and growth factors, including PGF and TPA (Grugel, S., et al., 1995 J. Biological Chem. 270: 25915–9), EGF, TGF-b, IL-1, IL-6 induce VEGF mRNA expression in certain type of cells (Ferrara, N., et al., 1997 Endocr. Rev. 18: 4–25). Kaposi's sarcoma-associated herpesvirus (KSHV) encoded a G-protein-coupled receptor, a homolog of IL-8 receptor, can activate JNK/SAPK and p38MAPK and increase VEGF production, thus causing cell transformation and tumorigenicity (Bais, C., et al., Nature 1998 391:86–9). VEGF overexpression in skin of transgenic mice induces angiogenesis, vascularhyperpermeability and accelerated tumor development (Larcher, F., et al., Oncogene 1998 17:303–11).

VEGF-B (cDNA sequences available on databases) is a mitogen for EC and may be involved in angiogenesis in muscle and heart (Olofsson, B., et al., 1996 Proc Natl Acad Sci USA 93:2576–81). Shown in vitro, binding of VEGF-B to its receptor VEGFR-1 leads to increased expression and activity of urokinase type plasminogen activator and plasminogen activator inhibitor, suggesting a role for VEGF-B in the regulation of extracellular matrix degradation, cell adhesion, and migration (Olofsson, B., et al., 1998 Proc Natl Acad Sci USA 95:11709–14).

VEGF-C (see, e.g., U.S. Pat. No. 5,916,763 and Shima et al., supra) may regulate angiogenesis of lymphatic vasculature, as suggested by the pattern of VEGF-C expression in mouse embryos (Kukk, E., et al., 1996 Development 122: 3829–37). Although VEGF-C is also a ligand for VEGFR-2, the functional significance of this potential interaction is unknown. Overexpression of VEGF-C in the skin of transgenic mice resulted in lymphatic, but not vascular, endothelial proliferation and vessel enlargement, suggesting the major function of VEGF-C is through VEGFR-3 rather than VEGFR-2 (Jeltsch M, et al., 1997 Science 276:1423–5). Shown by the CAM assay, VEGF and VEGF-C are specific angiogenic and lymphangiogenic growth factors, respectively (Oh, S. J., et al., (1997) *Devel. Biol.* 188: 96–109). VEGF-C overexpression in the skin of transgenic mice resulted in lymphatic, but not vascular, endothelial proliferation and vessel enlargement (Jeltsch M, et al., 1997 Science 276:1423–5).

VEGF-D (cDNA sequences available on databases) is a mitogen for EC. Given that VEGF-D can also activate VEGFR-3, it is possible that VEGF-D could be involved in the regulation of growth and/or differentiation of lymphatic endothelium (Achen, M. G., et al., 1998 Proc Natl Acad Sci USA 95: 548–53). VEGF-D is induced by transcription facto c-Fos in mouse (Orlandini, M., 196 PNAS 93: 11675–80).

VEGFR-1 signaling pathway may regulate normal endothelial cell-cell or cell matrix interactions during vascular development, as suggested by the knockout study (Fong, G. H., et al., 1995 Nature 376: 65–69). Although VEGFR-1 has a higher affinity to VEGF than VEGFR-2, it does not transduce the mitogenic signals of VEGF in ECs (Soker, S., et al., 1998 Cell 92: 735–745). VEGFR-2 (see, e.g., Rönicke et al., Patterson et al., Kappel et al. (1999), supra) appears to be the major transducer of VEGF signals in EC that result in chemotaxis, mitogenicity and gross morphological changes in target cells (Soker, S., et al., 1998 Cell 92: 735–745). The cloning and sequencing of the 4.5 kb VEGFR2 promoter region is described herein (Example 3).

VEGFR-3 has an essential role in the development of the embryonic cardiovascular system before the emergence of lymphatic vessels, as shown by the knockout study (Dumont, D. J., et al., 1998 Science 282: 946–949). Neuropillin-1 (see, e.g., Soker et al. (1998) *Cell* 92:735–745) is a receptor for VEGF165. It can enhance the binding of VEGF165 to VEGFR-2 and VEGF165 mediated chemotaxis (Soker, S., et al., 1998 Cell 92: 735–745). Neuropillin 1 overexpression in transgenic mice resulted in embryonic lethality. The embryos possessed excess capillaries and blood vessels. Dilated vessels and hemorrhage were also observed (Kitsukawa, T., et al.,. 1995 Development 121: 4309–18).

Further promoters of interest include, but are not limited to, the following: Ang2 is expressed only at predominant vascular remodeling sites, such as ovary, placenta, uterus (Maisonpierre, P. C., et al., 1997 Science 277: 55–60). In glioblastoma angiogenesis, Ang2 is found to be expressed in endothelial cells of small blood vessel and capilaries while Ang 1 is expressed in glioblastoma tumor cells (Stratmann, A., 1998 Am J Pathol 153: 1459–66). Ang2 is up-regulated in bovine microvascular endothelial by VEGF, bFGF, cyrokines, hypoxia (Mandriota, S. J., 1998 Circ Res 83: 852–9). Ang2 transgenic overexpression disrupts angiogenesis, and is embryonic lethal (Maisonpierre, P. C., et al., 1997 Science 277: 55–60). Ang1 is widely expressed, less aboundant in heart and liver (Maisonpierre, P. C., et al., 1997 Science 277: 55–60). Ang1 is expressed in mesenchymal cells and may up-regulate the expression of Tie2 in the endothelial cells (Suri, C., et al., 1996 Cell 87: 1171–1180). Ang1 overexpression in the skin of transgenic mice produces larger, more numerous, and more highly branched vessels (Suri, C., et al., Science 1998 282:468–71).

Tie2 (see, e.g., Fadel et al.; Schlaeger et al. (1995), and Schlager et al. (1997), supra) is edothelial cell specific, upregulated during wound healing, follicle maturation (Puri, M. C., et al., 1995 EMBO J 14: 5884–91) and pathologic angiogenesis (Kaipainen, A., 1994 Cancer Research 54: 6571–77), such as, glioblastoma (Stratmann, A., 1998 Am J Pathol 153: 1459–66). Tie2 is also expressed in non-proliferating adult endothelium and edothelial cell lines (Dumont, D. J., et al. (1994) *Genes & Develop.* 8:1897–1909). A Tie2 activating mutation causes vascular dysmorphorgenesis (Vikkula M, et al., 1996 Cell 87: 1181–1190). Tie2 mutant overexpression in transgenic mice is embryonic lethal (Dumont, D. J., et al., supra). The cloning and sequencing of the 7.1 kb promoter region of Tie2 is described herein (Example 3).

Other promoters useful in the practice of the present invention include, by way of example, promoters derived from the sequences encoding the following polypeptide products: PTEN (dual specificity phosphatase); BAI (brain-specific angiogenesis inhibitor); KAI1 (KANGAI 1); catenin beta-1 (cadherin-associated protein, beta); COX2 (PTGS2 cyclooxygenase 2, a.k.a. prostaglandin-endoperoxide synthase 2); MMP2 (72 kDa Type IV-A collagenase); MMP9 (92 kDa type IV-B collagenase); TIMP2 (tissue inhibitor of metalloproteinase 2); and TIMP3 (tissue inhibitor of metalloproteinase 3).

PTEN is a tumor suppressor gene and encodes a protein of 403 amino acids. (Li et al. (1997) *Science* 275:1943–1946; DiCristofano et al. (1998) *Nature Genet.* 19:348–355). Overexpression of PTEN has been shown to inhibit cell migration and it is postulated that this protein may function as a tumor suppressor by negatively regulating cell interactions with the extracellular matrix or by negatively regulating the P13K/PKB/Akt signaling pathway. (Tamura et al. (1998) *Science* 280:1614–1617; Stambolic et al. (1998) *Cell* 95:29–29). Mutations in PTEN have been detected in cancer cell lines and in the germline of patients having Cowden disease, Lhermitte-Duclos disease and Bannayan-Zonana syndrome (diseases and syndromes which are characterized by hyperplastic/dysplastic changes in the prostate, skin and colon and which are associated with an increased risk of certain cancers, for example, breast cancer, prostate cancer and colon cancer). (Marsh et al. (1998) *Hum. Molec. Genet.* 7:507–515; Marsh et al. (1998) *J. Med. Genet.* 35:881–885; Nelen et al. (1997) *Hum. Molec. Genet.* 6:1383–1387).

BAI1 protein is predicted to be 1,584 amino acids in length and includes an extracellular domain, an intracellular domain and a 7-span transmembrane region similar to that of the secretin receptor. (Nishimori et al. (1997) *Oncogene* 15:245–2150). The extracellular region of BAI1 has a single Arg-Gly-Asp (RGD) motif recognized by integrins and also has five sequences corresponding to the thrombospondin type I (accession number 188060) repeats that can inhibit angiogenesis includes by basic fibroblast growth factor (bFGF, accession number 134920). Shiratsuchi et al. (1997) *Cytogenet. Cell Genet.* 79:103–108, cloned 2 other brain-specific angiogenesis inhibiting genes, designated BAI2 (accession number 602683) and BAI3 (accession number 602684). Thus, it is postulated that members of this gene family may play a role in suppression of glioblastoma.

KAI1 encodes a 267 amino acid protein which is a member of the leukocyte surface glyoprotein family. The protein has 4 hydrophobobic transmembrane domains and 1 large extracellular hydrophilic domain with three potential N-glycosylation sites. (Dong et al. (1995) *Science* 268:884–886). Molecular analysis of KAI1 is described, for example, in Dong et al. (1997) *Genomics* 41:25–32. KAI1 is a tumor metastasis suppressor gene that is capable of inhibiting the metastatic process in experimental animals. Expression of KAI1 is downregulated during tumor progression of prostate, breast, lung, bladder and pancreatic cancers in humans, apparently at the transcriptional or postranscriptional level. Mashimo et al. (1998) *PNAS USA* 95:11307–11311, found that the tumor suppressor gene p53 can directly inactivate the KAI1 gene by interacting with the region 5' to the coding sequence, suggesting a direct relationship between p53 and KAI1.

Catenin beta-1 is an adherens junction (AJ) protein, which are critical for establishing and maintaining epithelial cell layers, for instance during embryogenesis, wound healing and tumor cell metastasis. Molecular analysis, including description of sequence homology to plakoglobin (accession number 173325), homology to the drosophila gene "armadillo" and interactions with Lef1/Tcf DNA binding proteins, is described, for example, in Nollet et al. (1996) *Genomics* 32:413–424; McCrea et al. (1991) *Science* 254:1359–1361 and Korinek et al. (1997) *Science* 275:1784–1787. In addition, studies by Korinek et al., supra and Morin et al. (1997) *Science* 275:1787–1790, have indicated that APC (accession number 175100) negatively regulates catenin beta and that regulation of this protein is critical to the tumor suppressive effect of APC. Abnormally high levels of beta-catenin have been detected in certain human melanoma cell lines. (Rubinfeld et al. (1997) *Science* 275:1790–1792. Koch et al. (1999) *Cancer Res.* 59:269–273 report that childhood hepatoblastomas frequently carry a mutated degradation targeting box of the beta-catenin gene. Transgenic mice which express catenin beta under the control of an epidermal promoter undergo de novo hair morphogenesis and eventually these animals develop two types of tumors—epithelioid cysts and trichofolliculomas. Gat et al. (1998) *Cell* 95:605–614.

COX2 encodes a cyclooxygenase and is a key regulator of prostaglandin synthesis. (Hla et al. (1992) *PNAS USA* 89:7384–7388; Jones et al. (1993) *J. Biol. Chem.* 268:9049–9054). In particular, COX2 is generally considered to be a mediator of inflammation and overexpression of COX2 in rat epithelial cells results in elevated levels of E-cadherin and Bcl2. (Tsujii. & DuBois (1995) *Cell* 83:493–501). In co-cultures of endothelial cells and colon carcinoma cells, cells that overexpress COX2 produce prostaglandins, proangiogenic factors and stimulate both endothelial migration and tube formation. (Tsujii et al. (1998) *Cell* 93:705–716). Experiments conducted using APC knock-out mice have demonstrated that animals homozygous for a disrupted COX2 locus develop significantly more adenomatous polyps. (Oshima et al. (1996) *Cell* 87:803–809). COX-2 "knock out" mice develop severe nephropathy, are susceptible to peritonitis, exhibit reduced arachidonic acid-induced inflammation and exhibit reduced indomethacin-induced gastric ulceration. (Morham et al. (1995) *Cell* 83:473–482; Langenbach et al. (1995) *Cell* 83:483–492). Female mice that are deficient in cyclooxygenase 2 exhibit multiple reproductive failures. (Lim et al. (1997) *Cell* 91:197–208.

MMP2 is a metalloproteinase that specifically cleaves type IV collagen. A C-terminal fragment of MMP2, termed PEX, prevents normal biding to alpha-V/beta-3 and disrupts angiogenesis and tumor growth. (Brooks et al. (1998) *Cell* 92:391–400).

MMP9 is a collagenase secreted from normal skin fibroblasts. MMP9 null nice exhibit an abnormal pattern of skeletal growth plate vascularization and ossification. (Vu et al. (1998) *Cell* 93:411–422).

TIMP2 is a collagenase and appears to play a major role in modulating the activity of interstitial collagenase and a number of connective tissue metalloendoproteases. (Stetler-Stevenson et al. (1989) *J. Biol. Chem.* 264:17372–17378). Unlike TIMP1 and TIMP3, TIMP2 is not upregulated by TPA or TGF-beta. (Hammani et al. (1996) *J. Biol. Chem.* 271:25498–25505).

TIMP3 (Wilde et al. (1994) *DNA Cell Biol.* 13:711–718) is localized in the extracellular matrix in both its glycosylated and unglycosylated forms. Studies of mutant TIMP3 proteins have demonstrated that C-terminal trunctions do not bind to the extracellular matrix. (Langton et al. (1998) *J. Biol. Chem.* 273:16778–16781).

As one of skill in the art will appreciate in view of the teachings of the present specification, promoter sequences can be derived and isolated from known polypeptide sequences or from cDNA or genomic sequences, using method known in the art in view of the teachings herein, for example the promoter sequences of VEGFR2 and Tie2 were isolated and sequenced as described in Example 3 below. Another exemplary method of isolating promoter sequences using cDNA is via a GenomeWalker® kit, commercially available from Clontech (Palo Alto, Calif.), and described on page 27 of the 1997–1998 Clontech catalog.

Targeting Sequences: Non-essential Genes

Central to the present invention is the fact that the targeting constructs contain "targeting" sequences (flanking, for example, the luciferase-encoding sequence and promoter) derived from a single-copy, non-essential gene. These targeting sequences in the construct act via homologous recombination to replace at least a portion of the nonessential gene in the genome with the light-generating protein-encoding (e.g., luciferase-encoding) sequence operably linked to a promoter.

Non-limiting examples of targeting sequences for use in generating transgenic mice include sequences obtained from or derived from vitronectin, Fos B and galactin 3. A search of Mouse Knockout & Mutation Database (Genome Systems, Inc., St. Louis, Mo.) can be used to identify genes that have been knocked-out in mice where the generated knockout mice displayed no obvious defects. The chromosomal locus for all these genes can be used to target promoter-luciferase transgenes similar to what is described in Example 2. Single-copy, non-essential mouse genes identified in this manner include, but are not limited to, the following: Moesin (Msn), Doi Y., et al., J Biol Chem 1999, 274:2315–2321; Plasminogen activator inhibitor, type II (Planh2) and Planh1, Dougherty K. M., Proc Natl Acad Sci USA 1999, 96:686–691; Protein tyrosine phosphatase, receptor type, B (Ptprb), Elchebly et al. (1999) Science 283:1544–1548; Presenilin 1 (Psen1), Guo Q, et al. (1999) Proc Natl Acad Sci USA, 96:4125–4130; Protein kinase, mitogen-activated 9 (Prkm9)/SAPK/Erk/kinase 2 (Serk2), Kuan C Y et al. (1999) Neuron 4:667–676; CD152 antigen (Cd152)/CD86 antigen (Cd86)/CD80 antigen (Cd80), Mandelbrot D A, et al. (1999) J Exp Med, 189:435–440; Poly (ADP-ribose) polymerase (Adprp), Masutani M, et al. (1999), Proc Natl Acad Sci USA 96:2301–2304; Sodium channel, nonvoltage-gated 1 beta (Scnn1b), Pradervand S, et al. (1999) Proc Natl Acad Sci USA 96:1732–1737; Nuclear receptor coactivator 1 (Ncoa1), Qi C, et al. (1999) Proc Natl Acad Sci USA 96:1585–1590; Decay accelerating factor 1 (Daf1), Sun X, et al. (1999) Proc Natl Acad Sci USA 1999, 96:628–633; Necdin (Ndn), Tsai T F, et al. (1999) Nat Genet 22:15–16; Relaxin (Rln); Zhao L, et al. (1999) Endocrinology 140:445–453; Adenylyl cyclase 8 (Adcy8), Abdel-Majid R M, et al. (1998) Nat Genet 19:289–291; Leukemia inhibitory factor (Lif), Bugga L, et al. (1998) J Neurobiol 36:509–524; Lectin, galactose binding, soluble 3 (Lgals3) and Lgals1, Calnot C, et al. (1998) Dev Dyn 211:306–313; Urokinase plasminogen activator receptor (Plaur) Carmeliet P, et al. (1998) J Cell Biol 140:233–245; Nitric oxide synthase 1, neuronal (Nos1), Chao D S, et al. (1998) J Neurochem 71:784–789; Homeo box A7 (Hoxa7), Chen F, et al. (1998) Mech Dev 77:49–57; Myosin light chain, phosphorylatable, cardiac ventricles (Mylpc) Chen J, et al. (1998) J Biol Chem 273:1252–1256; Homeo box B7 (Hoxb7), Chen F, et al. (1998) Mech Dev 77:49–57; Nuclear factor of kappa light chain gene enhancer in B-cells inhibitor, alpha and beta (Nfkbia and Nfkbib), Cheng J D, et al. (1998) J Exp Med 6:1055–1062; Enolase 1, alpha non-neuron (Eno1), Couldrey C, et al. (1998) Dev Dyn 212:284–292; Xeroderma pigmentosum, complimentation group A (Xpa), De Vries A, et al. (1998) Exp Eye Res 1998, 67:53–59; Von Willebrand factor homolog (Vwf), Denis C, et al. (1998) Proc Natl Acad Sci USA 95:9524–9529; Lysosomal acid lipase 1 (Lip1), Du H, et al. (1998) Hum Mol Genet. 7:1347–1354; UNC-5 homolog (*C. elegans*) 3 (Unc5h3), Eisenman L M, et al. (1998) J Comp Neurol 394:106–117; Protein phosphatase 1, regulatory (inhibitor) subunit 1B (Ppp1r1b), Fienberg A A, et al. (1998) Science 281:838–842; Myelin-associated glycoprotein (Mag) Fujita N, et al. (1998) J Neurosci 18:1970–1978; Paraoxonase 1 (Pon1), Furlong C E, et al. (1998) Neurotoxicology 19:645–650; Brain derived neurotrophic factor (Bdnf), Garek R R, et al. (1998) Laryngoscope 108:671–678; Neu-rotrophin 3 (Ntf3), Garek R R, et al. (1998) Laryngoscope 168:671–678; Myoglobin (Mb); Garry D J, et al. (1998) Nature 395:905–908; Opioid receptor, mu (Oprm), Gaveriaux-Ruff C, et al. (1998) Proc Natl Acad Sci USA 95:6326–6330; Neuropeptide Y (Npy), Hollopeter G, et al. (1998) Int J Obes Relat Metab Disord 22:506–512; Procollagen, type 1, alpha 1 (Cola1) Hormuzdi S G, et al. (1998) Mol Cell Biol 18:3368–3375; Centromere autoanti-gen B (Cenpb), Hudson D F, et al. (1998) J Cell Biol 141:309–319; Oculocerebrorenal syndrome of Lowe (ocrl), Janne P A, et al. (1998) J Clin Invest 101:2042–2053; arachidonate 12-lipoxygenase (Alox12) Johnson E N, et al. (1998) Proc Natl Acad Sci USA 95:3100–3105; H19 fetal liver mRNA (H19), Jones B K, et al. (1998) Genes Dev 12:2200–2207; Hepatocyte nuclear factor 3 gamma (winged helix transcription factor) (Hnf3g), Kaestner K H, et al. (1998) Mol Cell Biol 18:4245–4251; Bone morphogenetic protein 2 (Bmp2)/Bone morphogenetic protein 7 (Bmp7) and Bmp5, Katagiri T, et ad. (1998) Dev Genet 22:340–348; Intercellular adhesion molecule (Icam1), Ley K, et al. (1998) Circ Res 83:287–294; Glutamyl aminopeptidase (Enpep), Lin Q, et al. J Immunol 1998, 160:4681–4687; Prion protein (Prnp), Lipp H P, et al. Behav Brain Res 1998, 95:47–54; RAB3A, member RAS oncogene family (Rab3a), Lonart G, et al. Neuron 1998, 21:1141–1150; Potassium voltage gated channel, shaker related subfamily, member 4 (Kcna4), London B, et al., J Physiol (Lond) 1998, 509:171–182; Apurinic/apyrimidinic endonuclease (Apex), Ludwig D L, et al. Mutat Res 1998, 409:17–29; T-cell receptor gamma, variable 5 (Tcrg-V5), Mallick-Wood C A, et al. Science 1998, 279:1729–1733; Nuclear, factor, erythroid derived 2, like 2 (Nfe212), Martin F, et al. Blood 1998, 91:3459–3466; Inter-leukin 13 (Il13), McKenzie G J, et al. Curr Biol 1998, 8:339–340; Sorbitol dehydrogenase 1 (Sdh1), Ng T, et al. Diabetes 1998, 47:961–966; Guanine nucleotide binding protein, alpha 11 (Gna11), Offermanns S, et al. EMBO J 1998, 17:4304–4312; Estrogen receptor alpha (Estra), Ogawa S, et al. Endocrinology 1998, 139:5070–5081; Inte-grin beta 2 (Itgb2), Intracellular adhesion molecule (Icam1) and CD34 antigen, Oliveira-dos-Santos A J, et al. Eur J Immunol 1998, 28:2882–2892; Angiotensin receptor 1b (Agtr1b), Oliverio M I, et al. Proc Natl Acad Sci USA 1998, 95:15496–15501; Complement factor B (factor B), Pekna M, et al. Scand J Immunol 1998, 47:375–380; Centromere autoantigen B (Cenpb), Perez-Castro A V, et al. Dev Biol 1998,201:135–143; Procollagen, type V, alpha 2 (Col5a2)/Fibrillin 1 (Fbn1), Phelps R G, et al. Mol Med 1998, 4:356–360; Plasminigen activator inhibitor, type 1 (Planh1), Pinsky D J, et al. J Clin Invest 1998, 102:919–928, Carme-liet P, et al. J Clin Invest 1993, 92:2756–2760; Placentae and embryos oncofetal gene (Pem), Pitman J L, et al. Dev Biol 1998, 202:196–214; Postmeiotic segregation increased 1 (*S. cerevisiae*) (Pms1), Prolla T A, et al. Nat Genet 1998, 18:276–278; Prion protein, structural locus (Prn-p), Prusiner S B, et al. Proc Natl Acad Sci USA 1998, 90:10608–10612, Lledo P-M, et al. Proc Natl Acad Sci USA 1996, 93:2403–2407, Sailer A, et al. Cell 1994, 77:967–968, Weissmann C, et al. Philos Trans R Soc Lond [Biol] 1994, 343:431–433, Bueler H, et al. Cell 1993, 73:1337–1347, Weissmann C, et al. Intervirology 1993, 35:164–175; NAD (P)H:quinone oxidoreductase, Radjendirane V, et al. J Biol Chem 1998, 273:7382–7389; Alpha tropomyosin (Tpm1), Rethinasamy P, et al. Circ Res 1998, 82:116–123; Goosecoid and Goosecoid-like (Gscl), Wakamiya M, et al. Hum Mol Genet 1998, 7:1835–1840, Saint-Pore B, et al. Hum Mol Genet 1998, 7:1841–1849; Schlafen 1 (Slfn1); Schwarz D A, et al. Immunity 1998, 9:657–668; Nuclear factor, erythroid derived 2, ubiquitous (Mafk), Shavit J A, et al. Genes Dev 1998, 12:2164–2174; Microphthalmia-associated transcrip-tion factor (Mitf), Smith S B, et al. Exp Eye Res 1998, 66:403–410; Bone morphogenetic protein 6 (Bmp6), Sollo-way M J, et al. Dev Genet 1998,22:321–339; Phosphatidyli-nositol glycan, class A (Piga), Takahama Y, et al. Eur J Immunol 1998, 28:2159–2166; Paired-related homeobox 2 (Prx2), Berge D, et al. Development 1998, 125:3831–3842; Prostaglandin E receptor EP1 subtype (Ptgerep1), Ushikubi F, et al. Nature 1998, 395:281–284; Inmmunoglobulin kappa chain complex (Igk), van der Stoep N, et al. Immunity 1998, 8:743–750; Adenine phosphoribosyl transferase (Aprt), Van Sloun P P, et al. Nucleic Acids Res 1998, 26:4888–4894; Microtubule associated protein 4 (Mtap4), Voss A K, et al. Dev Dyn 1998, 212:258–266; 3-hydroxy-3-methylglutaryl-coenzyme A lyase (Hmgcl), Wang S P, et al. Hum Mol Genet 1998, 7:2057–2062; Fibroblast growth factor receptor 4 (Fgfr4), Weinstein M, et al. Development 1998, 125:3615–3623; Hepsin (Hpn), Wu Q, et al. J Clin Invest 1998, 101:321–326; Small inducible cytokine A11 (Scya11), Yang T, et al. Blood 1998, 92:3912–3923; Small nuclear ribonucleoprotein N (Snrpn), Yang T, et al. Nat Genet 1998, 19:25–31; DNA fragmentation factor, alpha subunit (Dffa), Zhang J, et al. Proc Natl Acad Sci USA 1998, 95:12480–12485; Early growth response 1 (Egr1), Zheng D, et al. Neuroscience 1998, 83:251–258; Early growth response 1 (Egr1)/Hormone receptor (Hmr), Zheng D, et al. Neuroscience 1998, 83:251–258; Hemochromatosis (Hfe), Zhou X Y, et al. Proc Natl Acad Sci.USA 1998, 95:2492–2497; Alpha tropomyosin (Tpm1), Blanchard E M, et al. Circ Res 1997, 81:1005–1010; tRNA phosphoserine (Trsp), Bosl M R, et al. Proc Natl Acad Sci USA 1997, 94:5531–5534; Angiotensin receptor 1b (Agtr1b), Chen X, et al. Am J Physiol 1997, 272:F299–F304; Xeroderma pigmentosum, complementation group C (Xpc), Cheo D L, et al. Mut Res 1997, 374:1–9; B cell leukemia/lymphoma 6

(Bcl6), Dent A L, et al. Science 1997, 276:589–592; Fumarylacetoacetate hydrolase (Fah)/4-hydroxyphenylpyruvic acid dioxygenase (Hpd), Endo F, et al. J Biol Chem 1997, 272:24426–24432; N-methylpurine-DNA glycosylase (Mpg), Engelward B P, et al. Proc Natl Acad Sci USA 1997, 94:13087–13092; Interleukin 1 receptor, type 1 (Il1r1), Glaccum M B, et al. J Immunol 1997, 159:3364–3371; N-methylpurine-DNA glycosylase (Mpg), Hang B, et al. Proc Natl Acad Sci USA 1997, 94:12869–12874; Gamma-aminobutyric acid (GABA-A) receptor, subunit alpha 6 (Gabra6), Homanics G E, et al. Mol Pharmacol 1997, 51:588–596; Superoxide dismutase 2, mitochondrial (Sod2), Huang T T, et al. Arch Biochem Biophys 1997, 344:424–132; Interleukin 11 receptor, alpha chain 1 (Il11ra1), Nandurjar H H, et al. Blood 1997, 90:2148–2159; Alkaline phosphatase 5 (Akp5), Narisawa S, et al. Dev Dyn 1997, 208:432–446; GATA-binding protein 4 (Gata4), Narita N, et al. Development 1997, 124:3755–3764; Lymphocyte protein tyrosine kinase (Lck)/Fyn protooncogene (Fyn); Page S T, et al. Eur J Immunol 1997, 27:554–562; P glycoprotein 3 (Pgy3), Schinkel A H, et al. Proc Natl Acad Sci USA 1997, 94:4028–4033; P glycoprotein 1 (Pgy1)/P glycoprotein 3 (Pgy3), Schinkel A H, et al., Proc Natl Acad Sci USA 1997, 94;4028–4033; Creatine kinase, mitochondrial 1, ubiquitous (Ckmt1), Steeghs K, et al. J Neurosci Methods 1997, 71:29–41; T cell receptor gamma, variable 4 (Tcrg-V4), Sunaga S, et al. J Immunol 1997, 158:4223–4228; Ia-associated invariant chain (p31 form) (Ii), Takaesu N T, et al. J Immunol 1997, 158:187–199; Solute carrier family 18 (vesicular monoamine), member 2 (Slc18a2), Takahashi N, et al. Proc Natl Acad Sci USA 1997, 94:9938–9943; Matrix metalloproteinase 7 (Mmp7), Wilson C L, et al. Proc Natl Acad Sci USA 1997, 94:1402–1407; Formin (Fmn),Wynshaw-Boris A, et al. Mol Med 1997, 3:372–384; Sypnaptophysin (Syp), Arrandale J M, et al. J Biol Chem 1996, 271:21353–21358; Transformation related protein 53 (Trp53), Boehme S A, et al. J Immunol 1996, 156:4075–4078; Neuronal nitric oxide synthase (Nos1), Burnett A L, et al. Mol Medicine 1996, 2:288–296; Eph receptor A2 (Epha2), Chen J, et al. Oncogene 1996, 12:979–988; Urokinase plasminogen activator receptor (Plaur); Dewerchin M, et al. J Clin Invest 1996, 97:870–878; Growth differentiation factor 9 (Gdf9), Dong J, et al. Nature 1996, 383:531–535; Externally regulated phosphatase (Ptpn16), Dorfman K, et al. Oncogene 1996, 13:925–931; Tenascin C (Tnc), Forsberg E, et al. Proc Natl Acad Sci USA 1996, 93:6594–6599; Integrin alpha 1 (Itga1), Gardner H, et al. Dev Biol 1996, 175:301–313; FBJ osteosarcoma oncogene B (Fosb), Gruda M C, et al. Oncogene 1996, 12:2177–2185; Breast cancer 1 (Brca1), Hakem R, et al. Cell 1996, 85:1009–1023; Megakaryocyte-associated tyrosine kinase (Matk), Hamaguchi I, et al. Biochem Biophys Res Commun 1996, 224:172–179; Apolipoprotein B editing complex 1 (Apobec1), Hirano K-I, et al. J Biol Chem 1996, 271:9887–9890; Carboxyl ester lipase, Howles P N, et al. J. Biol. Chem. 1996, 271:7196–7202; Nuclear factor, erythroid derived 2, ubiquitous (Nfe2u), Kotkow K J, Orkin S H, Proc Natl Acad Sci USA 1996, 93:3514–3518; Retinoid X receptor gamma (Rxrg), Krezel W, et al. Proc Natl Acad Sci USA 1996, 93:9010–9014; Early growth response 1 (Egr1), Lee S L, et al. Mol Cell Biol 1996, 16:4566–4572; Adrenergic receptor, alpha 2b (Adra2b), Link R E, et al. Science 1996, 273:803–805; Angiotensin receptor 1a (Agtr1a), Matsusaka T, et al. J Clini Invest 1996, 98:1867–1877; Interleukin 3 receptor, beta chain 1 (Il3rb2), Nicola N A, et al. Blood 1996, 87:2665–2674; Transformation related protein 53 (Trp53), Ohashi M, et al. Jpn J Cancer Res 1996, 87:696–701; Leukemia-associated gene (Lag), Schubart U K, et al. J Biol Chem 1996, 271:14062–14066; Glutathione peroxidase 1 (Gpx1), Spector A, et al. Exp Eye Res 1996, 62:521–540; Arachidonate 12-lipoxygenase, leukocyte (Alox12l), Sun D, Funk C D. J Biol Chem 1996,271:24055–24062; Complement component 3 (C3), Sylvestre D, et al. J Exp Med 1996, 184:2385–2392; CD30 antigen (Cd30), Texido G, et al. Eur J Immunol 1996, 26:19661969; Fc receptor, IgE, low affinity II, alpha polypeptide (Fcer2a), Immunoglobulin heavy chain 5 (delta-like heavy chain) (Igh-5), Interleukin 4 (IL4) and Terminal-deoxynucleotidyl transferase, Texido G, et al. Eur J Immunol 1996, 26:1966–1969; Apolipoprotein A-II (Apoa2), Weng W, Breslow J L, Proc Natl Acad Sci USA 1996, 93: 14788–14794; Amyloid beta (A4) precursor protein (App), Zheng H, et al. Ann N Y Acad Sci 1996, 777:421–426; cAMP responsive element binding protein 1 (Creb1), Blendy J A, et al. Brain Res 1995, 681:8–14; Bradykinin receptor, beta 2 (Bdkrb2), Borkowski J A, et al. J Biol Chem 1995, 270:13706–13710; Growth factor response protein (Gfrp), Crawford P A, et al. Mol Cell Biol 1995, 15:4331–4336; Ciliary neurotrophic factor (Cntf), de Chiara T M, et al. Cell 1995, 83:313–322; Cyclin dependent kinase inhibitor 1A (P21) (Cdkn1a); Deng C, et al. Cell 1995, 82:675–684; Granzyme A (Gzma), Ebnet K, et al. EMBO J 1995, 14:4230–4239; Very low density lipoprotein receptor (Vldlr), Frykman P K, et al. Proc Natl Acad Sci USA 1995, 92:8453–8457; Apolipoprotein E (Apoe)/Apolipoprotein A-I (Apoa1), Goodrum J F, et al. J Neurobiol 1995, 64:408–416; Nitric oxide synthase 1, neuronal (Nos1), Ichinose F, et al. Anesthesiology 1995, 83:101–108; Nitric oxide synthase 2, inducible, macrophage (Nos2), Laubach V E, et al. Proc Natl Acad Sci USA 1995, 92:10688–10692; Peroxisome proliferator activated receptor alpha (Ppara), Lee S S-T, et al. Mol Cell Biol 1995, 15:3012–3022; Growth factor response protein (Gfrp), Lee S L, et al. Science 1995, 269:532–535; H19 fetal liver mRNA (H19)/Insulin-like growth factor 2 (Igf2), Leighton P A, et al. Nature 1995, 375:34–39; Retinoic acid receptor beta (RAR-beta), Luo J, et al. Mech Dev 1995, 53:61–71; Metallothionein 1 (Mt1)/Metallothionein 2 (Mt2), Philcox J C, et al. Biochem J 1995, 308:543–546; Heme oxygenase (decycling) 2 (Hmox2), Poss K D, et al. Neuron 1995, 15:867–873; H1-0 histone (H1fv), Sirotkin A M, et al. Proc Natl Acad Sci USA 1995, 92:6434–6438; Creatine kinase, mitochondrial 1, ubiquitous (Ckmt1), Steeghs K. et al. Biochim Biophys Acta 1995, 1230:130–138; Tenascin C (Tnc), Steindler D A, et al. J Neurosci 1995, 15:1971–1983; Ia-associated invariant chain (Ii), Takaesu N T, et al. Immunity 1995, 3:385–396; Neuroblastoma ras oncogene (Nras), Umanoff H, et al. Proc Natl Acad Sci USA 1995, 92:1709–1713; Receptor-associated protein of the synapse, 43 kDa (Rapsn), Willnow T E, et al. Proc Natl Acad Sci USA 1995, 92:4537–4541; Vitronectin (Vtn), Zheng X, et al. Proc Natl Acad Sci USA 1995, 92:12426–12430; Preproacrosin (Acr), Baba T, et al. J Biol Chem 1994, 269:31845–31849; Vimentin (Vim), Colucci G E, et al. Cell 1994, 79:679–694; Tumor necrosis factor receptor superfamily, member 1b (Tnfrsf1b), Erickson S L, et al. Nature 1994, 372:560–563; Cellular retinoic acid binding protein I (Crabp1), Gorry P, et al. Proc Natl Acad Sci USA 1994, 91:9032–9036; cAMP responsive element binding protein 1 (Creb1), Hummler F, et al. Proc Natl Acad Sci USA 1994, 91:5647–5651; Pore forming protein (Pfp), Kagi D, et al. Nature 1994, 369:31–37; Src-related kinase lacking C-terminal regulatory tyrosine and N-terminal myristylation sit (Srms), Kohmura N, et al. Mol Cell Biol 1994, 14:6915–6925; CD3 polypeptide zeta (Cd3z)/Solute carrier family 22, member 1 (Slc22a1), Koyasu S, et al. EMBO J 1994, 13:784–797; Pore forming protein (Pfp), Lowin B, et al. Proc Natl Acad Sci USA 1994, 91:11571–11575; Retinoic acid receptor, beta (Rarb), Retinoic acid receptor beta2 (RARbeta2), Mendelsohn C, et al. Dev Biol 1994, 166:246–258; Transthyretin (Ttr), Palha J A, et al. J Biol Chem 1994, 269:33135–33139; Procollagen, type X, alpha 1 (Col10a1), Rosati R, et al. Nature Genet 1994, 8:129–135; P glycoprotein 3 (Pgy3), Schinkel A H, et al. Cell 1994, 77:491–502; Yamaguchi sarcoma viral (v-yes) oncogene homolog (Yes), Stein P L, et al. Genes Dev 1994, 8:1999–2007; Fc receptor, IgE, high affinity II, alpha polypeptide (Fcer2a), Stief A, et al. J Immunol 1994, 152:3378–3390; Pore forming protein (Pfp), Walsh C M, et al. Proc Natl Acad Sci USA 1994, 91:10854–10858; CD2 antigen (Cd2), Evans C F, et al. J Immunol 1993, 151:6259–6264; Mannose-6-phosphate receptor, cation dependent (M6pr), Koster A, et al. EMBO J 1993, 12:5219–5223; Retinoic acid receptor, alpha (Rara), Li E, et al. Proc Natl Acad Sci USA 1993, 90:1590–1594, Lufkin T, et al. Proc Natl Acad Sci USA 1993, 90:7225–7229; Retinoic acid receptor, gamma (Rarg), Lohnes D, et al. Cell 1993, 73:643–658; Tumor necrosis factor receptor 1 (TNF-R-1) (Tnfr1), Pfeffer K, et al. Cell 1993, 73:457–467; Lectin, galactose binding, soluble 1 (Lgals1), Poirier F, Robertson E J, Development 1993, 119:1229–1236; Synapsin I (Syn1), Rosahl T W, et al. Cell 1993, 75:661–670; Tumor necrosis factor receptor 1 (Tnfr1), Rothe J, et al. Nature 1993, 364:798–802; Beta-2 microglobulin (B2m), Correa I, et al. Proc Natl Acad Sci USA 1992, 89:653–657; CD2 antigen (Cd2), Killeen N, et al. EMBO J 1992, 11:4329–4336; Apolipoprotein E (Apoe), Piedrahita J A, et al. Proc Natl Acad Sci USA 1992, 89:4471–4475; Myogenic differentiation 1 (Myod1), Rudnicki M A, et al. Cell 1992, 71:383–390; Tenascin C (Tnc), Saga Y, et al. Genes Dev 1992, 6:1821–1831; Beta-2 microglobulin (B2m), Sanjuan N, et al. J Virol 1992, 66:4587–4590; Neuroblastoma myc-related oncogene 1 (Nmyc1), Stanton B R, et al. Genes Dev 1992, 6:2235–2247; and Hemoglobin alpha chain complex (Hba), Popp R A, et al. Genetics 1983, 105:157–167.

Some preferred single-copy, non-essential genes with no phenotypes of the present invention include, but are not limited to, the following: Moesin (Msn), Doi Y., et al., J Biol Chem 1999, 274:2315–2321; Plasminogen activator inhibitor, type II (Planh2) and Planh1; Dougherty K. M., Proc Natl Acad Sci USA 1999, 96:686–691; Nuclear receptor coactivator 1 (Ncoa1), Qi C, et al. (1999) Proc Natl Acad Sci USA 96:1585–1590; Nuclear factor of kappa light chain gene enhancer in B-cells inhibitor, alpha and beta (Nfkbia and Nfkbib), Cheng J D, et al. (1998) J Exp Med 6:1055–1062; H19 fetal liver mRNA (H19), Jones B K, et al. (1998) Genes Dev 12:2200–2207; Prion protein (Prnp), Lipp H P, et al. Behav Brain Res 1998, 95:47–54; Centromere autoantigen B (Cenpb), Perez-Castro A V, et al. Dev Biol 1998, 201;135–143; Placentae and embryos oncofetal gene (Pem), Pitman J L, et al. Dev Biol 1998, 202:196–214; Externally regulated phosphatase (Ptpn16), Dorfman K, et al. Oncogene 1996, 13:925–931; Transformation related protein 53 (Trp53), Ohashi M, et al. Jpn J Cancer Res 1996, 87:696–701; H1-0 histone (H1fv), Sirotkin A M, et al. Proc Natl Acad Sci USA 1995, 92:6434–6438; Creatine kinase, mitochondrial 1, ubiquitous (Ckmt1), Steeghs K, et al. Biochim Biophys Acta 1995, 1230: 130–138; Neuroblastoma ras oncogene (Nras), Umanoff H, et al. Proc Natl Acad Sci USA 1995, 92:1709–1713; Vitronectin (Vtn), Zheng X, et al. Proc Natl Acad Sci USA 1995, 92:12426–12430; Vimentin (Vim), Colucci G E, et al. Cell 1994, 79:679–694; Cellular retinoic acid binding protein I (Crabp1), Gorry P, et al. Proc Natl Acad Sci USA 1994, 91:9032–9036; Retinoic acid receptor beta2 (RARbeta2), Mendelsohn C, et al. Dev Biol 1994, 166:246–258; Retinoic acid receptor, alpha (Rara), Li E, et al. Proc Natl Acad Sci USA 1993, 90: 1590–1594, Lufkin T, et al. Proc Natl Acad Sci USA 1993, 90:7225–7229; Lectin, galactose binding, soluble 1 (Lgals1), Poirier F, Robertson E J, Development 1993, 119:1229–1236; Myogenic differentiation 1 (Myod1), Rudnicki M A, et al. Cell 1992, 71:383–390; and Tenascin C (Tnc), Saga Y, et al. Genes Dev 1992, 6:1821–1831.

In view of the guidance of the present specification, one of ordinary skill in the art can select similar, suitable, single-copy, non-essential genes in mice and other cell types/organisms.

Assembly of Targeting Cassettes

The targeting cassettes described herein can be constructed utilizing methodologies known in the art of molecular biology (see, for example, Ausubel or Maniatis) in view of the teachings of the specification. As described above, the targeting constructs are assembled by inserting, into a suitable vector backbone, polynucleotides encoding a reporter, such as a light-generating protein, e.g., a luciferase gene, operably linked to a promoter of interest; a sequence encoding a positive selection marker; and, optionally a sequence encoding a negative selection marker. In addition, the targeting cassette contains insertion sites such that sequences targeting a single-copy, non-essential gene can be readily inserted to flank the sequence encoding positive selection marker and luciferase-encoding sequence.

A preferred method of obtaining polynucleotides, suitable regulatory sequences (e.g., promoters) is PCR. General procedures for PCR as taught in MacPherson et al., PCR: A PRACTICAL APPROACH, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers are described below in the Examples. After amplification, the resulting fragments can be detected by agarose gel electrophoresis followed by visualization with ethidium bromide staining and ultraviolet illumination.

In one embodiment, PCR can be used to amplify fragments from genomic libraries. Many genomic libraries are commercially available. Alternatively, libraries can be produced by any method known in the art. Preferably, the organism(s) from which the DNA is has no discernible disease or phenotypic effects. This isolated DNA may be obtained from any cell source or body fluid (e.g., ES cells, liver, kidney, blood cells, buccal cells, cerviovaginal cells, epithelial cells from urine, fetal cells, or any cells present in tissue obtained by biopsy, urine, blood, cerebrospinal fluid (CSF), and tissue exudates at the site of infection or inflammation). DNA is extracted from the cells or body fluid using known methods of cell lysis and DNA purification. The purified DNA is then introduced into a suitable expression system, for example a lambda phage.

Another method for obtaining polynucleotides, for example, short, random nucleotide sequences, is by enzymatic digestion. As described below in the Examples, short DNA sequences generated by digestion of DNA from vectors carrying genes encoding luciferase (yellow green or red).

Polynucleotides are inserted into vector genomes using methods known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and, in view of the teachings herein, can be used.

The final constructs can be used immediately (e.g., for introduction into ES cells), or stored frozen (e.g., at −20° C.) until use. Preferably, the constructs are linearized prior to use, for example by digestion with suitable restriction endonucleases.

Transgenic Animals

The targeting constructs containing the luciferase genes are introduced into a pluripotent cell (e.g., ES cell, Robertson, E. J., In: Current Communications in Molecular Biology, Capecchi, M. R. (ed.), Cold Spring Harbor Press, Cold Spring Harbor, N.Y. (1989), pp. 39–44). Suitable ES cells may be derived or isolated from any species or from any strain of a particular species. Although not required, the pluripotent cells are typically derived from the same species as the intended reciepient. ES cells may be obtained from commercial sources, from International Depositories (e.g., the ATCC) or, alternatively, may be obtained as described in Robertson, E. J., supra. Examples of clonally-derived ES cells lines include 129/SVJ ES cells, RW-4 and C57BL/6 ES cells (Genome Systems, Inc.).

ES cells are cultured under suitable conditions, for example, as described in Ausubel et al., section 9.16, supra. Preferably, ES cells are cultured on stomal cells (such as STO cells (especially SNC4 STO cells) and/or primary embryonic fibroblast cells) as described by E. J. Robertson, supra, pp 71–112. Culture media preferably includes leukocyte inhibitory factor ("lif") (Gough, N. M. et al., Reprod. Fertil. Dev. 1:281–288 (1989); Yamamori, Y. et al., Science 246:1412–1416 (1989), which appears to help keep the ES cells from differentiating in culture. Stomal cells transformed with the gene encoding lif can also be used.

The targeting constructs are introduced into the ES cells by any method which will permit the introduced molecule to undergo recombination at its regions of homology, for example, micro-injection, calcium phosphate transformation, or electroporation (Toneguzzo, F. et al., Nucleic Acids Res. 16:5515–5532 (1988); Quillet, A. et al., J. Immunol. 141:17–20 (1988); Machy, P. et al., Proc. Natl. Acad, Sci. (U.S.A.) 85:8027–8031 (1988)). The construct to be inserted into the ES cell must first be in the linear form. Thus, if the knockout construct has been inserted into a vector as described above, linearization is accomplished by digesting the DNA with a suitable restriction endonuclease selected to cut only within the vector sequence and not within the knockout construct sequence. If the ES cells are to be electroporated to insert the construct, the ES cells and construct DNA are exposed to an electric pulse using an electroporation machine and following the manufacturer's guidelines for use. After electroporation, the ES cells are typically allowed to recover under suitable incubation conditions. The cells are then cultured under conventional conditions, as are known in the art, and screened for the presence of the construct.

Screening and selection of those cells into which the targeting construct has been integrated can be achieved using the positive selection marker and/or the negative selection marker in the construct. In preferred embodiments, the construct contains both positive and negative selection markers. In one aspect, methods which rely on expression of the selection marker are used, for example, by adding the appropriate substrate to select only those cells which express the product of the positive selection marker or to eliminate those cells expressing the negative selection marker. For example, where the positive selection marker encodes neomycin resistance, G418 is added to the transformed ES cell culture media at increasing dosages. Similarly, where the negative selection marker is used, a suitable substrate (e.g., gancyclovir if the negative selection marker encodes HSV-TK) is added to the cell culture. Either before or after selection using the appropriate substrate, the presence of the positive and/or negative selection markers in a recipient cell can also be determined by others methods, for example, hybridization, detection of radiolabelled nucleotides, PCR and the like. In preferred embodiments, cells having integrated targeting constructs are first selected by adding the appropriate substrate for the positive and/or negative selection markers. Cells that survive the selection process are then screened by other methods, such as PCR or Southern blotting, for the presence of integrated sequences.

After suitable ES cells containing the construct in the proper location have been identified, the cells can be inserted into an embryo, preferably a blastocyst. The blastocyts are obtained by perfusing the uterus of pregnant females. In one embodiment, the blastocyts are obtained from, for example, the FVB/N strain of mice and the ES cells are obtained from, for example, the C57BL/6 strain of mice. Suitable methods for accomplishing this are known to the skilled artisan, and are set forth by, e.g., Bradley et al:, (1992) Biotechnology, 10:534–539. Insertion into the embryo may be accomplished in a variety of ways known to the skilled artisan, however a preferred method is by microinjection. For microinjection, about 10–30 ES cells are collected into a micropipet and injected into embryos that are at the proper stage of development to permit integration of the foreign ES cell containing the construct into the developing embryo. The suitable stage of development for the embryo used for insertion of ES cells is species dependent, in mice it is about 3.5 days.

While any embryo of the right stage of development is suitable for use, it is preferred that blastocysts are used. In addition, preferred blastocysts are male and, furthermore, preferably have genes encoding a coat color that is different from that encoded by the genes ES cells. In this way, the offspring can be screened easily for the presence of the knockout construct by looking for mosaic coat color (indicating that the ES cell was incorporated into the developing embryo). Thus, for example, if the ES cell line carries the genes for black fur, the blastocyst selected will carry genes for white or brown fur.

After the ES cell has been introduced into the blastocyst, the blastocyst is typically implanted into the uterus of a pseudopregnant foster mother for gestation. Pseudopregnant females are prepared by mating with vasectomized males of the same species and successful implantation usually must occur within about 2–3 days of mating.

Offspring are screened initially for mosaic coat color where the coat color selection strategy has been employed. Southern blots and/or PCR may also be used to determine the presence of the sequences of interest. Mosaic (chimeric) offspring are then bred to each other to generate homozygous animals. Homozygotes and heterozygotes may be identified by Southern blotting of equivalent amounts of genomic DNA from mice that are the product of this cross, as well as nice that are known heterozygotes and wild type mice. Alternatively, Northern blots can be used to probe the mRNA to identify the presence or absence of transcripts encoding either the replaced gene, the luciferase gene, or both. In addition, Western blots can be used to assess the level of expression of the luciferase protein with an antibody against the luciferase gene product. Finally, in situ analysis (such as fixing the cells and labeling with antibody) and/or FACS (fluorescence activated cell sorting) analysis of various cells from the offspring can be conducted using suitable (e.g., anti-luciferase) antibodies to look for the presence or absence of the targeting construct.

In one embodiment of the present invention, the animals are from the C57BL/6 mouse strain. This strain develops a variety of tumors and has been used to develop a number of tumor cells lines, for example, B16 melanoma cells (including, B16F10, B16D5, and B16F1), Lewis lung carcinoma cells (including, LLC, LLC-h59), T241 mouse fibrosarcoma cells, RM-1 and pTC2 mouse prostate cancer cells, and MCA207 mouse sarcoma cells. These cell lines have been extensively used for in vivo tumor biology studies after injection into C57BL/6 mice. The generated targeted transgenic mice in the Examples are in C57BL/6 genetic background and these animals are suitable for injection or implantation of such tumor cells, as well as other tumor cells described in literature that are immunocompatent for C57BL/6 mice. Thus, the transgenic animals can then be used, for example, to monitor, in vivo, tumor progression (e.g., growth) and the efficacy of therapies on tumor regression. For example, where the transgenic animal is tumor-susceptible, it is k 15 monitored for expression of a reporter, e.g., luciferase, which is indicative of tumorigenesis and/or angiogenesis. The monitoring of expression of luciferase reporter expression cassettes using non-invasive whole animal imaging has been described (Contag, C. et al, U.S. Pat. No. 5,650,135, Jul. 22, 1997, herein incorporated by reference; Contag, P., et al, *Nature Medicine* 4(2):245–247, 1998; Contag, C., et al, *OSA TOPS on Biomedical Optical Spectroscopy and Diagnostics* 3:220–224, 1996; Contag, C. H., et al, *Photochemistry and Photobiology* 66(4):523–531, 1997; Contag, C. H., et al, *Molecular Microbiology* 18(4):593–603, 1995). Such imaging typically uses at least one photo detector device element, for example, a charge-coupled device (CCD) camera.

The transgenic animals described herein can also be used to determine the effect of an analyte (e.g., therapy), for example on tumor progression where the promoter induces luciferase expression when a tumor develops. Methods of administration of the analyte include, but are not limited to, injection (subcutaneously, epidermally, intradermally), intramucosal (such as nasal, rectal and vaginal), intraperitoneal, intravenous, oral or intramuscular. Other modes of administration include oral and pulmonary administration, suppositories, and transdermal applications. Dosage treatment may be a single dose schedule or a multiple dose schedule. For example, the analyte of interest can be administered over a range of concentration to determine a dose/response curve. The analyte may be administered to a series of test animals or to a single test animal (given that response to the analyte can be cleared from the transgenic animal).

VEGF and VEGFR Genes

In one aspect the present invention relates to the isolation and characterization of the mouse VEGFR-2 gene promoter. This section describes some information related to the VEFG and VEGFR gene families. Alternative names for some of these genes are as follows: VEGF (vascular endothelial growth factor) is also named VPF (vascular permeability factor); VEGFR-1 is also named FLT1; VEGFR-2 is also named KDR/FLK1; and VEGFR-3 is also named FLT4.

VEGF is a homodimeric 45 kDa (monomer 23 kDa) protein. VEGF has five isoforms of which VEGF165 and VEGF121 are the most abundant. Both are ligands for VEGFR-2 as well as VEGFR-1 (Soker, S., et al., JBC 271:5761–67, 1996). VEGF165 is the only VEGF isoform that binds to Neuropillin-1 (Soker, S., et al., Cell 92:735–745, 1998). VEGF is extremely unstable—its half life in circulation is only 3 minutes (Ferrara, N., et al., Nature 380:439–442, 1996; Ferrara, N., et al., Endocr Rev 18:4–25, 1997).

VEGF-B is 43% (aa) identical to VEGF and exists as homodimers. It can also form heterodimers with VEGF (Olofsson, B., et al., Proc Natl Acad Sci USA 93:2576–81, 1996). VEGF-B is a ligand for VEGFR-1 (Olofsson, B., et al., Proc Natl Acad Sci USA 95:11709–14, 1998).

VEGF-C is 30% (aa) identical to VEGF. The mature VEGF-C is 23 kDa, the precursor protein is 35.8 kDa VEGF-C is a ligand for VEGFR-3 as well as VEGFR-2. It induces autophosphorylation of both receptors (Joukov, V., et al., EMBO J 15:290–298, 1996).

VEGF-D is 31% (aa) identical to VEGF165 and 48% (aa) identical to VEGF-B. The mature VEGF-D is approximately 22 KDa. VEGF-D is a ligand for VEGFR-3 as well as VEGFR-2. It induces autophosphorylation of both receptors (Achen, M. G., et al., 1998 Proc Natl Acad Sci USA 95:548–53, 1998).

PIGF is 46% identical (aa) to VEGF (Maglione, D., et al., Proc Natl Acad Sci 88:9267–71, 1991) and can form heterodimers with VEGF ((Disalvo, J., et al., JBC 270:7717–23, 1995).

VEGFR-1 is an approximately 180 KDa tyrosine kinase receptor for VEGF-B (Olofsson, B., et al., Proc Natl Acad Sci USA 95:11709–14, 1998) and VEGF (de Vries, C., et al., Science 255:989–91, 1992) and PIGF (Park, J. E., et al., J Biol Chem 269:25646–54, 1994).

VEGFR-2 is an approximately 200 KDa tyrosine kinase receptor for VEGF (Terman, B. I., et al., Oncogene September 6(9):1677–83, 1991), VEGF-C (Joukov, V., et al., EMBO J 15:290–298, 1996), and VEGF-D (Achen, M. G., et al., 1998 Proc Natl Acad Sci USA 95:548–53, 1998).

VEGFR-3 is a tyrosine kinase receptor (Pajusola, K., et al., Cancer Res 52:5738–43, 1992) on lymphatic EC for VEGF-C (Dumont, D. J., et al., Science 282:946–949, 1998) and VEGF-D (Achen, M. G., et al., 1998 Proc Natl Acad Sci USA 95:548–53, 1998). VEGFR-3 has a processed mature form of about 125 kDa, and an unprocessed form of about 195 kDa (Achen, M. G., et al., 1998 Proc Natl Acad Sci USA 95:548–53, 1998).

Neuropillin-1 is an approximately 130 KDa receptor tyrosine kinase. It binds VEGF165, but not VEGF121 (Soker, S., et al., Cell 92:735–745, 1998).

Expression of many of these genes has been evaluated in adults. A summary of information relating to expression follows here.

VEGF has an approximately 3.7 kb transcript. It is expressed in multiple human tissues, including heart, skeletal muscle and prostate. In mouse, VEGF is mainly expressed in heart, lung and kidney. The rest of the human or mouse tissues, including brain and testis, do not express detectable or significant level of VEGF (Olofsson, B., et al., Proc Natl Acad Sci USA 93:2576–81, 1996). In another study, it was shown that VEGF is highly expressed in epithelial cells of lung alveoli, renal glomeruli and adrenal cortex and in cardiac myocytes (Berse, B., MCB 3:211–20, 1992).

VEGF-B has an approximately 1.4 kb transcript. It is expressed in a majority of human and mouse tissues. In human, VEGF-B is most prominently expressed in heart, skeletal muscle, pancreas, brain and prostate. In mouse, VEGF-B is mostly expressed heart, skeletal muscle, brain and kidney. Liver does not appear to express a significant level of VEGF-B in either humans or mice. VEGF-B and VEGF are co-expressed in many human tissues, such as heart, skeletal muscle, pancreas and prostate. In general, VEGF-B is more abundantly expressed than VEGF. VEGF-B can act as an endothelial cell growth factor (Olofsson, B., et al., Proc Natl Acad Sci USA 93:2576–81, 1996).

VEGF-C has an approximately 2.4 kb transcript that is expressed in multiple human tissues, most prominently in heart, skeletal muscle, placenta, ovary, small intestine, pancreas and prostate. Several tissues, including brain and liver, do not appear to express detectable levels of VEGF-C (Joukov, V., et al., EMBO J 15:290–298, 1996).

VEGF-D has an approximately 2.3 kb transcript that is expressed in multiple human tissues, most prominently in heart, skeletal muscle, lung, colon and small intestine. Several tissues, including brain, liver, placenta, do not appear to express detectable levels of VEGF-D (Achen, M. G., et al., 1998 Proc Natl Acad Sci USA 95:548–53, 1998).

VEGFR-1 appears to be endothelial cell specific (Peters, K. G., et al., Proc Natl Acad Sci 90:8915–19, 1993). VEGFR-1 cDNA is approximately 7.7 kb and encodes a protein of 1338 aa. It was expressed in a variety of normal tissues of adult rat (Shibuya, M., et al., Oncogene 5:519–24, 1990). In a glioma model of tumor angiogenesis, both VEGFR-1 and VEGFR-2 are specifically expressed in Ecs that have penetrated into the tumor, but are absent from Ecs in the normal brain tissues. VEGF expression was detectable in glioma cells along necrotic edge (Plate, K. H., et al., Cancer Research 53:5822–27, 1993).

VEGFR-2 is expressed as an approximately 7 kb transcript (Terman, B. I., et al., Oncogene September 6(9): 1677–83, 1991) that appears to be endothelial cell specific. VEGFR-2 is expressed ubiquitously in many tissues, including heart, placenta, lung and kidney. The expression levels of VEGFR-2 are relatively low in these tissues compared with neuropillin expression. Brain does not appear to express detectable levels of VEGFR-2 (Soker, S., et al., Cell 92:735–745, 1998). In situ hybridization analysis revealed a specific association of VEGFR-2 with endothelial cells at all stages of mouse development. It is abundant in proliferating endothelial cells of vascular sprouts and branching vessels of embryonic and early postnatal brain, but were drastically reduced in adult brain, where proliferation has ceased (Millauer, B., Cell 72:835–46, 1993).

VEGFR-3 is expressed as approximately 5.8 kb and 4.5 kb mRNAs. Most fetal tissues expressed VEGFR-3, with spleen, brain intermediate zone, and lung showing the highest levels. It does not appear to be expressed in the endothelial cells of blood vessels (Pajusola K., et al., Cancer Res 52:5738–43, 1992). During embryonic development, VEGFR-3 is expressed in blood vessels but become largely restricted to the lymphatic endothelium postnatally (Kaipainen, A., et al., Proc Natl Acad Sci USA 92: 3566–3570, 1995).

Neuropillin-1 is expressed in both endothelial cells and many types of tumor cells as an approximately 7 kb transcript. Most tissues express high level of Neuropillin-1, especially in heart and placenta; Skeletal muscle, pancreas, lung and kidney also express high level of Neuropillin-1. Brain does not appear to express detectable levels of Neuropillin-1 (Soker, S., et al., Cell 92:735–745, 1998).

Some functions of these genes have been evaluated and are as follows.

VEGF is a specific mitogen for EC in vitro and a potent angiogenic factor in vivo. In vitro, VEGF binds and induces autophosphorylation of VEGFR-2 and VEGFR-1, but the mitogenic response is mediated only through VEGFR-2 (Waltenberger, J., JBC 269:26988–95, 1994). VEGF functions as a survival factor for newly formed vessels during developmental neovascularization, possibly through mediating interaction of endothelial cells with underlying matrix, but is not required for maintenance of mature vessels (Benjamin, L. E., et al., Proc Natl Acad Sci 94:8761–66, 1997). In embryogenesis, VEGF and VEGFR-2 interaction induces the birth and proliferation of endothelials (Hanahan, D., Science 277:48–50, 1997). Binding of VEGF to VEGFR-1 elicits endothelial cell-cell interactions and capillary tube formation, a process that follows closely proliferation and migration of endothelial cells (Hanahan, D., Science 277:48–50, 1997). In a tumorigenesis study, it was shown that VEGF is critical for the initial s.c. growth of T-47D breast carcinoma cells transplanted into nude mice, whereas other angiogenic factors such as bFGF can compensate for the loss of VEGF after the tumors have reached a certain size (Yoshiji, H., et al., Cancer Research 57:3924–28, 1997). VEGF is a major mediator of aberrant endothelial cells (EC) proliferation and vascular permeability in a variety of human pathologic situation, such as tumor angiogenesis, diabetic retinopathy and rheumatoid arthritis (Benjamin, L. E., et al., Proc Natl Acad Sci 94:8761–66, 1997, Soker, S., et al., Cell 92:735–745, 1998). VEGF induces expression of plasminogen activator (PA), PA inhibitor 1 (PAI-1), MMP, and interstitial collagenase in EC. These findings are consistent with the proangiogenic activities of VEGF. VEGF promotes expression of VCAM-1 and ICAM-1 in EC, thus may facilitate the adhesion of activated NK cells to EC. VEGF may promote monocyte chemotaxis (Pepper, M. S., et al., BBRC 181:902–906, 1991; Ferrara, N., et al., Endocr Rev 18:4–25, 1997). Tumors are believed to be the principal source of VEGF. A correlation has been observed between VEGF expression and vessel density in human breast tumors, renal cell carcinoma and colon cancer (Fong, T. A. T., et al., Cancer Res 59:99–106, 1999). VEGF and PGF expressions were significantly upregulated in 96% and 91% of hypervascular renal carcinoma tissues compared with adjacent normal kidney tissues (Takahashi, A., et al., Cancer Res 54:4233–7, 1994).

VEGF-B is a mitogen for EC and may be involved in angiogenesis in muscle and heart (Olofsson, B., et al., Proc Natl Acad Sci USA 93:2576–81, 1996). In vitro, binding of VEGF-B to its receptor VEGFR-1 leads to increased expression and activity of urokinase-type plasminogen activator and plasminogen activator inhibitor, suggesting a role for VEGF-B in the regulation of extracellular matrix degradation, cell adhesion, and migration (Olofsson, B., et al., Proc Natl Acad Sci USA 95:11709–14, 1998).

VEGF-C may regulate angiogenesis of lymphatic vasculature, as suggested by the pattern of VEGF-C expression in mouse embryos (Kukk, E., et al., Development 122:3829–37, 1996). Although VEGF-C is also a ligand for VEGFR-2, the functional significance of this potential interaction is unknown. Overexpression of VEGF-C in the skin of transgenic mice resulted in lymphatic, but not vascular, endothelial proliferation and vessel enlargement, suggesting the major function of VEGF-C is through VEGFR-3 rather than VEGFR-2 (Jeltsch, M., et al., Science 276:1423–5, 1997). Using the CAM assay, VEGF and VEGF-C were shown to be specific angiogenic and lymphangiogenic growth factors, respectively (Oh, S. J., et al., Del Biol 188:96–109, 1997).

VEGF-D is a mitogen for EC. VEGF-D can also activate VEGFR-3. It is possible that VEGF-D could be involved in the regulation of growth and/or differentiation of lymphatic endothelium (Achen, M. G., et al., 1998 Proc Natl Acad Sci USA 95:548–53, 1998).

PlGF can potentiate the action of low concentrations of VEGF in vitro and in vivo (Park, J. E., et al., J Biol Chem 269:25646–54,1994).

VEGFR-1 signaling pathway may regulate normal endothelial cell-cell or cell-matrix interactions during vascular development, as suggested by a knockout study (Fong, G. H., et al., Nature 376:65–69, 1995). Although VEGFR-1 has a higher affinity to VEGF than VEGFR-2, it does not transduce the mitogenic signals of VEGF in ECs (Soker, S., et al., Cell 92:735–745, 1998).

VEGFR-2 appears to be the major transducer of VEGF signals in EC that result in chemotaxis, mitogenicity and gross morphological changes in target cells (Soker, S., et al., Cell 92:735–745. 1998).

VEGFR-3 has an essential role in the development of the embryonic cardiovascular system before the emergence of lymphatic vessels, as shown by a knockout study (Dumont, D. J., et al., Science 282:946–949, 1998).

Neuropillin-1 is a receptor for VEGF165. It can enhance the binding of VEGF165 to VEGFR-2 and VEGF165 mediated chemotaxis (Soker, S., et al., Cell 92:735–745, 1998).

Gene regulation of some of these genes has been investigated and is discussed herein below.

In situ hybridization demonstrated VEGF mRNA was present in transplanted tumor cells but not in tumor blood vessels, indicating that immunohistochemical labeling of tumor vessels with VEGF antibodies reflects uptake of VEGF, not endogenous synthesis. VEGF protein staining was evident in adjacent preexisting venules and small veins as early as 5 hours after tumor transplant and plateaued at maximally intense levels in newly induced tumor vessels by approximately 5 days. In contrast, vessels more than approximately 0.5 mm distant from tumors were not hyperpermeable and did not exhibit immunohistochemical staining for VEGF. Vessel staining disappeared within 24–48 h of tumor rejection. These studies indicate that VEGF is synthesized by tumor cells in vivo and accumulates in nearby blood vessels. Because leaky tumor vessels initiate a cascade of events, which include plasma extravasation and which lead ultimately to angiogenesis and tumor stroma formation, VEGF plays a pivotal role in promoting tumor growth (Dvorak, H. F., et al., J Exp Med 174:1275–8, 1991). In addition, it was shown that stromal cells can be stimulated by transplanted tumor cells for VEGF production (Fukumura, D., et al., Cell, 94:715–25, 1998). Fibroblasts cultured in vitro are highly activating for VEGF promoter function compared with fibroblasts in freshly isolated tumors, indicating the culture condition did not mimic the status of normal (unactivated) tissue in vivo (Fukumura, D., et al., Cell, 94:715–25, 1998). For example, C6 tumor spheroids (C6 is a cell line derived from a rat glial tumor— C6 cells aggregate and form small spheroids in culture) implanted into nude mice became neovascularized accompanied by a gradual reduction of VEGF expression (Shweiki, D., et al., Proc Natl Acad Sci 92:768–772, 1995). The VEGF promoter region bears many of the characteristics of a house-keeping gene (Tischer, E., JBC 266:11947–11954, 1991), hence it is likely that almost any cell type could serve as a source for VEGF upon hypoxic or ischemic demand (Fukumura, D., et al., Cell, 94:715–25, 1998).

VEGF expression was upregulated by hypoxia (Shweiki, D., et al., Nature 359:843–5, 1992), due to both increased transcriptional activation and stability of its mRNA (Ikeda, E., et al., JBC 270:19761–5, 1995). In a number of in vitro studies, it was shown that hypoxia upregulates VEGF expression through the activation of P13K/Akt pathway (Mazure, N. M., et al., Blood 90:3322–31, 1997) and HIF-1 (an enhancer induced by hypoxia and bind to VEGF promoter region) (Forsythe, J. A., MCB 16:4604–13, 1996; Mazure, N. M., et al., Blood 90:3322–31, 1997). VEGF is also upregulated by overexpression of v-Src oncogene (Mukhopadhyay, D., Cancer Res. 15:6161–5, 1995), c-SRC (Mukhopadhyay, D., et al., Nature 375:577–81, 1995), and mutant ras oncogene (Plate, K. H., Nature 359:845–8, 1992). The tumor suppressor p53 downregulates VEGF expression (Mukhopadhyay, D., Cancer Res. 15:6161–5, 1995). A number of cytokines and growth factors, including PGF, TPA (Grugel, S., et al., JBC 270:25915–9, 1995), EGF, TGF-b, IL-1, and IL-6 induce VEGF mRNA expression in certain type of cells (Ferrara, N., et al., Endocr Rev 18:4–25, 1997). Kaposi's sarcoma-associated herpesvirus (KSHV), which encodes a G-protein-coupled receptor—a homolog of IL-8 receptor, can activate JNK/SAPK and p38MAPK and increase VEGF production, thus causing cell transformation and tumorigenicity. (Bais, C., Nature 391:86–9, 1998).

The growth of androgen-dependent Shionogi carcinoma in immunodeficient mice was regressed after the mice were castrated, accompanied by decrease in VEGF expression. Two weeks after castration, a second wave of angiogenesis and tumor growth begins with a concomitant increase in VEGF expression. (Jain, R. K., Proc Natl Acad Sci USA 95:10820–5, 1998).

VEGF-D is induced by transcription factor c-fos in mouse (Orlandini, M. Proc Natl Acad Sci 93:11675–80, 1996).

Overexpression of some of these genes has been evaluated using different systems.

VEGF overexpression in skin of transgenic mice induces angiogenesis, vascularhyperpermeability and accelerated tumor development (Larcher, F., et al., Oncogene 17:303–11, 1998). Retina tissue-specific VEGF overexpression in transgenic mice cause intraretinal and subretinal neovascularization (Okamoto, N., et al., Am J Pathol 151:281–91, 1997). VEGF overexpression mediated by the Tet system promotes tumorigenesis of C6 glioma cells when transplanted into nude mice. The tumors become hypervascularized with abnormally large vessels, arising from excessive fusions. The tumors were less necrotic. After VEGF expression was shut off, regression of the tumors occurred due to detachment of endothelial cells from the walls of preformed vessels and their subsequent apoptosis. Vascular collapse further lead to hemorrhages and extensive tumor necrosis (Benjamin, L. E., et al., Proc Natl Acad Sci 94;8761–66, 1997). In human-VEGF-promoter-GFP transgenic mice, implantation of solid tumor induces specific GFP expression in stromal cells. Transgenic mice were mated with T-antigen mice (able to form spontaneous mammary tumors) to generate double transgenic mice, in which spontaneous mammary tumors were formed. Strong stromal, but not tumor, expression of GFP was observed (Fukumura, D., et al., Cell, 94:715–25, 1998). A CCD camera was used to monitor GFP expression. GFP half life was shown to be between about 1.2–1.5 days (Fukumura, D., et al., Cell, 94:715–25, 1998). The transgene was integrated into the IgG locus of the chromosome through DNA recombination (Fukumura, D., et al., Cell, 94:715–25, 1998). FVB derived VEGF-GFP transgenic mice were mated with wild-type C3H mice to create hybrid mice that can be served as hosts for C3H derived tumor lines (Fukumura, D., et al., Cell, 94:715–25, 1998).

VEGF-C overexpression in the skin of transgenic mice resulted in lymphatic, but not vascular, endothelial proliferation and vessel enlargement (Jeltsch, M., et al., Science 276:1423–5, 1997).

Neuropillin-1 overexpression in transgenic mice resulted in embryonic lethality. The embryos possessed excess capillaries and blood vessels. Dilated vessels and hemorrhage were also observed (Kitsukawa, T., et al., Development 121:4309–18, 1995).

The functions of some of these genes have been evaluated in knock-out mice constructs, animal studies, and in vitro studies.

A VEGF knockout was an embryonic lethal. F1 is also embryonic lethal and angiogenesis was impaired. VEGF secretion from +/− ES cells was reduced to 50% (Carmellet, P., et al., Nature 380:435–439, 1996; Ferrara, N., et al., Nature 380:439–442, 1996).

VEGFR-1 was evaluated in a lacZ knock-in wherein a fragment of the exon that contains ATG start codon was replaced by LacZ. Knockout mice were embryonic lethal. Blood vessels were formed, but the organization of the blood vessel was perturbed (Fong, G. H., et al., Nature 376:65–69, 1995).

VEGFR-2 was an embryonic lethal caused by defective endothelial cell development (Shalaby, F., et al., Nature 376:62–65, 1995).

VEGFR-3(LacZ Knock-in) was an embryonic lethal caused by defective blood vessel development (Dumont, D. J., et al., Science 282:946–949, 1998).

Neuropillin-1 was an embryonic lethal (Dumont, D. J., et al., Science 282:946–949, 1998).

In vitro studies showed that a mutant VEGF (a heterodimer of two mutant VEGF) (Siemeister, G., et al., Proc Natl Acad Sci 95;4625–9, 1998), as well as a GST-Exon7 (VEGF) fusion protein (Soker, S., et al., JBC 272:31582–88, 1997), was able to inhibit endothelial cell proliferation by acting as an VEGF antagonist and interfering VEGF binding to VEGFR-2 and VEGFR-1 (Siemeister, G., et al., Proc Natl Acad Sci 95:4625–9, 1998). More importantly, A VEGF neutralizing chimeric protein, containing the extracellular domain of VEGF receptor (either VEGFR-1 or VEGFR-2) fused with IgG, substantially reduced the development of retinal neovascularization when injected into mice with ischemic retinal disease (Aiello, L. P., et al., Proc Natl Acad Sci 92:10457–61, 1995).

Treatment of tumors with monoclonal antibodies directed against VEGF resulted in dramatic reduction in tumor mass due to the suppression of tumor angiogenesis (Kim, K. J., et al., Nature 362:84144, 1993). Injection of antibodies against VEGF reduced tumor vascular permeability and vessel diameter in immunodeficient mice transplanted with human glioblastoma, colon adenocarcinoma, and melanoma (Yuan, F., et al., Proc Natl Acad Sci 93:14765–70, 1996). Retrovirus mediated overexpression of a dominant negative form of VEGFR-2 in nude mice suppresses the growth of transplanted rat C6 glioma tumor cells (Millauer, B., et al., Nature 367:576–9, 1994) mammary, ovarian tumors and lung carcinoma (Millauer, B., et al., Cancer Res 56:1615–20, 1996).

Mouse VEGFR-2 Promoter

The subject nucleic acids of the present invention (e.g., as described in Example 3) find a wide variety of applications including use as hybridization probes, PCR primers, expression constructs useful for compound screening, detecting the presence of VEGFR-2 genes or varients thereof, detecting the presence of gene transcripts, detecting or amplifying nucleic acids encoding additional VEGFR-2 promoter sequences or homologs thereof (as well as, structural analogs), and in a variety of screening assays.

The present invention provides efficient methods of identifying pharmacological agents or lead compounds for agents active at the level of VEGFR-2 gene transcription. A wide variety of assays for transcriptional regulators can be used based on the teaching of the present specification, including, but not limited to, cell-based transcription assays, screening in vivo in transgenic animals, and promoter-protein binding assays. For example, the disclosed luciferase reporter constructs are used to transfect cells for cell-based transcription assays. For example, primary endothelial cells are plated onto microtiter plates and used to screen libraries of candidate agents for lead compounds which modulate the transcriptional regulation of the VEGFR-2 gene promoter, as monitored by luciferase expression (Example 5).

As noted above, the present invention relates to a recombinant nucleic acid molecule comprising the promoter region of a mouse VEGFR-2 gene. This invention provides a nucleic acid molecule having a sequence selected, for example, from the following groups: (a) a nucleic acid sequence of greater than 80% identity to that of SEQ ID NO:32, or a fragment thereof, exhibiting promoter activity, in particular VEGFR-2 promoter activity; (b) a nucleic acid sequence substantially complementary to said nucleic acid sequence of (a), or a fragment thereof; and (c) a nucleic acid sequence that specifically. hybridizes to said nucleic acid sequences of (a) or (b) or fragments thereof.

The invention includes further VEGFR-2 promoter sequences identified based on the teachings of the present specification (including, but not limited to, sequence information and isolation methods, e.g., Example 3).

This invention also provides novel deletion constructs of the VEGFR-2 promoter which either increase or decrease promoter activity beyond that of the naturally occurring promoter. Such constructs may provide greater sensitivity than the native promoter when used to screen for compounds which affect VEGFR-2 promoter activity.

The nucleic acid molecules of this invention are useful in effecting tissue specific expression in endothelial cells, as well as, for screening for compounds that selectively modulate transcription in endothelial cells and compounds that modulate angiogenic processes.

Those skilled in the art can practice the invention by following the guidance of the specification supplemented with standard procedures of molecular biology for the isolation and characterization of the VEGFR-2 promoters, their transfection into host cells, and vascular endothelial cell-specific expression of heterologous DNA operably linked to said VEGFR-2 promoters. For example, DNA is commonly transferred or introduced into recipient mammal cells by calcium phosphate-mediated gene transfer, electroporation, lipofection, viral infection, and the like. General methods and vectors for gene transfer and expression may be found, for example, in M. Kriegler, Gene Transfer and Expression: A Laboratory Manual, Stockton Press (1990). Direct gene transfer to cells in vivo can be achieved, for example, by the use of modified viral vectors, including, but not limited to, retroviruses, adenoviruses, adeno-associated viruses and herpes viruses, liposomes, and direct injection of DNA into certain cell types. In this manner, recombinant expression vectors and recombinant cells containing the novel VEGFR-2 promoters of the present invention operably linked to desired heterologous gene can be delivered to specific target cells in vivo. See, e.g., Wilson, Nature, 365: 691–692 (1993); Plautz et al, Annals NY Acad. Sci., 716: 144–153 (1994); Farhood et al, Annals NY Acad. Sci., 716: 23–34 (1994) and Hyde et al Nature, 362: 250–255 (1993). Furthermore, cells may be transformed ex vivo and introduced directly at localized sites by injection, e.g., intra-articular, intracutaneous, intramuscular and the like.

Cloning and characterization of the VEGFR-2 promoter are described in Examples 3 and 5, below.

Compound/Drug Screening

Another aspect of this invention is its use in screening for pharmacologically active agents (or compounds) that modulate VEGFR-2 receptor promoter activity either by affecting signal transduction pathways that necessarily precede transcription or by directly affecting transcription of the VEGFR-2 gene.

For screening purposes an appropriate host cell, preferably an endothelial cell, more preferably a vascular endothelial cell, is transformed with an expression vector comprising a reporter gene (e.g., luciferase) operably linked to the VEGFR-2 gene promoter of this invention. The transformed host cell is exposed to various test substances and then analyzed for expression of the reporter gene. This expression can be compared to expression from cells that were not exposed to the test substance. A compound which increases the promoter activity of the VEGFR-2 promoter will result in increased reporter gene expression relative to the control. Similarly, compounds which act as antagonists for the VEGFR-2 promoter signalling pathway will result in decreased reporter gene expression relative to the control.

Thus, one aspect of the invention is to screen for test compounds that regulate the activity of the VEGFR-2 promoter by, for example, (i) contacting a host cell in which the VEGFR-2 promoter disclosed herein is operably linked to a reporter gene with a test medium containing the test compound under conditions which allow for expression of the reporter gene; (ii) measuring the expression of the reporter gene in the presence of the test medium; (iii) contacting the host cell with a control medium which does not contain the test compound but is otherwise essentially identical to the test medium in (i), under conditions essentially identical to those used in (i); (iv) measuring the expression of reporter gene in the presence of the control medium; and (v) relating the difference in expression between (ii) and (iv) to the ability of the test compound to affect the activity of the VEGFR-2 promoter.

Alternatively, the transformed cells may be induced with a transcriptional inducer, such as IL-1 or TNF-alpha, forskolin, dibutyryl-cAMP, or a phorbol-type tumor promoter, e.g., PMA. Transcriptional activity is measured in the presence or absence of a pharmacologic agent of known activity (e.g., a standard compound) or putative activity (e.g., a test compound). A change in the level of expression of the reporter gene in the presence of the test compound is compared to that effected by the standard compound. In this way, the ability of a test compound to affect VEGFR-2 transcription and the relative potencies of the test and standard compounds can be determined.

Thus in a further aspect, the present invention provides methods of measuring the ability of a test compound to modulate VEGFR-2 transcription by: (i) contacting a host cell in which the VEGFR-2 promoter, disclosed herein, is operably linked to a reporter gene with an inducer of VEGFR-2 promoter activity under conditions which allow for expression of the reporter gene; (ii) measuring the expression of the reporter gene in the absence of the test compound; (iii) exposing the host cells to the test compound either prior to, simultaneously with, or after contacting, the host cells with the inducer; (iv) measuring the expression of the reporter gene in the presence of the test compound; and (iv) relating the difference in expression between (ii) and (iv) to the ability of the test compound to modulate VEGFR-2-mediated transcription.

Because different inducers are known to affect different modes of signal transduction, it is possible to identify, with greater specificity, compounds that affect a particular signal transduction pathway. Further, because the VEGF receptors have been shown to be upregulated in tumor cells and this upregulation appears to be necessary for tumor angiogenesis, such assays provide a means of identifying compounds that will inhibit and/or reverse tumor growth by downregulating VEGFR-2 expression and thus preventing or reducing tumor angiogenesis.

A variety of reporter genes may be used in the practice of the present invention. Preferred are those that produce a protein product which is easily measured in a routine assay. Suitable reporter genes include, but are not limited to chloramphenicol acetyl transferase (CAT), light generating proteins (e.g., luciferase), and beta-galactosidase. Convenient assays include, but are not limited to calorimetric, fluorimetric and enzymatic assays. In one aspect, reporter genes may be employed that are expressed within the cell and whose extracellular products are directly measured in the intracellular medium, or in an extract of the intracellular medium of a cultured cell line. This provides advantages over using a reporter gene whose product is secreted, since the rate and efficiency of the secretion introduces additional variables which may complicate interpretation of the assay. In a preferred embodiment, the reporter gene is a light generating protein. When using the light generating reporter proteins described herein, expression can be evaluated accurately and non-invasively as described above (see, for example, Contag, P. R., et al., (1998) Nature Med. 4:245–7; Contag, C. H., et al., (1997) Photochem Photobiol. 66:523–31; Contag, C. H., et al., (1995) Mol Microbiol. 18:593–603).

In another aspect of this invention, transgenic animals expressing a heterologous gene encoding a detectable product under the regulatory control of the VEGFR-2 promoter, as disclosed herein, may be used to determine the effect of a test compound on the stimulation or inhibition of the VEGFR-2 promoter in vivo. The test compound is, for example, administered to the animal and the degree of expression of the heterologous gene observed is compared to the degree of expression in the absence of administration of the test compound using, for example, whole animal luciferase-based assays as disclosed herein. Methods of generating transgenic animals were described above.

This invention also provides transgenic animals useful as disease models for studying VEGFR-2 function and endothelial cell-specific gene expression.

Various forms of the different embodiments of the invention, described herein, may be combined.

The following examples are intended only to illustrate the present invention and should in no way be construed as limiting the subject invention.

EXAMPLES

Example 1

Generating the Targeting Cassette and Vector

A. Creation of the Backbone Vector pTK53: The 0.5 kb mouse phosphoglycerate kinase 1 promoter was amplified with PGK primers (PGKF, SEQ ID NO:1: ATCGAATTCTACCGGGTAGGGGAGGCGCTTT; PGKR, SEQ ID NO:2: GGCTGCAGGTCGAAAGGCCCGGAGATGAGG) using mouse genomic DNA (Genome Systems, Inc., St. Louis, Mo.) as template. This fragment was then double digested with EcoRI and PstI and cloned into the pKS vector (Stratagene, La Jolla, Calif.) which was linearized with the same enzymes. The neomycin gene was amplified with NeoF (SEQ ID NO:3: ACCTGCAGCCAATATGGGATCGGCCATTGAAC) and NeoR (SEQ ID NO:4: GGAT CCGCGGCCGCCCCCAGCTGGTTCTTTCCGCCTC) primers using pNTKV1907 (Stratagene) as a template. The 1.1 kb PCR fragment was double digested with PstI and BamHI and cloned into the pKS-PGK vector which was linearized with the same enzymes. This pKS-PGK-Neo vector was used to clone thymidine kinase gene as follows. Primers TKF (SEQ ID NO: 5: GGATCCTCTAGAGTCGAGCAGTGTGGTTTT) and TKR (SEQ ID NO:6: GAGCTCCCGTAGTCAGGTTYAGTTCGTCCG) were used to amplify the TK gene from pNTKV1907 (Stratagene). The amplified 2 kb fragment was then digested with BamHI and SacI and cloned into pKS-PGK-Neo vector that was linearized with the same enzymes. This constructed vector was designated as pTK. A synthetic linker F5R5 was made after annealing of two primers (forward primer, SEQ ID NO: 7: GTACATTTAAATCCRGCAGG, reverse primers, SEQ ID NO:8: AGCTCCTGCAGGATTTAAAT). This linker was inserted between Asp718I and HindIII sites of pTK and the new construct was designated pTK5. A second synthetic linker F3R3 was made by annealing of two primers (F3R31 forward primer, SEQ ID NO:9: GGC CCGGGCTTAATTAATGCATCATATGGTACCG TTTAAACGCGGCCGCAAGCTTGTCGACGGCGCG CCGGCCGGCC, F3R32 reverse primer, SEQ ID NO: 10: GATCGGCCGGCCGGCGCGCCGTCGACAAGCTTGC GGCCGCGTTTAAACGGTACCATATGATGCATTAATR AAGCCCG).). This linker was inserted between NotI and BamHI sites of pTK and the new construct was designated pTK53. Schematics of the vectors are shown are shown in FIG. 1.

Figure 2:
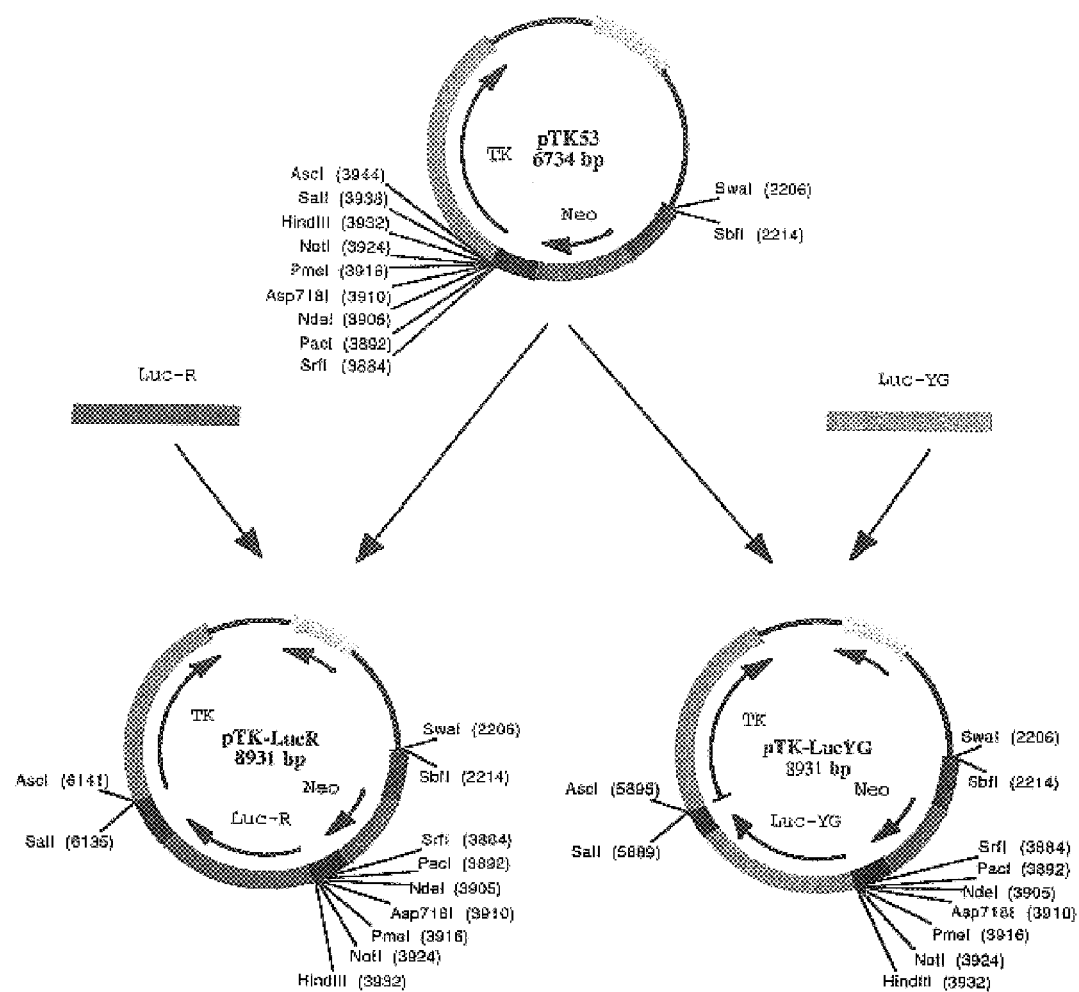
FIG. 2 is schematic depicting construction of the pTK-LucR and pTK-LucYG vectors. For pTK-LucR, a polynucleotide encoding LucR is introduced into pTK53. Thus, the pTK-LucR construct contains the PGK-P gene, a neomycin (Neo$^r$) gene, a thymidine kinase (TK) gene and sequence encoding red luciferase (Luc-R). For pTK-LucYG, a polynucleotide encoding LucYG is introduced into pTK53. Thus, the pTK-LucYG construct contains the PGK-P gene, a neomycin (Neo$^r$) gene, a thymidine kinase (TK) gene and a sequence encoding yellow-green luciferase (Luc-YG).

B. Introduction of Luciferase pTK-LucYG and pTK-LucR: The yellow green luciferase gene was isolated from pGL3 vector (Promega) as a HindIII-SalI fragment and was cloned into pGK53 that was linearized with the same enzymes. The new construct was designated pTK-LucYG (8931 bp), shown in FIG. 2.

The red luciferase gene was isolated from pGL3-red vector (Dr. Christopher Contag, Stanford University, Stanford, Calif.) as a HindIII-SalI fragment and was cloned into pGK53 that was linearized with the same enzymes. The new construct was designated pTK-LucR (8931 bp), shown in FIG. 2.

Example 2

Insertion of Targeting Sequences

A. Generation of vitronectin targeting vector: The targeting construct pTKLR-Vn was generated by inserting vitronectin (VN) DNA sequences into pTK-LucR vector.

Vitronectin (VN) is an abundant glycoprotein present in plasma and the extracellular matrix of most tissues. In a previous study, it was shown that heterozygous mice carrying one normal and one null VN allele and homozygous null mice completely deficient in vitronectin demonstrate normal development, fertility, and survival. This suggests that VN is not essential for cell adhesion and migration during normal mouse development (Zheng, X., et al., Proc Natl Acad Sci USA 1995 92:12426–30). Mouse vitronectin genomic DNA sequence of 5004 bp was obtained from GenBank database (Accession number X72091). Based on this sequence, a 1.63 kb 3' end vitronectin fragment was amplified (reverse primer VN1R, SEQ ID NO:11: CTGTATTTAAATCTGCCCAC-CCTATTCAGGACAGTAGTC; forward primer VN1F, SEQ ID NO:12: CCAATGCATCAACCCAGCCAGGAGGAGTGCG) using mouse C57BL6 genomic DNA as template (Genome Systems, Inc., St. Louis, Mo.). This fragment was digested with SwaI and NsiI and cloned into pTK-LucR (linearized with SwaI and SbfI). This construct was designated as pTK-LucR3. Subsequently, a 2.35 kb 5' end vitronectin fragment was amplified (reverse primer VN2R, SEQ ID NO:13: AACGCGTCGACTTCGGAGATGTTTCGGGG ATAACCAGG, forward primer VN2F, SEQ ID NO:14: TTGGCGCGCCCCATAGAGAAGAGACACCAAAGGC ACGCTC) using mouse C57BL/6 genomic DNA as template. This fragment was digested with SalI and AscI and cloned into pTK-LucR vector that was linearized with SalI and AscI. This construct was designated as pTKLR-Vn. FIG. 3A shows the restriction map of pTKLR-Vn vector. The polylinker between the neomycin gene and red luciferase gene is used to insert the VEGF promoter or other promoters of interests. The predicted homologous recombination between pTKLR-Vn and vitronectin gene is illustrated in FIG. 3B. Upon insertion of the VEGF-LucR transgene cassette, the endogenous vitronectin gene is destroyed. FIG. 3C shows the genomic DNA sequence of VN.

B. Generation of Fos targeting vector: The targeting construct pTKLG-Fos was generated by inserting FosB DNA sequences into pTK-LucYG vector.

FosB is one of the members of the Fos family. It plays a functional role in transcriptional regulation. It has been shown that FosB mice are born at a normal frequency, are fertile and present no obvious phenotypic or histologic abnormalities (Gruda et al (1996) *Oncogene* 12:2177–2185). A 28.8 kb genomic region that contains mouse FosB DNA sequence was obtained from GenBank database (Accession number AF093624).

Figure 4A:
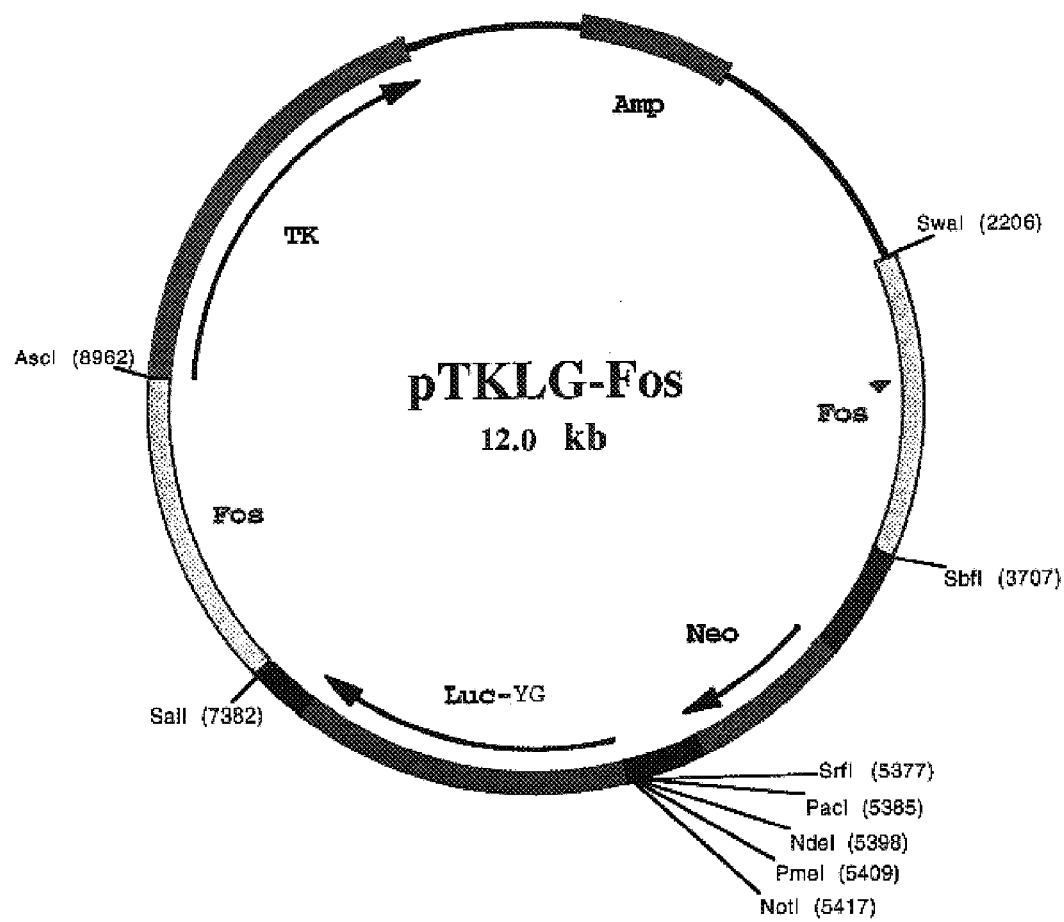
FIG. 4A is a schematic depicting the vector pTKLG-Fos. Sequences homologous to the FosB gene are inserted into pTK-LucYG such that they flank the Neo$^r$ gene and the Luc-YG coding sequence.

Using this sequence, a 1.71 kb 5' end FosB fragment was amplified (forward primer FosB1F, SEQ ID NO:15: CTG-TATTTAAATCCCGTTTCTCACTGTGCCTGTGTC; reverse primer FosB1R, SEQ ID NO:16: GTCTCCTGCAGGCTTCCTCCTCCTTGTTCCTTGCG) using mouse C57BL/6 genomic DNA as template. This fragment was digested with SwaI and SbfI and cloned into pTK-LucYG vector that was linearized with SwaI and SbfI. This construct was designated as pTK-LucYG3. Subsequently, a 1.58 kb 3' end FosB fragment was amplified (forward primer FosB2F, SEQ D NO:17: AACGCGTC-GACGGATGGGATTGACCCCCAGCCCTC; reverse primer FosB2R, SEQ ID NO:18: TTGGCGCGCCCCTTGCCTCCACCTCTCAAATGC) using mouse C57BL/6 genomic DNA as template. This fragment was digested with SalI and AscI and cloned into pTK-LucYG vector that was linearized with SalI and AscI. This construct was designated as pTKLG-Fos (FIG. 4A).

Figure 4B-2:
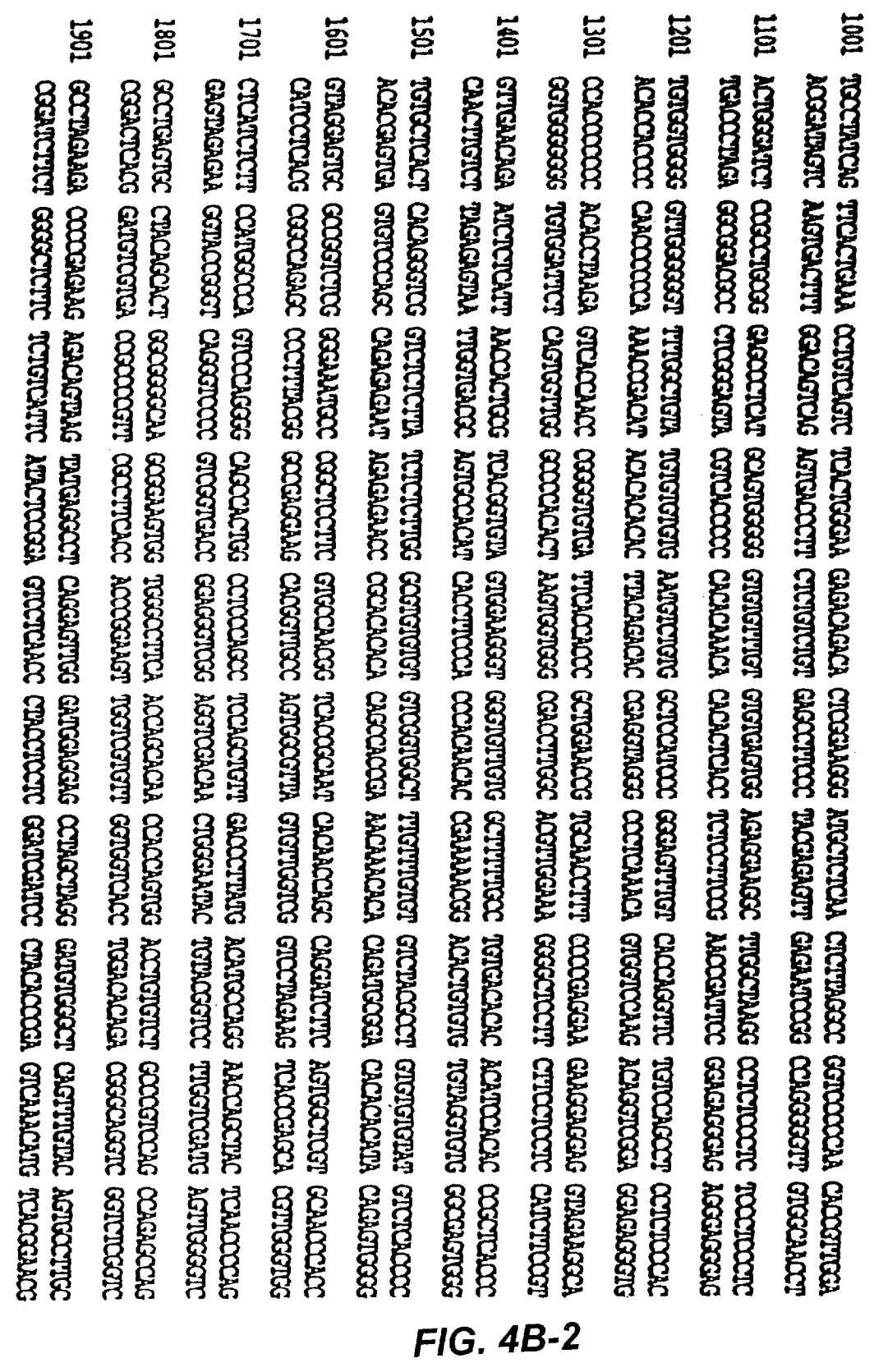

The polylinker between the neomycin gene and red luciferase gene is used to insert the VEGFR2 promoter (Example 3, FIGS. 5A–C, enhancer FIG. 11), Tie2 promoter (Example 3, FIG. 15, enhancer FIG. 16), as well as, other promoters of interests. The predicted homologous recombination between the targeting vector bearing the VEGFR2 promoter (FIG. 14) or the Tie2 promoter (FIG. 19) and FosB gene is also illustrated. As shown in the Figures, the VEGFR2-LucYG transgene cassette and Tie2-LucYG transgene cassette is inserted downstream of FosB gene translational stop signal. Therefore, the targeted transgenic mice should still have a functional FosB gene while expressing the transgenes. FIG. 4B shows the DNA sequence of FosB.

Example 3

Insertion of Promoter Sequences of Interest

A. pTKLR-Vn/VEGF: Mouse VEGF genomic DNA sequence of 2240 bp that contains a partial VEGF promoter region was obtained from GenBank (accession number: U41383). Accordingly, primers were designed to amplify a 0.69 kb (VF1-VR1A; Table 1) and a 0.98 kb fragment (VF2-VR2; Table 1). It was confirmed that each pair of primers can amplify the predicted product using mouse 129SvJ genomic DNA as template.

TABLE 1

| Name | SEQ ID NO: | Sequence |
|---|---|---|
| VF1 | 19 | ACCTC ACTCT CCTGT CTCCC CTGAT TCCCA A |
| VR1A | 20 | GCTCT GGCGG TCACC CCCAA AAGCA |
| VF2 | 21 | CCCTT TCCAA GACCC GTGCC ATTTG AGC |
| VR2 | 22 | ACTTT GCCCC TGTCC CTCTC TCTGT TCGC |
| KF1 | 23 | GCTGC GTCCA GATTT GCTCT CAGAT GCG |
| KR1 | 24 | TTCTC AGGCA CAGAC TCCTT CTCCG TCCCT |
| KF2 | 25 | CAGAT GGACG AGAAA ACAGT AGAGG CGTTG GC |
| KR2 | 26 | GAGGA CTCAG GGCAG AAAGA GAGCG |
| TF3 | 27 | AGCTT AGCCT GCAAG GGTGG TCCTC ATCG |
| TF2 | 28 | CAAAT GCACC CCAGA GAACA GCTTA GCCTG C |
| TR1 | 29 | GCTTT CAACA ACTCA CAACT TTGCG ACTTC CCG |

Conditions for PCR amplification are shown in FIG. 6. These primers were used for PCR screening of mouse 129/SvJ genomic DNA BAC (bacterial artificial chromosome) library (Genome Systems, Inc., St. Louis, Mo.). The library, on average, contained inserts of 120 kb with sizes ranging between 50 kb to 240 kb. A large genomic DNA fragment that contained VEGF promoter region was obtained. Southern blot analysis was performed to map the VEGF promoter region. A unique HindIII restriction site was mapped approximately 7.8 kb upstream of the ATG translational start codon of the VEGF gene. The sequences between HindIII and ATG translational start codon are inserted into the polylinker of pTKLR-Vn vector to finish the construction of targeting vector that contains VEGF-LucR transgene (FIG. 3A).

B. VEGFR2 Targeting Vector pTKLG-Fos-KPN

1. Cloning of VEGFR2 Promoter

Mouse VEGFR2 genomic DNA sequence of 1079 bp that contains partial VEGFR2 promoter region was published previously (Ronicke et al (1996) Cir. Res. 79:277–285). Accordingly, primers that were able to amplify a 0.45 kb (KF1-KR1; Table 1) and a 0.58 kb fragment (KF2-KR2; Table 1) were designed. It was confirmed that each pair of primers can amplify the predicted product using mouse 129SvJ genomic DNA as template. DNA sequences for these primers are shown in Table 1 above. PCR amplification conditions are shown in FIG. 6. These primers were used for PCR screening of mouse 129/SvJ genomic DNA BAC library. A large genomic DNA fragment of VEGFR2 promoter region was obtained. Based on the VEGFR2 restriction map that was published (Ronicke et al, supra), a 4.6 kb HindIII-XbaI fragment that covers the VEGFR2 promoter region was subcloned from the VEGFR2 BAC clone into the pSK vector (Stratagene, La Jolla, Calif.) and linearized with HindIII and XbaI. This construct was designated pSK-K6.

2. Engineering of the VEGFR2 Promoter

Figure 5B:
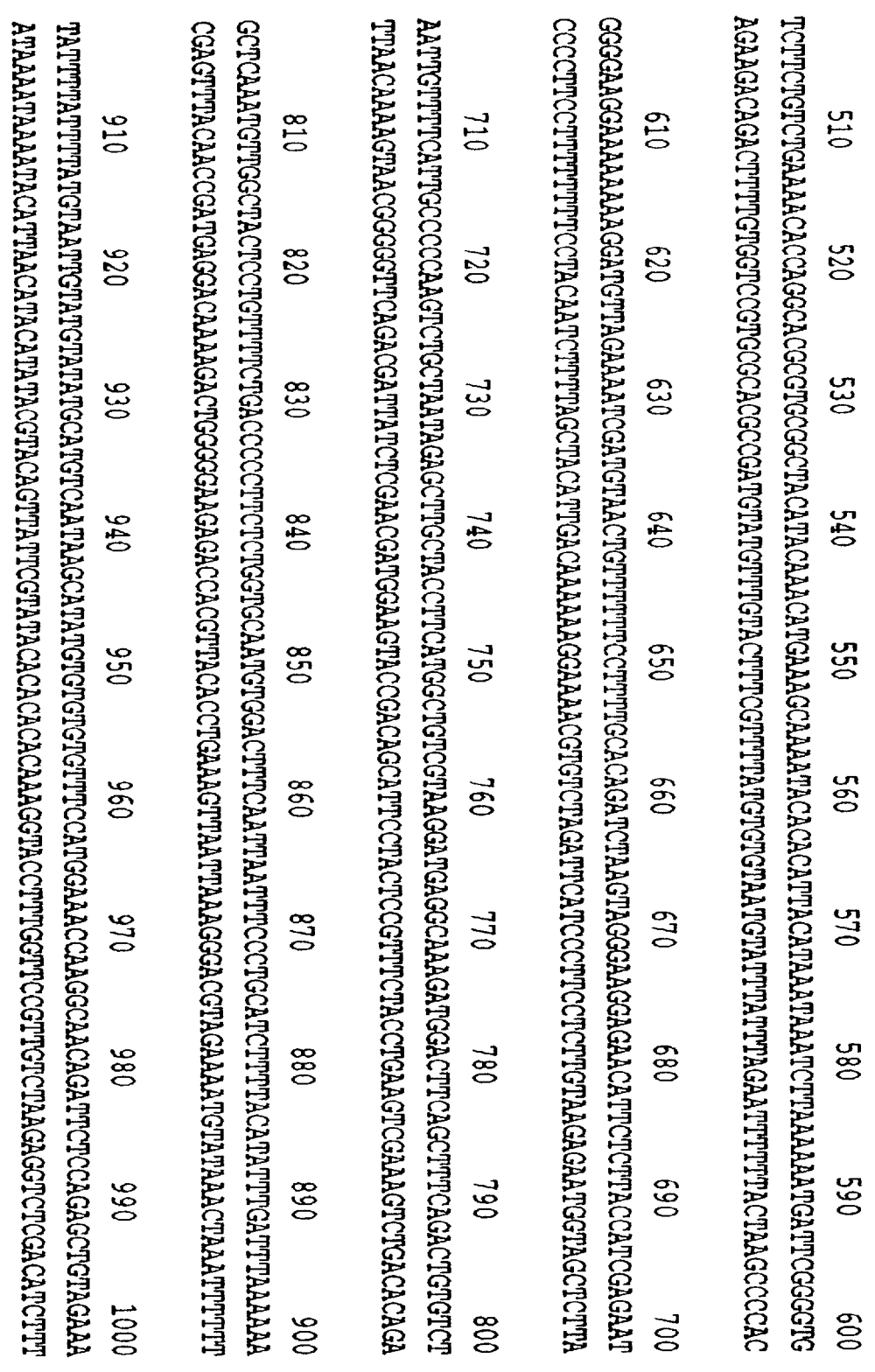

PSK-K6 was engineered to deleted a 159 bp sequence of the 3' end promoter region spaning from ATG translational start codon to an XbaI site. A 0.3 kb 3' end fragment was amplified by PCR (Forward primer (VR2F): CGCTAGT-GTGTAGCCGGCGCTCTC (SEQ ID NO:30); reverse primer (VR2R): ATAAGAATGCGGCCGCCTGCAC-CTCGCGCTGGGCACAG (SEQ ID NO:31)) and digested with Bsu361 and NotI. This fragment was used to replace the 0.45 kb Bsu361-NotI fragment of pSK-K6 and the resulting construct was designated PSK-KP, which contains VEGFR2 promter sequences of 4.5 kb, spanning from a HindIII site to the ATG translational start codon. The 4.5 kb VEGFR2 promoter was fully sequenced and the sequence is shown in FIGS. 5A–C (SEQ ID NO:32). The present invention includes, but is not limited to, an isolated polynucleotide having at least 90%, preferably 92%, more preferably 95%, and even more preferably 98% sequence identity to the sequence presented as SEQ ID NO: 32.

3. Cloning of VEGFR2 Enhancer

In a recent report, it was described that a 511 bp sequence within the first intron of VEGFR2 gene functions as an endothelial cell specific enhancer. (Kappel et al (1999) Blood 12: 42844292). Accordingly, this VEGFR2 enhancer sequence was amplified by PCR using VEGFR2 BAC clone DNA. (Forward primer (VEF): ACACGCCTCGAGAAAT-GTGCTGTCTTTAGAAGCCACTG (SEQ ID NO:33); Reverse primer (VER): ACACGCGTCGACGATCCAAT-AGGAAAGCCCTTCCATAAAC (SEQ ID NO:34)). This fragment was digested with XhoI and SalI and cloned into the SalI site of the pSK vector. The resulting construct was designated PSK-KN. The 511 bp VEGFR2 enhancer is shown in FIG. 11 (SEQ ID NO:35).).

4. pGL3B2

Figure 12:
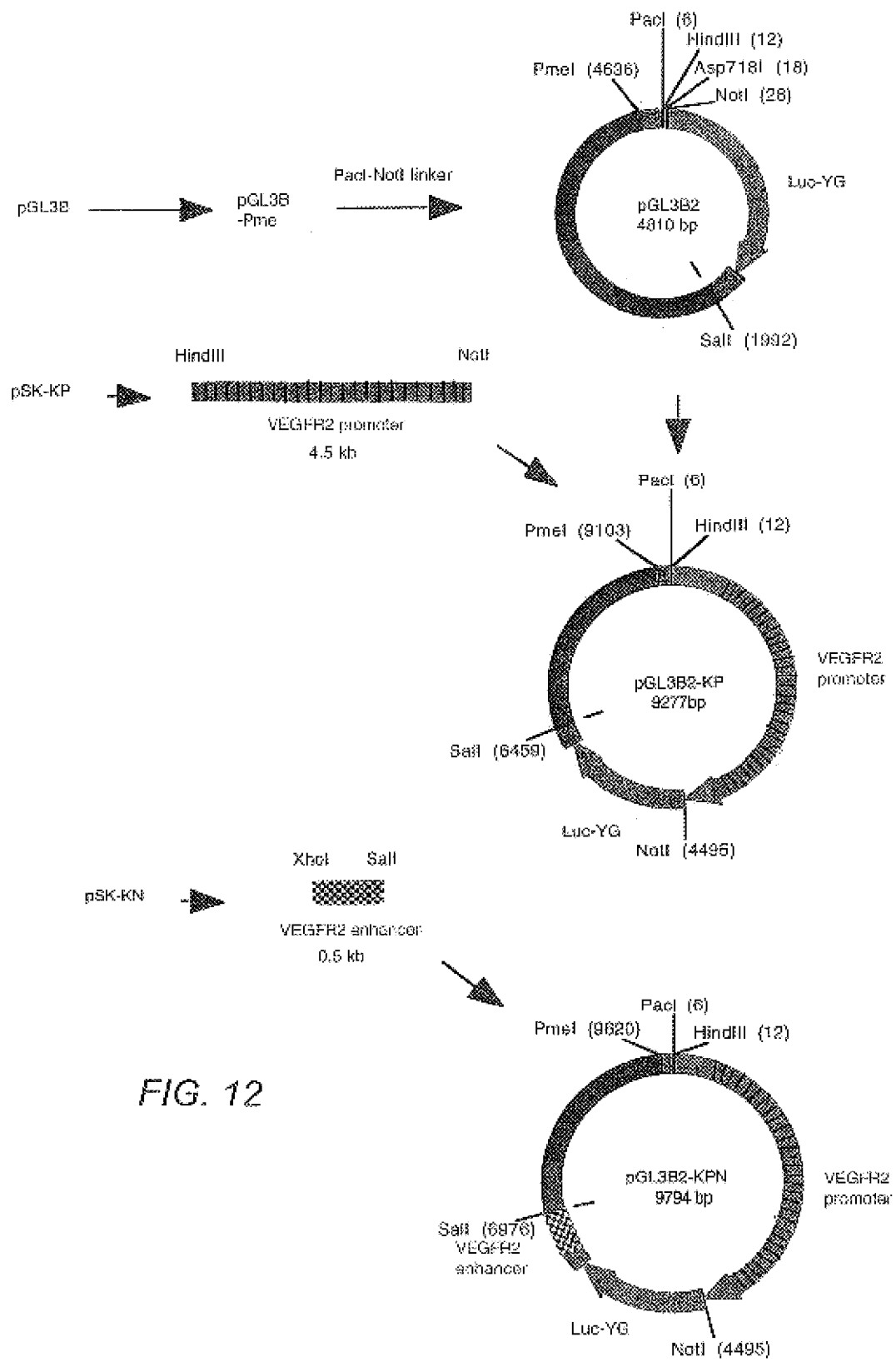
FIG. 12 is a schematic depicting engineering of the-pGL3B2-KPN construct. PGL3B (Promerga, Madison, Wis.) contains the yellow-green luciferase gene (Luc-YG). The construct contains a 4.5 kb fragment of the VEGFR2 promoter and a 0.5 kb fragment of the VEGFR2 enhancer.

The yellow-green luciferase containing vector pGL3B (Promega, Madison, Wis.) was re-engineered as illustrated in FIG. 12. First, pGL3B was digested with NotI and then blunt ended with T4 DNA polymerase. A PmeI linker (New England Biolab) was then ligated into the vector. The new vector, pGL3B-Pme, was double digested with Asp718 and HindIII and ligated with a synthetic linker resulted from annealing of two complementary oligos. (GL3B-Forward GTACTTAATTAAGCTTGGTACCCGGGGCGGCCGC (SEQ ID NO:36); GL3B-Reverse AGCTGCGGCCGC-CCCGGGTACCAAGCTTAATTAA (SEQ ID NO:37)). The new vector was designated pGL3B2.

Construction of pGL3B2-KPN

As illustrated in FIG. 12, the VEGFR2 promoter is isolated from pSK-KP as a HindIII-NotI fragment and cloned into the pGL3B2 vector that is linearized with HindIII and NotI. The new construct was designated pGL3B2-KP. Subsequently, the VEGFR2 enhancer was isolated from pSK-KN as a XhoI-SalI fragment and cloned into the pGL3B2-KP vector that was linearized with SaiI. The new construct was designated pGL3B2-KPN.

6. Construction of pTKLG-Fos-KPN

Figure 14:
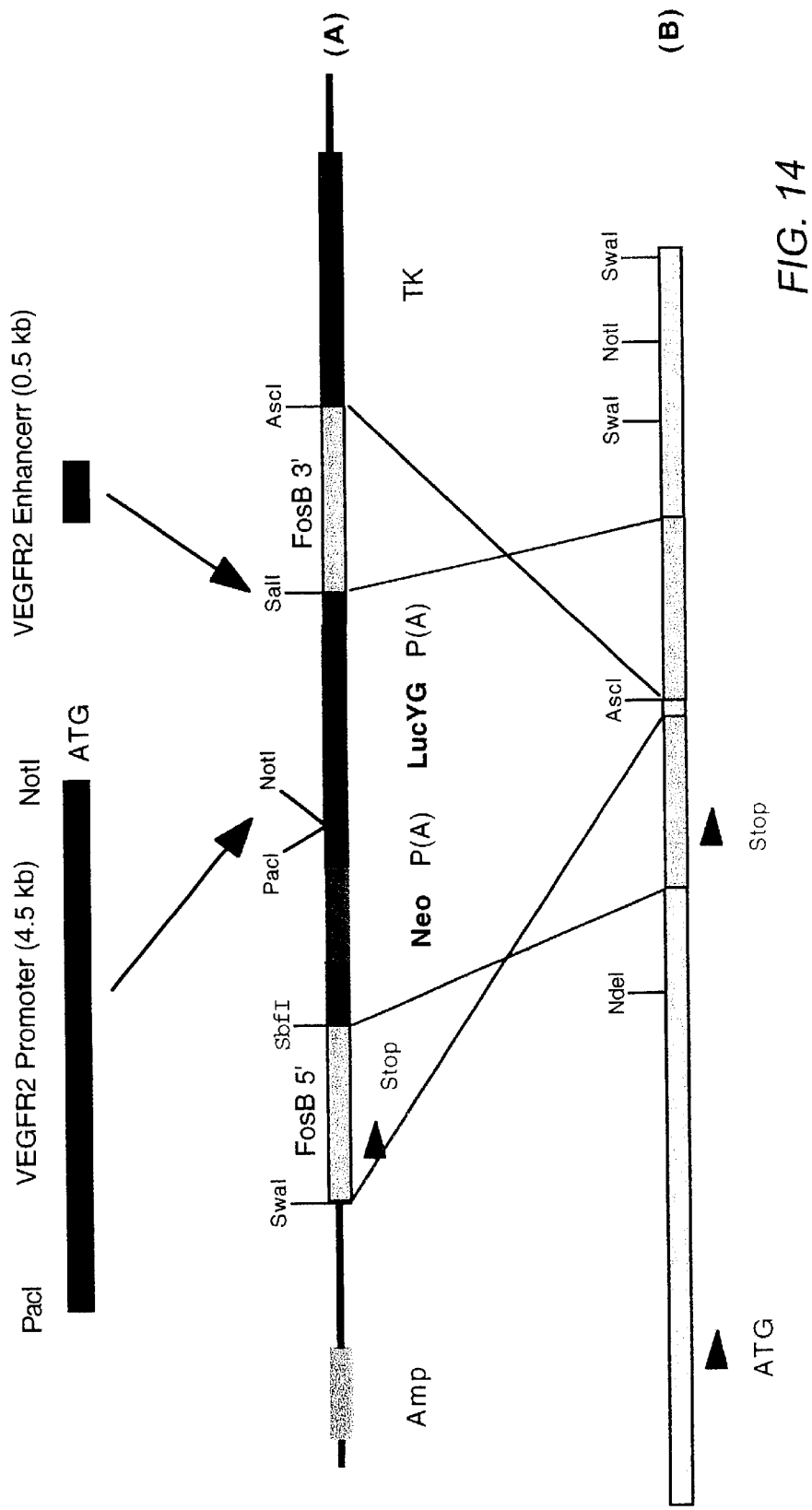
FIG. 14 is a schematic depicting targeting of the linearized pTKLG-Fos vector to the FosB chromosomal locus. The VEGFR2 promoter is cloned into the polylinkers between Neo and Luc-YG. Upon homologous recombination, the Neo-VEGFR2-LucYG transgene will be inserted into a sequence associated with production of FosB. In the figure, (A) shows the targeting vector, and (B) shows the mouse target gene. In the figure, Neo—neomycin resistance encoding sequences; TK—thymidine kinase encoding sequences; LucYG—yellow green luciferase from pGL3-control vector (Promega, Madison, Wis.). Regions bearing FosB gene translational start and stop codons are indicated with arrows. Poly(A) sequences are placed upstream of the polylinker to prevent or minimize read-through translation.

The VEGFR2 promoter-luciferase-enhancer cassette was isolated from pGL3B2-KPN as a PacI-SalI fragment and cloned into the pTKLG-Fos vector that was linearized with PacI and SalI. The new construct was designated pTKLG-Fos-KPN. (FIG. 13), Using this targeting construct, the VEGFR2 promoter-Luciferase-enhancer transgene cassette is targeted to the FosB gene locus through homologous DNA recombination, as illustrated in FIG. 14.

C. Tie2 Targeting Vector pTKLG-Fos-TPN

1. Cloning of Tie2 Promoter

A 477 bp region of the mouse Tie2 promoter has been isolated and sequenced. (Fadel et al (1998) *Biochem J.* 330:335–343). Using this region, primers that were able to amplify a 0.45 kb (TF3-TR1; Table 1) and a 0.47 kb fragment (TF2-TR1; Table 1) were designed. It was confirmed that each pair of primers amplified the predicted product using mouse 129SvJ genomic DNA as template. DNA sequences for these primers are shown in Table 1 above and PCR amplification conditions are shown in FIG. 6. These primers were used for PCR screening of mouse 129/SvJ genomic DNA BAC library. A large genomic DNA fragment of Tie2 promoter region was obtained. Based on the Tie2 genomic DNA restriction map that was published (Dumont et al (1994) *Genes and Development* 8:1897–1909), a 10.5 kb Asp718-EcoRV fragment spanning the Tie2 promoter region was subcloned from the Tie2 BAC clone into the pSK vector linearlized with Asp718 and EcoRV. The new construct was designated pSK-T67.

2. Engineering of the Tie2 Promoter pSK-T67 was further engineered to delete all the 3.4 kb sequence spaning from ATG translational start codon to EcoRV site. A 1.0 kb 3' end promoter region was amplified by PCR (T2 Forward primer: TATCAACACTCGGGAG-GCTGAGGGAG (SEQ ID NO:38); T2 reverse primer. ATAAGAATGCGGCCGCACTTCCCCA-GATCTCCCCATCCAGC (SEQ ID NO:39)) and digested with BstAPI and NotI. The 0.55 kb BstAPI-NotI fragment was used to replace the 4.0 kb BstAPI-NotI fragment of pSK-T67 and the resulting construct was designated PSK-TP, which contains Tie2 promter sequences of 7.1 kb, spanning from a Asp718 site to the ATG translational start codon. The 7.1 kb Tie2 promoter was fully sequenced and the sequence was shown in FIG. 15 (SEQ ID NO:40).). The present invention includes, but is not limited to, an isolated polynucleotide having at least 90%, preferably 92%, more preferably 95%, and even more preferably 98% sequence identity to the sequence presented as SEQ ID NO:40.

3. Cloning of Tie2 Enhancer

Figure 16B:
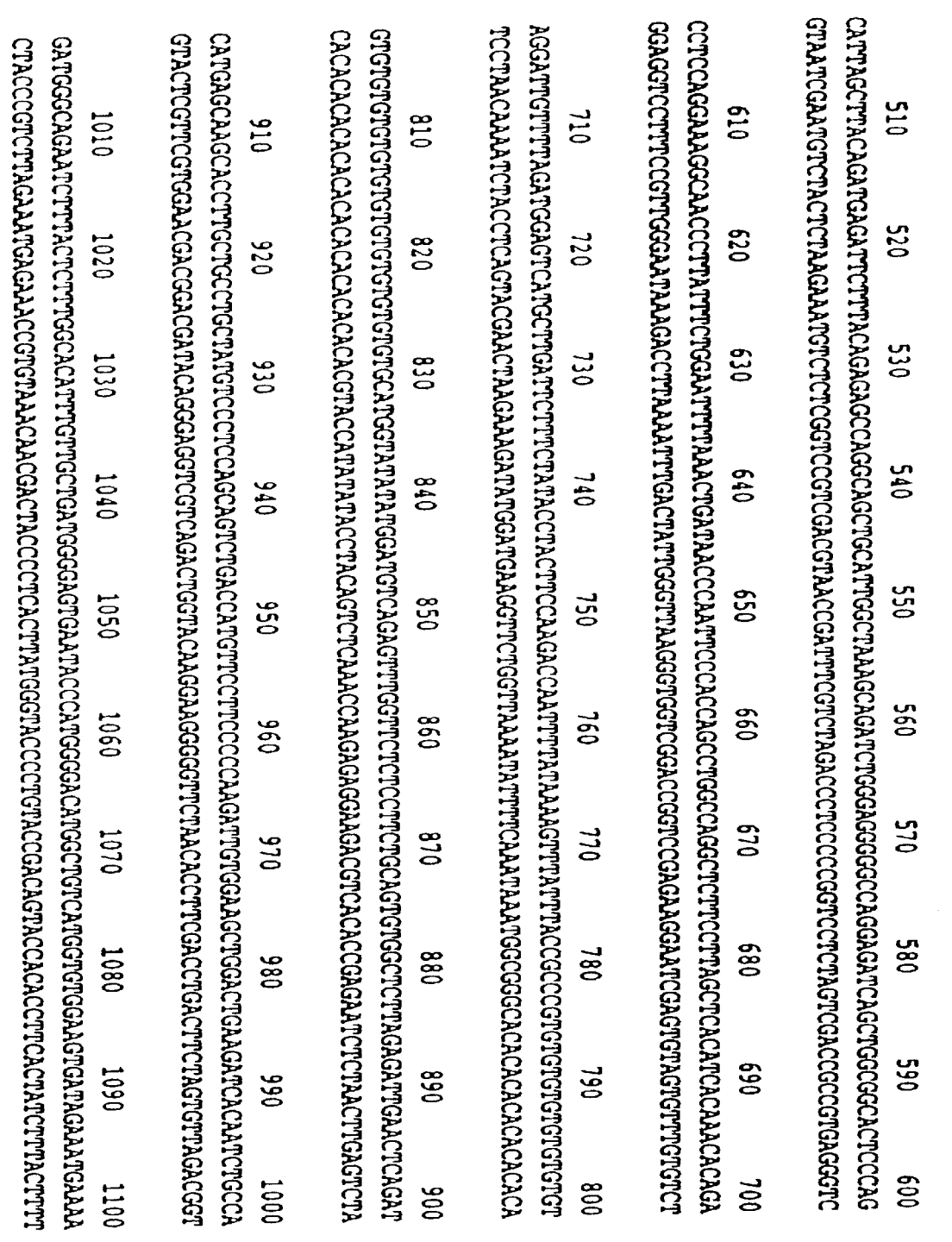

In a previous report, it was described that a 1.7 kb region within the first intron of the Tie2 gene functions as an endothelial cell specific enhancer. (Schiaeger et al (1997) *PNAS USA* 94: 3058–3063). Accordingly, this 1.7 kb Tie2 enhancer region was subcloned from the Tie2 BAC clone DNA as a XhoI-Asp718 fragment into the pSK vector that was linearized with the same enzymes. The Asp718 site was then converted to a SalI site using a SalI linker (New England Biolab). The resulting construct was designated PSK-TN. The 1.7 kb Tie2 enhancer was fully sequenced and the sequence is shown in FIG. 16 (SEQ ID NO:41).).

4. Construction of pGL3B2-TPN

Figure 17:
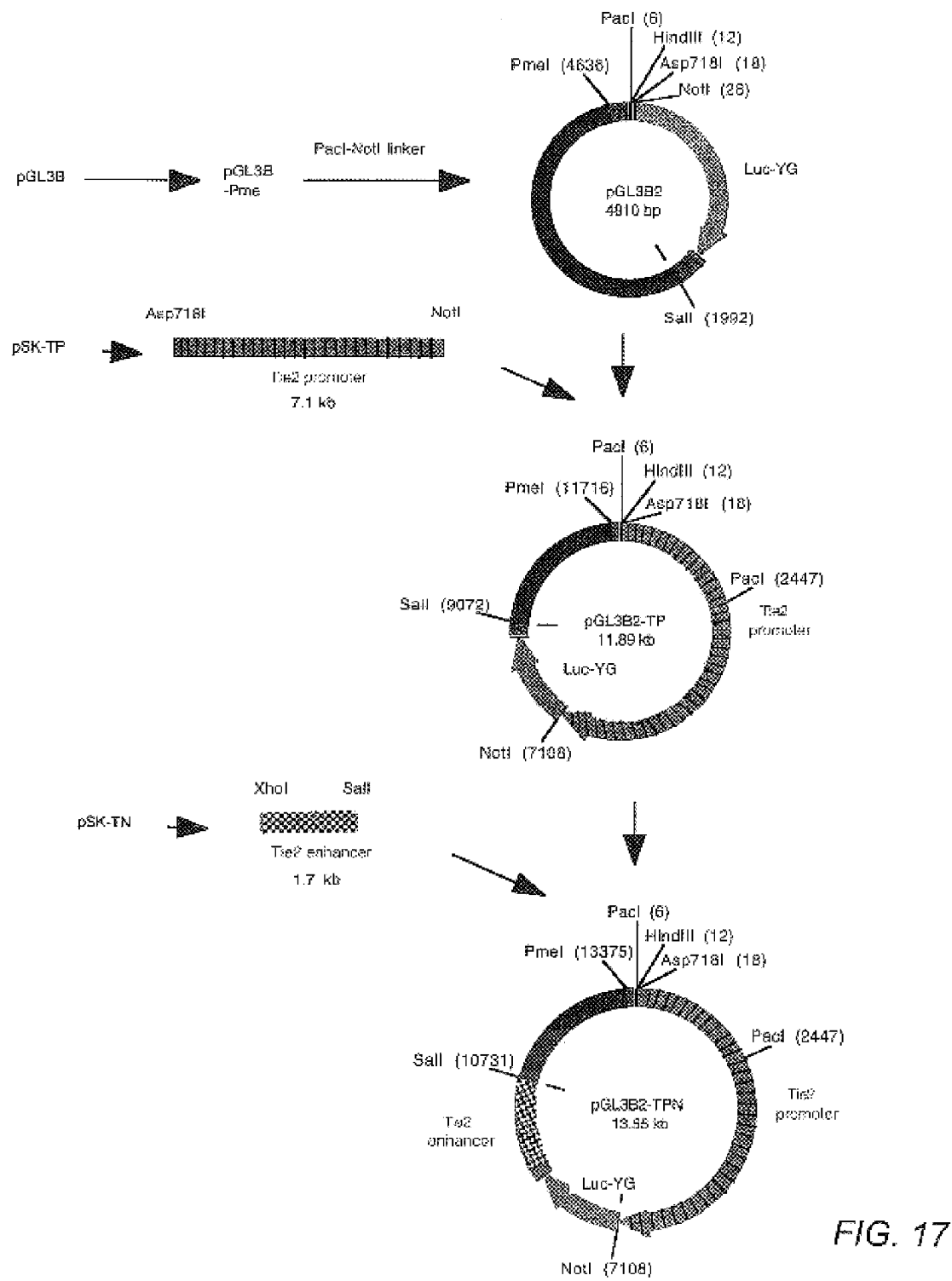
FIG. 17 is a schematic depicting engineering of the pGL3B2-TPN construct. PGL3B (Promerga, Madison, Wis.) contains the yellow-green luciferase gene (Luc-YG). The construct contains a 7.1 kb fragment of the Tie2 promoter and a 1.7 kb fragment of the Tie2 enhancer.

As illustrated in FIG. 17, the Tie2 promoter was isolated from PSK-TP as a Asp718-NotI fragment and cloned into the pGL3B2 vector that was linearized with Asp718 and NotI. The new construct was designated pGL3B2-TP. Subsequently, the Tie2 enhancer was isolated from PSK-TN as a XhoI-SalI fragment and cloned into the pGL3B2-TP vector linearized with SalI. The new construct was designated pGL3B2-TPN.

5. Construction of pTKLG-Fos-KPN

Figure 19:
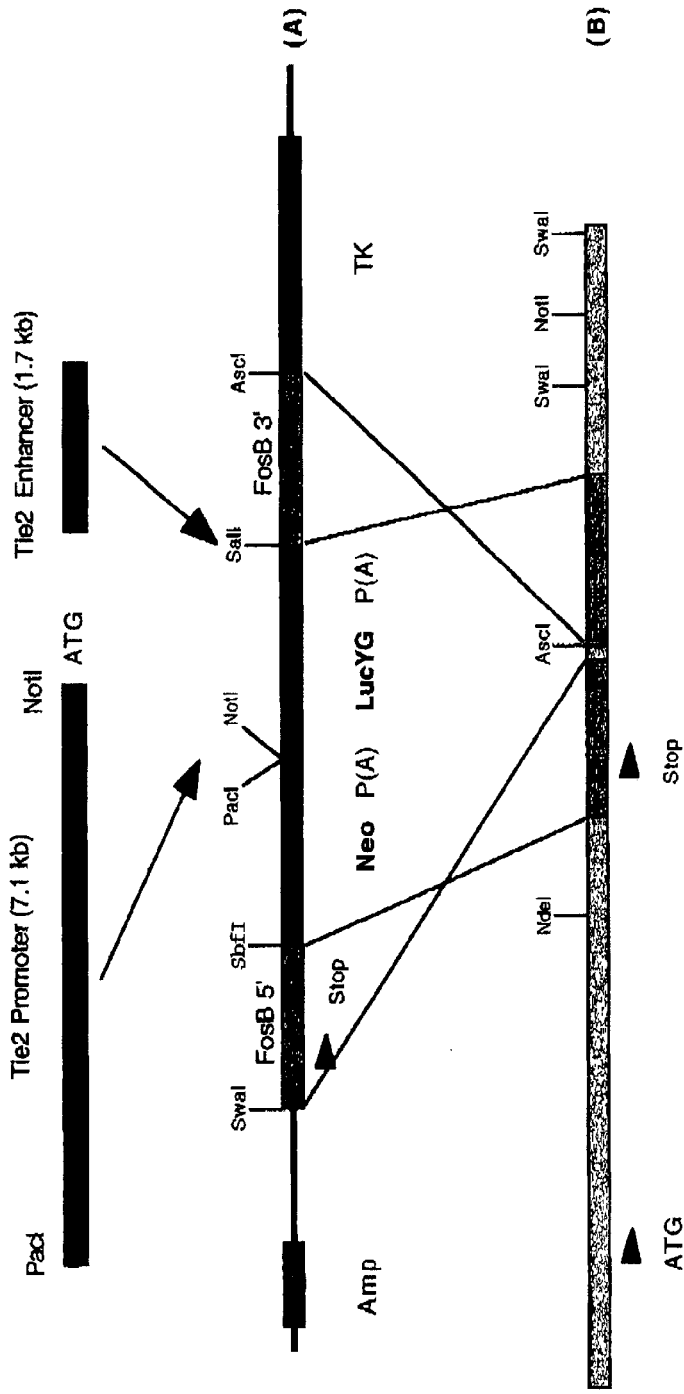
FIG. 19 is a schematic depicting targeting of the linearized pTKLG-Fos vector to the FosB chromosomal locus. The TIE2 promoter is cloned into the polylinkers between Neo and Luc-R. Upon homologous recombination, the Neo-Tie2-LucYG transgene is inserted into the FosB gene. In the figure, (A) shows the targeting vector, and (B) shows the mouse target gene. In the figure, Neo—neomycin resistance encoding sequences; TK—thymidine kinase encoding sequences; LucYG—yellow green luciferase from pGL3-control vector (Promega). Regions bearing FosB gene translational start and stop codons are indicated with arrows. Poly(A) sequences are placed upstream of the polylinker to prevent or minimize read-through translation.

The Tie2 promoter-Luciferase-enhancer cassette is isolated from pGL3B2-TPN as a PacI-SalI fragment and cloned into the pTKLG-Fos vector linearized with PacI and SalI. The new construct was designated pTKLG-Fos-TPN. (FIG. 18 ). Using this targeting construct, the Tie2 promoter-Luciferase-enhancer transgene cassette is targeted to the FosB gene locus through homologous DNA recombination, as illustrated in FIG. 19.

Example 4

Generation of Transgenic Mice Carrying the Constructs of the Present Invention

Figure 7:
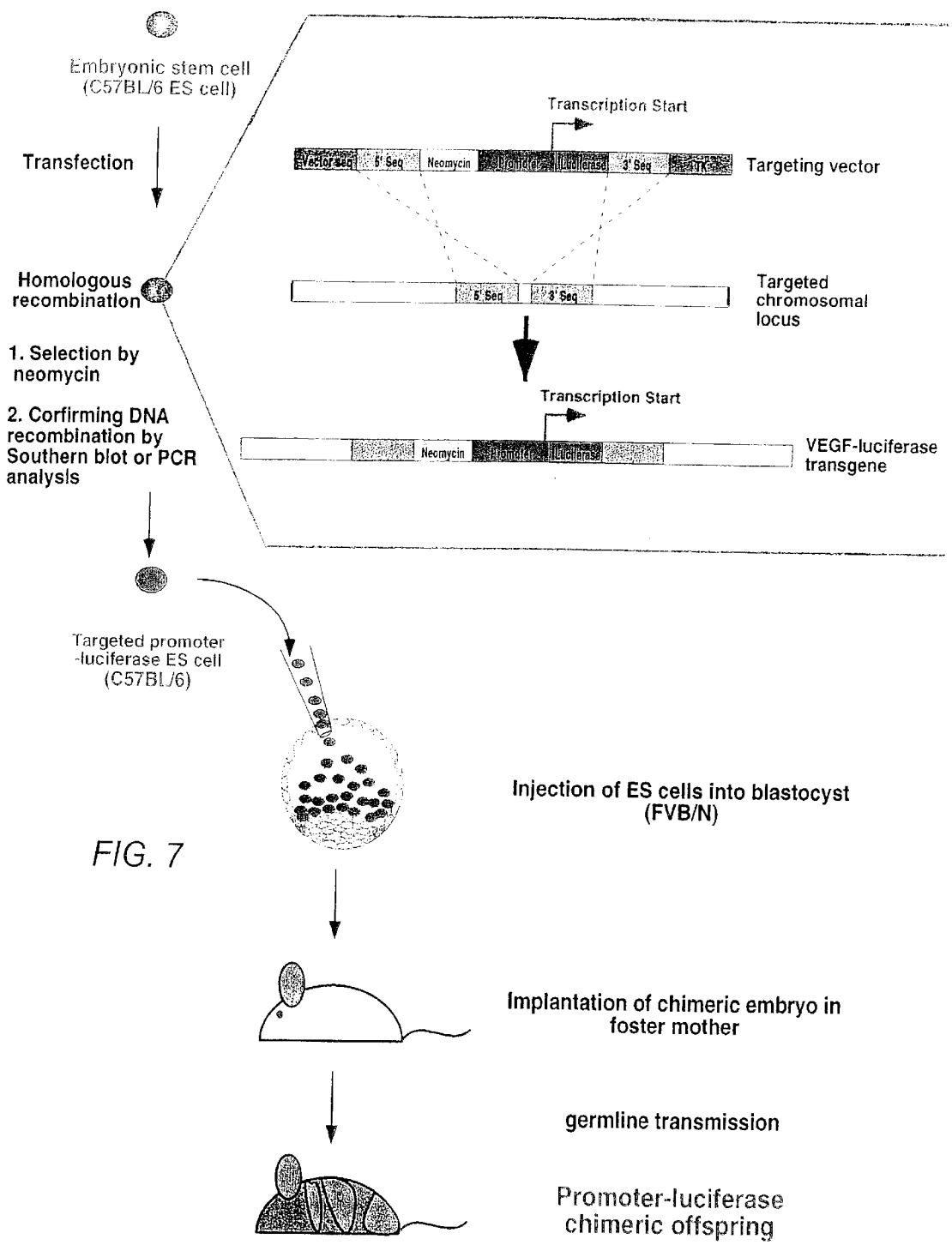
FIG. 7 depicts generation of targeted transgenic mice using the targeting vectors described herein.

A. General Procedure: FIG. 7 depicts a generalized description of generation of transgenic mice using the targeted transgenic vectors described in Example 3. Details regarding embryonic stem (ES) cell culture, transfection, blastocyst injection and implantation to a pseudopregnant foster are described, for example, in Hogan et al (1994) "Manipulating the Mouse Embryo. A Laboratory Manual. Second Edition", Cold Spring Harbour Laboratory Press.

After construction the targeted transgenic construct are transfected into C57BL/6 embryonic stem (ES) cells. (Genome System Inc., Genome Systems, Inc., St. Louis, Mo.) through electroporation. The antibiotic G418 is used to select for cells in which the DNA construct containing the Neo gene is integrated, either randomly or by homologous recombination. The nucleoside analog gancyclovir is converted by TK to a cytotoxic derivative. DNA that has integrated by homologous recombination lose the TK gene and are resistant to the drug, whereas cells that have incorporated the DNA randomly are likely to retain the TK gene. Thus, cells containing random integrations into a chromosomal location that allows the expression of the TK gene are killed. The G418 and gancyclovir resistant clones are then be screened by PCR and Southern blot analysis and those that have homologous DNA recombination is used for FVB/N blastocyst injection (Genome System, Inc.). Between 4–16 blastocysts are transferred to the uterus of a pseudopregnant foster mother. The pups are typically born 17 days after the transfer. Either random bred mice or F1 hybrid mice make suitable recipients. Females of certain random-bred stocks (e.g., CD1 mice, from Charles River laboratories) have very large ampullae, which makes oviduct transfer easier. These mice also generally make good mothers. Alternatively, F1 hybrid females (e.g., B6×CBA F1) can be used as recipients. Although their ampullae are smaller, make exceptionally good mothers,rearing litters as small as two pups. See, for example, Hogan et al. (1994), supra.

B. Screening for Homologous DNA Recombination Positive ES Cells

Figure 8:
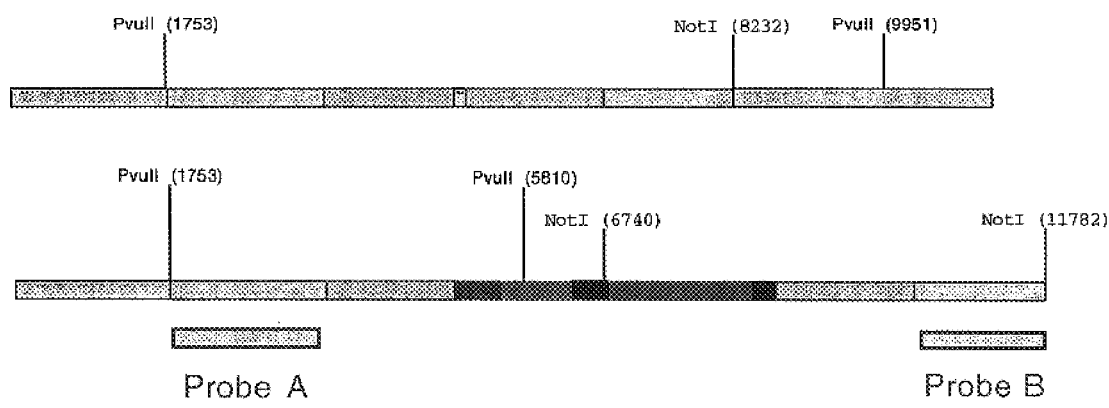
FIG. 8 depicts of schematic representation of Southern blot analysis of homologous DNA recombination between pTKLG-Fos targetting vector and the FosB gene.

1). pTKLG-Fos/VEGFR2: Analysis of homologous DNA recombination between pTKLG-Fos/VEGFR2 targeting vector and the FosB gene is carried out using Southern blot analysis as shown in FIG. 8. Genomic DNA prepared from G418 resistant ES cells is digested with PvuII and probed with probe A to confirm the 5' end DNA recombination. PvuII digestion of DNA bearing homologous recombination reveals two separate bands of 8.2 and 4.0 kb, whereas digestion of DNA from homologous recombination negative clones reveals only the 8.2 kb band. The 3' end of DNA recombination is tested by hybridizing NotI digested DNA with probe B. NotI digestion of DNA bearing homologous recombination will reveal two separate bands of >8.2 kb and 5.0 kb, whereas digestion of DNA from homologous recombination negative clones will only reveal the >8.2 kb band. Once homologous DNA recombination is confirmed, positive clones is selected for FVB/N blastocyst injection.

2) pTKLG-Fos/Tie2: Analysis of homologous DNA recombination between pTKLG-Fos/Tie2 targeting vector and the FosB gene is analyzed by Southern blot in a similar manner as described above for pTKLG-Fos/VEGFR2. Once homologous DNA recombination is confirmed, positive clones are selected for FVB/N blastocyst injection.

3) PTKLR-Vn/VEGF: Analysis of homologous DNA recombination between pTKLR-Vn/VEGF targeting vector and the vitronectin gene is analyzed by PCR. DNA primers designed according to the predicted homologous recombination, are listed in Table 2.

TABLE 2

PCR primers for analysis of homologous DNA recombination between pTKLR-Vn/VEGF targeting vector and the vitronectin gene 5'end primers

| F51 | 5'- CCCAGTGTCTCTGATTTAGGGAGAGCACCTGAG -3' (SEQ ID NO:42) |
| R51 | 5'- CCAGACTGCCTTGGGAAAAGCGCCTC -3' (SEQ ID NO:43) |
| F52 | 5'- CAGTGAGAGTCTTCTCTGTCCCTCAATCGGTTCTG -3' (SEQ ID NO:44) |
| R52 | 5'- TGGATGTGGAATGTGTGCGAGGCCAG -3' (SEQ ID NO:45) |

3'end primers

| F31 | 5'- AATCAAAGAGGCGAACTGTGTGTGAGAGGTCC -3' (SEQ ID NO:46) |
| R31 | 5'- CGGCTCCCCAAAATGTGGAAGCAAGC -3' (SEQ ID NO:47) |
| F32 | 5'- GAATCCATCTTGCTCCAACACCCCAACATC -3' (SEQ ID NO:48) |
| R32 | 5'- CGCCTCCTCTCCCCAGTCTCCCCTTG -3' (SEQ ID NO:49) |

Primers F51-R51 and F52-R52 amplify a 1799 bp and a 1841 bp DNA fragment respectively from the 5' end of the transgene that is integrated into the vitronectin site through homologous DNA recombination, whereas primers F31-R31 and F32-R32 amplify a 3549 bp and a 3428 bp DNA fragment respectively from the 3' end of the transgene that is integrated into the vitronectin site through homologous DNA recombination. Clones that allow successful amplification of both the 5' end and 3' end of the integrated transgene are selected for FVB/N blastocyst injection.

C. Analysis of Chimeric Mice

The pups developed from injected blastocysts contain chimeras, as can be identified by their agouti coat color when an ES cell derived from a mouse having a dark coat color (e.g., C57BL/6) is injected into the blastocyst of a light coat color animal (e.g., FVB/N, genotype B/B). DNA analysis (e.g., Southern blotting, PCR) is conducted to further confirm the presence of the transgene in these pups as described above in Section B. These animals may be obtained commercially, for example from The Jackson Laboratory, Bar Harbor, Me.

D. Generating Targeted Transgenic C57BL/6 Mice with White Coat Color

Figure 9:
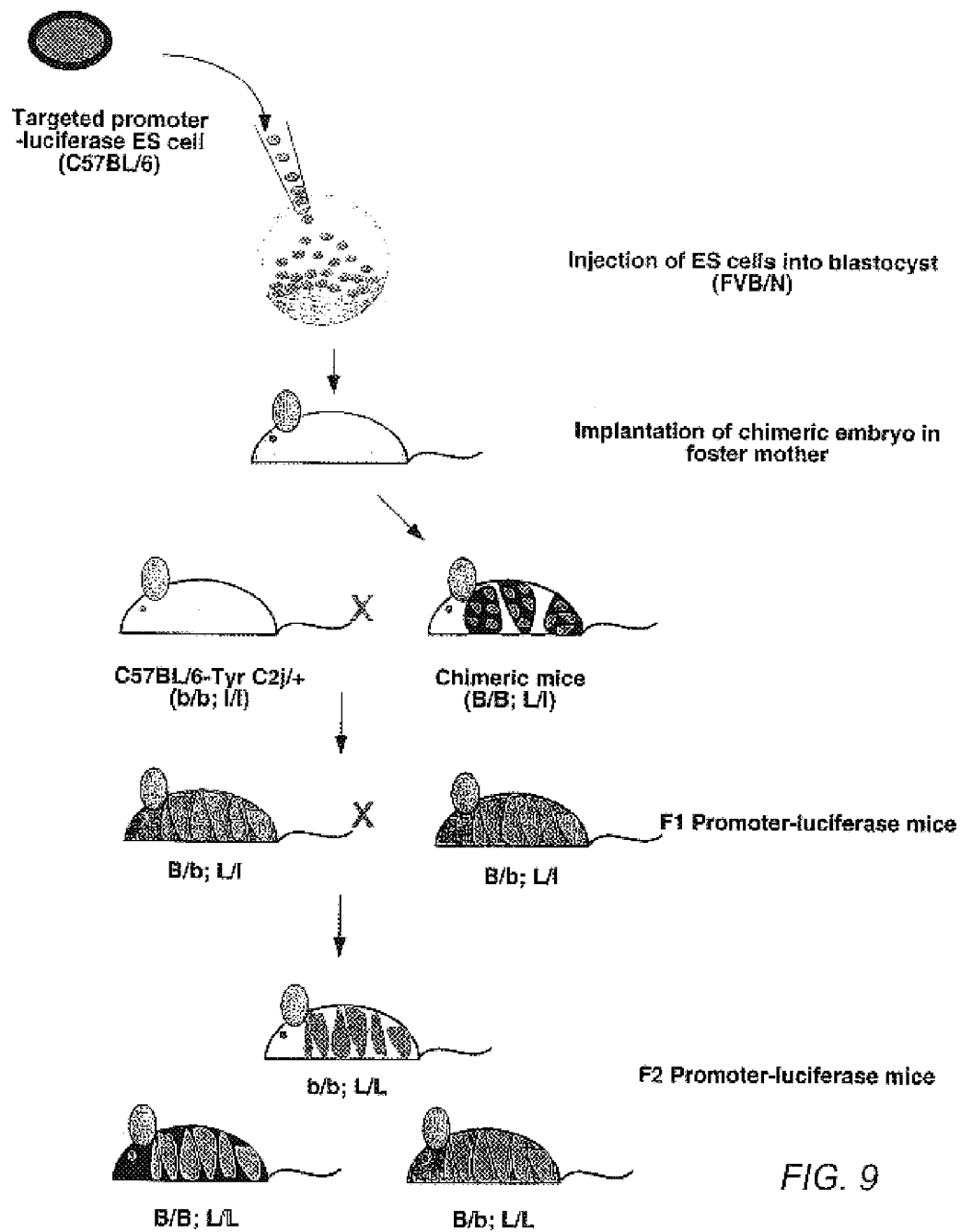
FIG. 9 depicts generation of targeted transgenic mice, using the targeting vectors described herein, and crosses using such transgenics as well as their offspring (F1, first generation; F2, second generation).

Breeding of the chimeric mice generates homozygous targeted transgenic mice, as depicted in FIG. 9. The targeted mice are used to monitor gene expression through the measurement of luciferase mediated light emission from the mice. In a preferred embodiment, the targeted mouse has a light coat color (e.g., white coat color), because the black colored coat (an example of a dark coat color) of C57BL/6 mice can absorb light emitted from the body and may interfere the sensitivity of the bioluminescence assay. An inbred mouse strain C57BL/6-Tyr C2j/+ strain (Jackson Laboratory, Bar Harbor, Me.) is available for this purpose. This strain of mice have white color coat, yet they still have the same genetic background as C57BL/6 mice except that the gene responsible for the black coat color is mutated. Unfortunately, C57BL/6-Tyr C2j/+ ES cells are not currently available. Therefore, the designed breeding program illustrated in FIG. 9 is aimed to generate mice that are homozygous for the target transgene and have white coat color. C57BL/6 ES cells are prepared as described above and introduced into a suitable blastocyst (e.g., from the FVB/N strain of mice). The blastocysts are implanted into a foster mother. Chimeric mice are shown in FIG. 9 as white animals with black and green patches. Chimeric animals are bred with C57BL/6Tyr C2j/+ mice to create F1 hybrids. Subsequent breeding of the F1 hybrids generates several type of mice, including the one that is homozygous for the target transgene and has a white coat color (shown in FIG. 9 as b/b; L/L), which is used for in vivo gene regulation monitoring.

A C57BL/6 mouse and a C57BL/6-Tyr C2j/+ mouse are considered to be substantially isogenic. Accordingly, the method of the present invention exemplified in FIG. 9 provides a means for generating breeding groups of substantially isogenic mice in a selected genetic background carrying at least one transgene of interest.

E. Dual Luciferase Targeted Transgenic Mice

Figure 10:
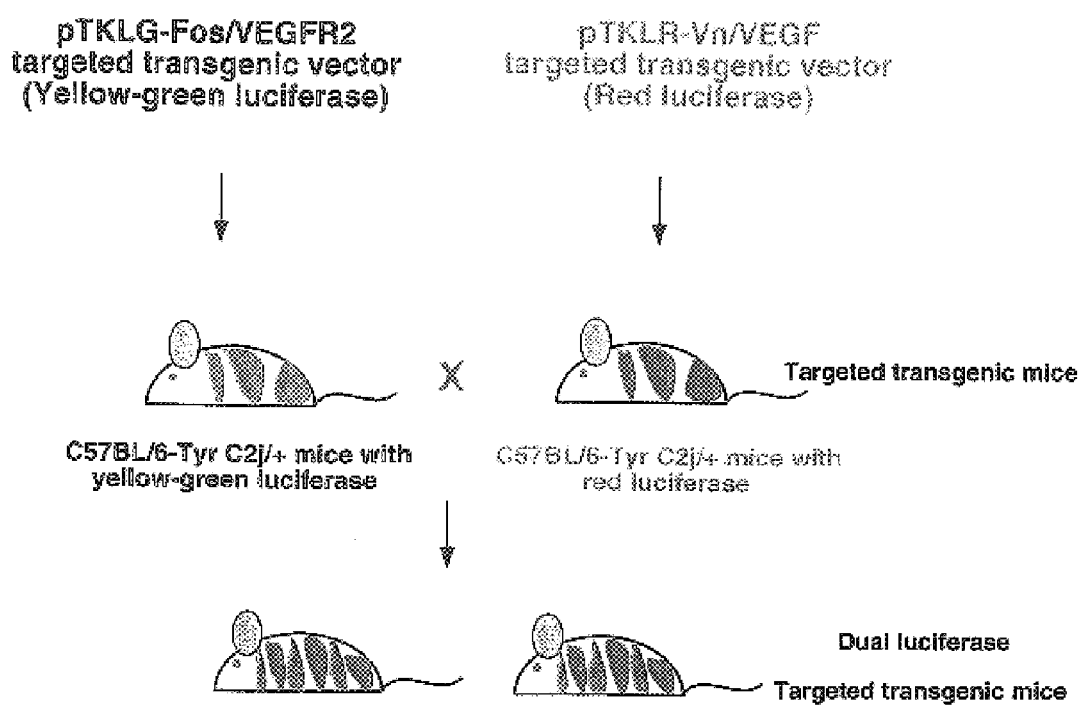
FIG. 10 depicts crosses using transgenic mice of the present invention to generate dual luciferase transgenic mice.

As described above, two targeting vectors are generated. PTKLR-Vn carries a red luciferase gene and is targeted into vitronectin locus. PTKLG-Fos carries a yellow-green luciferase gene and is targeted into FosB locus. A number of promoters, including VEGF promoter, VEGFR2 promoter, and Tie2 promoter are cloned into these vectors, as described above. Subsequently three type of targeted transgenic mice are generated. VEGF mice carry VEGF promoter-red luciferase transgene (VEGF-LucR) integrated into vitronectin locus. VEGFR2 mice carry VEGFR2 promoter-yellow-green luciferase (VEGFR2-LucYG) transgene integrated into FosB locus. Tie2 mice carry Tie2 promoter-yellow-green luciferase (Tie2-LucYG) transgene integrated into FosB locus. Through a breeding program illustrated in FIG. 10, dual luciferase targeted transgenic mice are produced, carrying both of the VEGF-LucR and the VEGFR2-LucYG transgenes. The degradation of luciferin by yellow-green luciferase and red luciferase generates lights that emit at 540 nM and 610 nM respectively. These wavelengths of light are measured individually using a photo-counting camera (intensified CCD). Therefore, both VEGF expression and VEGFR2 expression, for example, can then be monitored in the same mouse at the same time.

Example 5

Modulation of Expression Mediated by VEGFR2 Promoter Sequences

The 4.5 kb VEGFR2 promoter identified in Example 3 and shown in FIGS. 5A–C (SEQ ID NO:32) was cloned into the polylinker of pGL3B2 (FIG. 12) to control the transcription of luciferase coding sequences (FIG. 12). A 0.5 kb VEGFR2 enhancer sequence was cloned down stream of the luciferase to enhance endothelial specific expression. The resulting expression construct (pGL3B2-KPN; FIG. 12) was used to transiently transfect primary bovine endothelial cells (Clonetics) using lipofectamine (Promega). The cells were seeded onto 12-well plastic culturing plates (Nunc) prior to transfection. The transfection was carried out according to the manufacture's instructions (Promega). Plasmid pRL-TK (Promega), containing Renilla luciferase driven by the thymidine kinase promoter, was used as an internal control in all transfection experiments. The primary bovine endothelial cells were cultured in EGM-2 MV medium (Clonetics) at 37° C. in 5% $CO_2$, 95% air. After transfection, the cells were lysed with passive lysis buffer (Promega) and assayed with the Dual-Luciferase Reporter Assay System (Promega) for luciferase activity.

Several angiogenesis and neoplasticity inhibitors (Sigma) were tested for their effects on the expression of VEGFR2 expression in primary bovine endothelial cells transiently transfected with pGL3B2-KPN as described above. Briefly, 24 hrs after 1 transfection, the cells were treated with selected angiogenesis and neoplasticity inhibitors for 36 hrs and assayed for luciferase activity. The tested compounds included the neoplasticity inhibitor Mithramycin, and angiogenesis inhibitors 2-Methoxyestradiol, Thalidomide, and Fumagillin. At least some of the tested compounds had the effect of reducing luciferase expression mediated by the 4.5 kb VEGFR2 promoter.

These results suggest that sequences derived from the 4.5 kb VEGFR2 promoter are useful for screening for compounds capable of modulating VEGFR2-mediated angiogenesis.

Example 6

Modulation of Expression Mediated by Tie2 Promoter Sequences

The 7.1 kb Tie2 promoter identified in Example 3 and shown in FIG. 15 (SEQ ID NO:40) was cloned into the polylinker of pGL3B2 (FIG. 17) to control the transcription of luciferase coding sequences (FIG. 17). The resulting expression construct (pGL3B2-TP; FIG. 17) was used to transiently transfect primary bovine endothelial cells (Clonetics) using lipofectamine (Promega). The cells were seeded onto 12-well plastic culturing plates (Nunc) prior to transfection. The transfection was carried out according to the manufacture's instructions (Promega). Plasmid pRL-TK (Promega), containing Renilla luciferase driven by the thymidine kinase promoter, was used as an internal control in all transfection experiments. The primary bovine endothelial cells were cultured in EGM-2 MV medium (Clonetics) at 37° C. in 5% $CO_2$, 95% air. After transfection, the cells were lysed with passive lysis buffer (Promega) and assayed with the Dual-Luciferase Reporter Assay System (Promega) for luciferase activity.

Several angiogenesis and neoplasticity inhibitors (Sigma) were tested for their effects on the expression of Tie2 expression in primary bovine endothelial cells transiently transfected with pGL3B2-TP as described above. Briefly, 24 hrs after transfection, the cells were treated with selected angiogenesis and neoplasticity inhibitors for 36 hrs and assayed for luciferase activity. The tested compounds included the neoplasticity inhibitor Mithramycin, and angiogenesis inhibitors 2-Methoxyestradiol, Thalidomide, and Fumagillin. At least some of the tested compounds had the effect of reducing luciferase expression mediated by the 7.1 kb Tie2 promoter.

These results suggest that sequences derived from the 7.1 kb Tie2 promoter are useful for screening for compounds capable of modulating Tie2-mediated angiogenesis.

As is apparent to one of skill in the art, various modification and variations of the above embodiments can be made without departing from the spirit and scope of this invention. These modifications and variations are within the scope of this invention.

What is claimed is:

1. A transgenic mouse or progeny thereof, comprising in its genome an expression cassette comprising a cis-acting transcription regulator operably linked to a reporter sequence encoding a light-generating protein, wherein said cis-acting transcription regulator consists of the sequence presented as SEQ ID NO:35 and the sequence presented as SEQ ID NO:32 wherein expression of the light-generating protein is increased during angiogenesis.

2. The transgenic mouse of claim 1, wherein said light-generating protein is a luciferase.

* * * * *